United States Patent [19]

Lahm et al.

[11] Patent Number: 5,276,039

[45] Date of Patent: Jan. 4, 1994

[54] SUBSTITUTED INDAZOLE ARTHROPODICIDES

[75] Inventors: George P. Lahm, Wilmington; Thomas M. Stevenson, Newark, both of Del.

[73] Assignee: E. I. Du Pont de Nemours and Company, Wilmington, Del.

[21] Appl. No.: 646,649

[22] Filed: Feb. 13, 1991

Related U.S. Application Data

[63] Continuation-in-part of Ser. No. 249,883, Sep. 27, 1988, abandoned, and a continuation-in-part of Ser. No. 247,690, Sep. 22, 1988, abandoned.

[51] Int. Cl.$^5$ .................. A61K 31/38; A61K 31/415; C07D 471/04; C07D 491/04
[52] U.S. Cl. ............................ 514/287; 514/227.5; 514/229.5; 514/230.2; 514/292; 514/293; 514/403; 544/34; 544/99; 544/101; 546/82; 546/83; 548/359.5; 548/359.1; 548/113; 548/358.5
[58] Field of Search ............... 514/227.5, 229.5, 230.2, 514/287, 292, 293, 403; 544/34, 99, 101; 546/82, 83; 548/369, 370, 371, 372

[56] References Cited

U.S. PATENT DOCUMENTS

| | | | |
|---|---|---|---|
| 4,766,877 | 10/1988 | Timmler et al. | 71/92 |
| 5,081,140 | 1/1992 | Jautelat et al. | 514/383 |
| 5,216,007 | 6/1993 | Miller et al. | 514/383 |

FOREIGN PATENT DOCUMENTS

| | | |
|---|---|---|
| 0097425 | 5/1983 | European Pat. Off. . |
| 8806583 | 9/1988 | PCT Int'l Appl. . |
| 8807994 | 10/1988 | PCT Int'l Appl. . |

*Primary Examiner*—Johann Richter
*Attorney, Agent, or Firm*—James A. Costello

[57] ABSTRACT

Indazole arthropodicides, compositions containing them and a method for controlling arthropods employing these indazoles as the active ingredient. The indazoles have the following general formula wherein Q, X, Y, $R_1$ and m are as defined in the text:

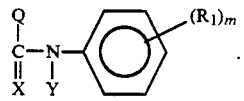

18 Claims, No Drawings

SUBSTITUTED INDAZOLE ARTHROPODICIDES

CROSS-REFERENCE TO RELATED PATENT APPLICATION

This application is a continuation-in-part via the PCT of application Ser. No. 07/249,883 filed on 27 September 1988 and application Ser. No. 07/247,690, filed on 22 September 1988, both now abandoned.

BACKGROUND OF THE INVENTION

U.S. Pat. No. 4,070,365 discloses insecticidal compounds of the formula

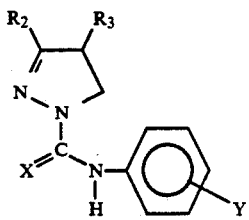

wherein
- $R_2$ and $R_3$ are independently alkyl, cycloalkyl, pyridyl or thienyl optionally substituted with halogen, alkyl or nitro, or a phenyl group optionally substituted with 1 or 2 substituents selected from halogen, alkyl, haloalkyl, cycloalkyl alkylthio, alkoxy, mono or dialkylamino, nitro, phenyl optionally substituted with halogen or cyano;
- Y is halogen, $NO_2$, alkyl, haloalkyl, cycloalkyl, alkylthio, alkoxy, dialkylamino, alkylsulfonyl, acyl, acylamino, cyano, or a phenyl optionally substituted with halogen; and X is O or S.

U.S. Pat. No. 4,663,341 discloses insecticidal compounds of the formula

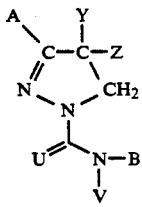

wherein
- A is unsubstituted or substituted phenyl;
- B is unsubstituted or substituted phenyl;
- U is O, S or NR;
- Y is alkyl, carbonyl or phenyl each of which may be optionally substituted; and
- Z is an organic radical other than hydrogen.

Vaughan, *J. Org. Chem.*, 20 (1955), pages 1619 to 1626, discloses 1,5-diphenyl-2-pyrazoline-3-carboxamide. No utility is given for the disclosed compound which, in any event, does not suggest a compound of the instant invention.

Harhash et al., *J. Heterocyclic Chem.*, 21 (1984), at page 1013, discloses the preparation of five pyrazoline compounds, none of which is disclosed in the instant application. No utility is given for any of said compounds:

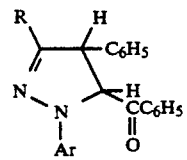

where R/Ar are $C_6H_5/C_6H_5$; $CO_2C_2H_5/C_6H_5$; $C(O)NHC_6H_5/C_6H_5$; $CH=CHC_6H_5/C_6H_5$; and $CH_3/4-NO_2-C_6H_4$.

WO 88/900910 disclosed insecticidal pyrazolines such as compounds of the formula:

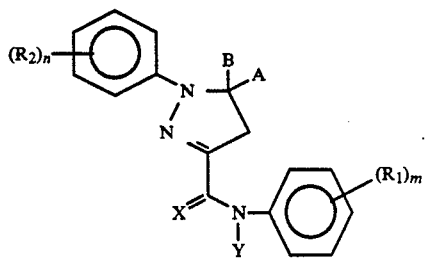

WO 88/302995 discloses insecticidal pyrazolines such as compounds of the formula;

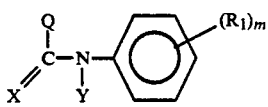

wherein,
Q is $(R_2)_n$

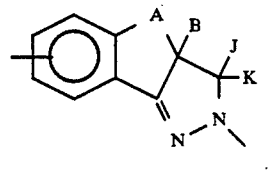

A is 1, 2 or 3-atom bridge having 0 to 3 carbon atoms and 0 to 1 oxygen atom, $NR_6$ group, or $S(O)q$ group, wherein each carbon individually can be substituted with 1 to 2 substituents selected from 1 to 2 halogen, C to $C_6$ alkyl, $C_2$ to $C_4$ alkoxycarbonyl or phenyl optionally substituted with 1 to 3 substituents selected from W and one of the carbon atoms can be C(O) or C(S).

EP-A-153,127 discloses insecticidal compounds of the formula

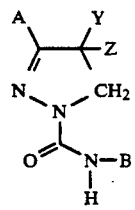

wherein
A is unsubstituted or substituted phenyl;

B is unsubstituted or substituted phenyl;
U is O, S or NR;
Y is alkyl, carbonyl or a phenyl group; and
Z is cycloalkyl, or a phenyl group.

This application is a cognate of applications bearing U.S. Ser. Nos. 07/249,883 and 07/247,690.

SUMMARY OF THE INVENTION

This invention pertains to the following compounds including all of their geometric and stereoisomers, agriculturally suitable salts thereof, agricultural compositions containing them and their use as arthropodicides:

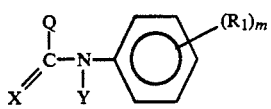   I wherein:
Q is

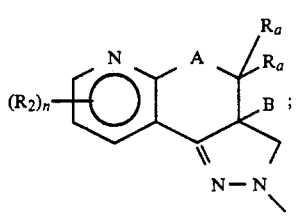   Q-1

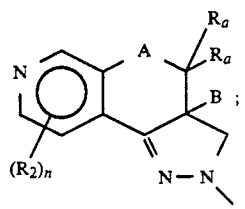   Q-2

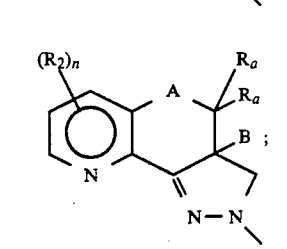   Q-3

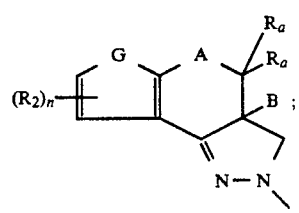   Q-4

Q-5

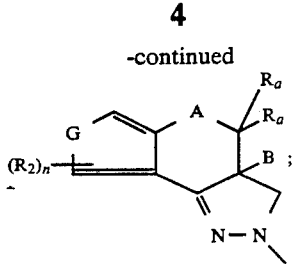   Q-6

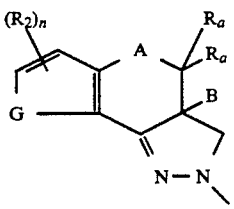   Q-7 or

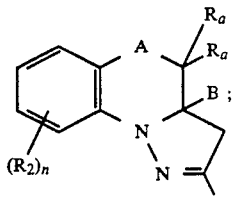   Q-8

G is O or S;
A is a 0, 1 or 2-atom bridge comprising 0 to 2 carbon atoms, 0 to 1 oxygen atoms, 0 to 1 $S(O)_q$ groups or 0 to 1 $NR_6$ groups wherein each carbon atom is optionally substituted with 1 to 2 substituents selected from $R_a$;
B is H, $C_1$ to $C_6$ alkyl, $C_3$ to $C_6$ cycloalkyl optionally substituted with 1 to 2 halogens or 1 to 2 $CH_3$, $C_4$ to $C_1$ to $C_6$ haloalkyl, $C_2$ to $C_6$ alkenyl, $C_2$ to $C_6$ alkynyl, $C_2$ to $C_6$ alkoxyalkyl, $C_2$ to $C_6$ cyanoalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl, phenyl substituted with $(R_5)p$, benzyl, benzyl substituted with 1 to 3 substituents independently selected from W, or $OR_7$ when Q is $Q_1$ to $Q_7$;
W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;
$R_1$, $R_2$ and $R_5$ are independently selected from $R_3$, halogen, CN, $N_3$, SCN, $NO_2$, $OR_3$, $SR_3$, $SOR_3$, $SO_2R_3$, $OC(O)R_3$, $OSO_2R_3$, $CO_2R_3$, $C(O)R_3$, $C(O)NR_3R_4$, $SO_2NR_3R_4$, $NR_3R_4$, $NR_4C(O)R_3$, $OC(O)NHR_3$, $NR_4C(O)NHR_3$ and $NR_4SO_2R_3$, or when m, n or p is 2, $R_1$, $R_2$ or $R_5$ can be —OCH$_2$O—, —OCH$_2$CH$_2$O—, or —CH$_2$CH$_2$O—, each of which can be substituted with 1 to 4 halogen atoms or 1 to 2 methyl groups;
$R_3$ is H, $C_1$ to $C_6$ alkyl, $C_1$ to $C_6$ haloalkyl, $C_2$ to $C_6$ alkenyl, $C_2$ to $C_6$ haloalkenyl, $C_2$ to $C_6$ alkynyl, $C_2$ to $C_6$ haloalkynyl, $C_2$ to $C_6$ alkoxyalkyl, $C_2$ to $C_6$ alkylthioalkyl, $C_1$ to $C_6$ nitroalkyl, $C_2$ to $C_6$ cyanoalkyl, $C_3$ to $C_8$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;

$R_4$ is H, $C_1$ to $C_4$ alkyl or $R_3$ and $R_4$ can be taken together as $(CH_2)_4$, $(CH_2)_5$ or $(CH_2CH_2OCH_2CH_2)$;

$R_6$ is H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, phenyl optionally substituted with W;

$R_7$ is H, $C_1$ to $C_4$ alkyl, $C_2$ to $C_4$ alkenyl, $C_2$ to $C_4$ alkynyl, $C_2$ to $C_4$ alkylcarbonyl, $C_2$ to $C_4$ alkoxycarbonyl;

$R_a$ is independently selected from H, $C_1$ to $C_6$ alkyl, $C_2$ to $C_4$ alkoxycarbonyl and phenyl optionally substituted with 1 to 3 substituents independently selected from W;

x is O or S;
n is 1 to 2;
m is 1 to 3;
p is 1 to 3;
q is 0 to 2;

Y is H, $C_1$ to $C_6$ alkyl, $C_2$ to $C_6$ alkoxyalkyl, CHO, $C_2$ to $C_6$ alkylcarbonyl, $C_2$ to $C_6$ alkoxycarbonyl, $C_2$ to $C_6$ haloalkylcarbonyl, $C_1$ to $C_6$ alkylthio, $C_1$ to $C_6$ haloalkylthio, phenylthio, phenylthio substituted with 1 to 3 substituents independently selected from W, or S-J;

J is

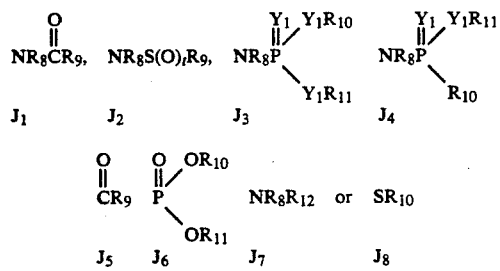

$R_8$ and $R_{12}$ are independently selected from $C_1$ to $C_6$ alkyl, $C_1$ to $C_6$ haloalkyl, $C_3$ to $C_6$ cycloalkyl, $C_4$ to $C_7$ cycloalkylalkyl, phenyl optionally substituted with 1 to 2 substituents independently selected from W, benzyl optionally substituted with 1 to 2 substituents independently selected from W, $C_2$ to $C_6$ cyanoalkyl, $C_2$ to $C_6$ alkoxyalkyl, $C_3$ to $C_8$ alkoxycarbonylalkyl and $C_4$ to $C_8$ dialkylaminocarbonylalkyl, or $R_8$ and $R_{12}$ can be taken together as $(CH_2)_4$, $(CH_2)_5$ or $(CH_2)_2O(CH_2)_2$;

$R_9$ is F, $C_1$ to $C_{22}$ alkyl, $C_1$ to $C_6$ haloalkyl, $C_1$ to $C_{22}$ alkoxy, $C_2$ or $C_8$ dialkylamino, piperidinyl, pyrollidinyl, morpholino, $C_1$ to $C_4$ haloalkoxy, $C_1$ to $C_4$ alkoxy substituted with cyano, nitro, $C_2$ to $C_4$ alkoxy, $C_4$ to $C_8$ alkoxyalkoxy, $C_1$ to $C_2$ alkylthio, $C_2$ to $C_3$ alkoxycarbonyl, $C_3$ to $C_5$ dialkylaminocarbonyl or phenyl, or $R_9$ is phenyl optionally substituted with 1 to 2 substituents independently selected from W, or phenoxy optionally substituted with 1 to 2 substituents independently selected from W;

$R_{10}$ and $R_{11}$ are independently selected from $C_1$ to $C_4$ alkyl, $C_2$ to $C_4$ haloalkyl and phenyl optionally substituted with 1 to 2 substituents independently selected from W, or $R_{10}$ and $R_{11}$ can be taken together as $(CH_2)_2$, $(CH_2)_3$ or $CH_2C(CH_3)_2CH_2$;

t is 0 to 2; and
$Y_1$ is O or S.

In the above definitions, the term "alkyl", used either alone or in compound words such as "alkylthio" or "haloalkyl", denotes straight chain or branched alkyl such as methyl, ethyl, n-propyl, isopropyl or the different butyl, pentyl, hexyl isomers.

Alkoxy denotes straight chain or branched alkenes such as vinyl, 1-propenyl, 2-propenyl, 3-propenyl and the different butenyl pentenyl and hexenyl isomers.

Alkynyl denotes straight chain or branched alkynes such as ethynyl, 1-propynyl, 2-propynyl and the different butynyl, pentynyl and hexynyl isomers.

Alkylthio denotes methylthio, ethylthio and the different propylthio and butylthio isomers.

Alkylsulfinyl, alkylsulfonyl, alkylamino, and the like, are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. When used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$. The terms "halocycloalkyl", "haloalkenyl" and "haloalkynyl" are defined analogously to the term "haloalkyl".

The total number of carbon atoms in a substituent group is indicated by the "$C_i$ to $C_j$" prefix where i and j are integers. For example, $C_1$ to $C_3$ alkylsulfonyl would designate methylsulfonyl through propylsulfonyl; $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl would designate $CH_2CN$ and $C_3$ cyanoalkyl would designate $CH_2CH_2CN$ and $CH(CN)CH_3$; $C_2$ alkylcarbonyl would designate $C(O)CH_3$ and $C_4$ alkylcarbonyl would include $C(O)CH_2CH_2CH_3$ and $C(O)CH(CH_3)_2$; and as a final example, $C_3$ alkoxycarbonylalkyl would designate $CH_2CO_2CH_3$ and $C_4$ alkoxycarbonylalkyl would include $CH_2CH_2CO_2CH_3$, $CH_2CO_2CH_2CH_3$ and $CH(CH_3)CO_2CH_3$.

Preferred Compounds A are those of Formula I wherein:

A is $CR_aR_a$, S, O or $NR_6$;

B is H, $C_1$ to $C_6$ alkyl, $C_1$ to $C_6$ haloalkyl, $C_2$ to $C_6$ alkenyl, $C_2$ to $C_6$ alkynyl, $C_2$ to $C_6$ alkoxyalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl or phenyl substituted by $(R_5)p$;

W is Cl, F, Br, Cn, $CF_3$, $C_1$ to $C_2$ alkyl, $C_1$ to $C_2$ alkoxy, $OCF_2H$, $OCF_3$ or $NO_2$;

$R_2$ is $R_3$, halogen, CN, SCN, $NO_2$, $OR_3$ or $SR_3$;

$R_3$ is H, $C_1$ to $C_4$ alkyl, $C_1$ to $C_2$ haloalkyl, $C_3$ to $C_4$ alkenyl, $C_3$ to $C_4$ haloalkenyl, propargyl, phenyl, benzyl, or phenyl or benzyl substituted with one of F, Cl, Br, $CF_3$, $OCF_3$, $OCF_2H$ or $NO_2$;

p is 1 or 2;
m is 1 or 2;
X is O;

Y is H, $C_1$ to $C_4$ alkyl, $SCH_3$, $SCCl_3$, $SO_2CH_3$, $SC_6H_5$, $2-NO_2-C_6H_4S$, $C(O)CH_3$, $C(O)CH_2CH_3$, $C(O)CF_3$; $CO_2CH_3$, $CO_2CH_2CH_3$, or S-J;

J is $J_1$, $J_2$, $J_3$, $J_4$ or $J_5$;

$R_8$ and $R_{12}$ and independently selected from $C_1$ to $C_6$ alkyl, $C_1$ to $C_6$ haloalkyl, $C_5$ to $C_6$ cycloalkyl, $C_3$ to $C_8$ alkoxycarbonylalkyl, phenyl, benzyl and phenethyl, each phenyl, benzyl and phenethyl optionally substituted with W, or, $R_8$ and $R_{12}$ can be taken together as $(CH_2)_4$, $(CH_2)_5$ or $(CH_2)_2O(CH_2)_2$;
$R_{10}$ and $R_{11}$ are independently selected from $C_1$ to $C_3$ alkyl or phenyl; and
t is 2.
Preferred compounds B are Compounds A wherein:
B is H, $C_1$ to $C_4$ alkyl, $C_3$ to $C_4$ alkoxycarbonylalkyl, $CO_2R_3$, $C(O)R_3$, phenyl or phenyl substituted with $(R_5)p$;
$R_1$ is halogen, CN, SCN, $NO_2$, $OR_3$, $SR_3$, $SO_2R_3$, $CO_2R_3$, $C(O)R_3$ or is $R_3$ with one substituent in the 4-position;
$R_5$ is H, $R_3$, halogen, CN, SCN, $NO_2$, $OR_3$, $SR_3$, $SO_2R_3$, $C(O)R_3$, $OSO_2R_3$, $CO_2R_3$, $C(O)R_3$, $C(O)NR_3R_4$, $SO_2NR_3R_4$ or $NR_3R_4$; or, when m or p is 2;
$R_1$ and $R_5$ can be $—CH_2C(CH_3)_2O—$, $OCH_2CH_2O—$, $OCF_2CF_2O—$ or $—CH_2CF_2O—$;
$R_3$ is $C_1$ to $C_4$ alkyl, $C_1$ to $C_2$ haloalkyl, $C_3$ to $C_4$ alkenyl or propargyl;
$R_4$ is H or $CH_3$;
$R_a$ is H, $CH_3$, $CO_2CH_3$ or $CO_2CH_2CH_3$;
m and p are independently 1 or 2 and one substituent is in the para-position;
Y is H, $CH_3$, $COCH_3$, $CO_2CH_3$ or S-J;
J is $J_1$ or $J_2$;
$R_8$ is $C_1$ to $C_4$ alkyl or phenyl optionally substituted with Cl or $CH_3$;
$R_9$ is $C_1$ to $C_{20}$ alkyl, $C_1$ to $C_{20}$ alkoxy, $C_1$ to $C_6$ haloalkyl, dimethylamino, phenyl optionally substituted with Cl or $CH_3$, or, $R_9$ is $C_1$ to $C_4$ alkoxy substituted with $C_2$ to $C_4$ alkoxy or 1 to 6 halogens; and
G is S.
Preferred Compounds C are Compounds B wherein:
$R_1$ is Cl, F, Br, $CF_3$, CN, $OCF_3$, $OCF_2H$, $OCF_2CF_2H$ or $SCF_2H$;
$R_2$ and $R_5$ are independently H, CL, F, Br, CN, $CF_3$, $CH_3$, $OCH(CH_3)_2$, $OCF_2H$, $OCF_3$, $SCH_3$, $SCF_2H$, $NO_2$ or $OCH_2CH_3$;
B is H, $CH_3$, $CH_2CH_3$, $CH(CH_3)_2$, $CO_2CH_3$, $CO_2CH_2CH_3$, phenyl or phenyl substituted with $(R_5)p$; and
$R_a$ is H or $CH_3$.
Preferred Compounds D are Compounds C wherein:
A is O or $CH_2$;
Preferred Compounds E are Compounds D wherein:
Q is Q-1;
Preferred Compounds F are Compounds D wherein:
Q is Q-2;
Preferred Compounds G are Compounds D wherein:
Q is Q-3;
Preferred Compounds H are Compounds D wherein:
Q is Q-4;
Preferred Compounds I are Compounds D wherein:
Q is Q-5;
Preferred Compounds J are Compounds D wherein:
Q is Q-6;
Preferred Compounds K are Compounds D wherein:
Q is Q-7;
Preferred Compounds L are Compounds D wherein:
Q is Q8;
Specifically preferred compounds are:
M) methyl 3,3a,4,5-tetrahydro-2-[[[4-trifluoromethyl)pheny]-amino]carbonyl]-2H-pyrazolo[3,4-f]-quinoline-3a-carboxylate, a compound of Preferred E;
N) methyl 3,3a,4,5-tetrahydro-2-[[[4-trifluoromethyl)phenyl]-amino]carbonyl]-2H-pyrazolo[4,3-h]-quinoline-3a-carboxylate, a compound of Preferred H;
O) methyl 7-chloro-3,3a,4,5-tetrahydro-N-[[[4-trifluoromethyl)phenyl]amino]carbonyl]-2H-thieno[2,3-g]-indazole-3a-carboxylate, a compound of Preferred I;
P) methyl 7-fluoro-3A,4-dihydro-2-[[[4-(trifluoromethyl)-phenyl]amino]carbonyl]-3H-pyrazolo[5,1-c]-[1,4]benzoxazine-3a-carboxylate, a compound of Preferred L; and
Q) 7-chloro-3A-(4-fluorophenyl)-3A,4-dihydro-N-[4-(trifluoromethyl)phenyl]-3H-pyrazolo[5,1-c][1,4]-benzoxazine-2carboxamide, a compound of Preferred L.

Hereafter, in the specification and claims, the various geometric isomers, stereoisomers and agriculturally suitable salts of each and every compound of the invention depending on context, is/are included in the term "compound(s)."

DETAILS OF THE INVENTION

For descriptive purposes, Q-1, where $R_a$ is H, will be used as a representative value of Q, when Q is Q-1 through Q-7, in the discussion that follows and will be referred to by the following numbering system:

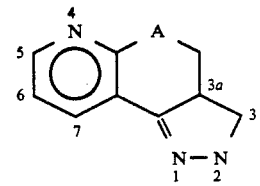

Compounds of Formula I can be prepared by the reaction of aryl isocyanates of Formula II and substituted indazoles of Formula III as shown in Scheme I. Typical reactions involve the combination of equimolar amounts of II and III in conventional organic solvents including ether, tetrahydrofuran (THF), methylene chloride, chloroform and benzene. The reaction can be run at temperatures ranging from about $-20°$ C. to $100°$ C. with temperatures in the range of about $-10°$ to $30°$ C. generally preferred.

SCHEME 1

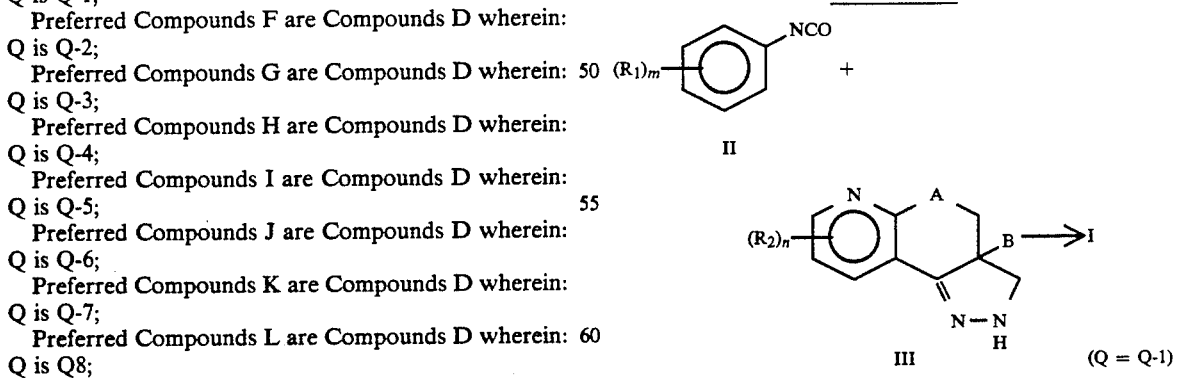

Substituted indazoles of Formula III, where B is equal to H, can be prepared by the reaction of hydrazine with an $\alpha$, $\beta$-unsaturated ketone of Formula IV (or their precursors) by procedures well documented in the chemical literature (Scheme 2). For a review of pyrazoline synthesis, see El-Rayyes and Al-Awadi, Synthesis, 1028 (1985). For literature describing the synthesis of 3,4- and 3,5-disubstituted pyrazolines, which can be applied to the synthesis of compounds of Formula III, where B is H, see U.S. Pat. No. 3,991,073 and U.S. Pat. No. 4,070,365.

SCHEME 2

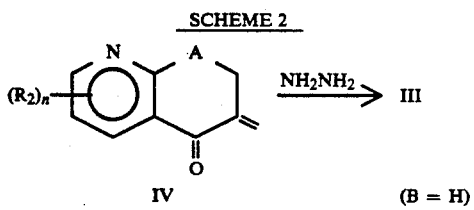

Preparation of compounds of Formula I, where B is other than H, OR7, phenyl or substituted phenyl can be achieved by metallation of the 3a position of Formula I (where B is H) followed by reaction with a suitable electrophile as depicted in Scheme 3. Procedures for the related transformation of 4-substituted pyrazolines to 4,4-disubstituted pyrazolines are reported in U.S. Pat. No. 4,663,341 and can be applied to the substituted indazoles of Formula I. Metallation can be accomplished by deprotonation with a strong base, in a suitable solvent and at temperatures ranging from −78° C. to 100° C. Useful bases for this reaction include lithium dialkylamides such as lithium diisopropylamide and lithium tetramethylpiperidide and alkyl lithium reagents such as n-butyllithium and s-butyllithium. Deprotonation of compounds of Formula I, where B is equal to hydrogen, will require two equivalents of base when Y is equal to hydrogen. The reaction can be conducted in many conventional organic solvents and in certain instances a cosolvent may be useful. Suitable solvents include diethylether, tetrahydrofuran, tetrahydropyran, benzene and the like. Suitable electrophilic reagents for reaction with the metallated Formula I compounds include alkyl and substituted alkyl halides, alkyl chloroformates, acyl halides, isocyanates, dialkyl carbamoyl halides and related electrophiles which will be known to those skilled in the art.

SCHEME 3

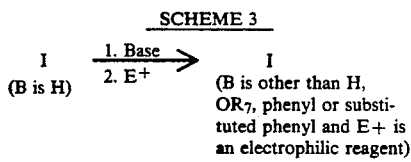

An alternative procedure for introduction of the 3a substituent, which in certain instances is preferred over that of Scheme 3 due to higher yields and/or greater ease of synthesis, proceeds via the intermediacy of Compound V, wherein the 2-nitrogen has been derivatized with a suitable protecting group. Deprotonation with a strong base such as lithium diisopropylamide, typically in stoichiometric quantities, followed by reaction with any of the previously described electrophiles provides compounds of Formula V where B is other than hydrogen, OR7, phenyl or substituted phenyl. Removal of the nitrogen protecting group provides the required Formula III intermediate. Nitrogen-protecting groups are well documented in the chemical literature, as are procedures for their preparation and cleavage. Examples include acetyl, trifluoroacetyl, benzoyl, substituted benzoyl, alkoxycarbonyl, benzyl and substituted benzyl. For a review see Greene "Protective Groups in Organic Synthesis" (New York: John Wiley and Sons, 1981) pp. 218 to 287.

SCHEME 4

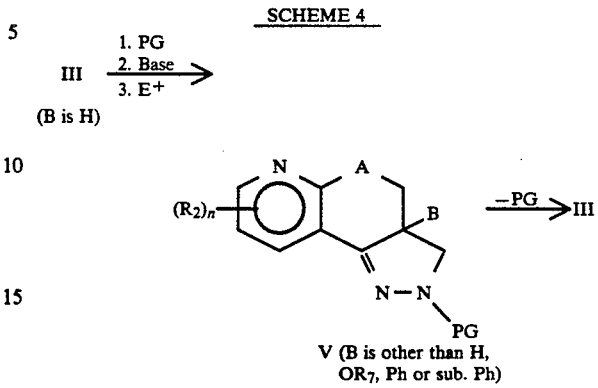

Note:
E+ is an electrophile and PG is representative of a suitable nitrogen-protecting group.

Formula III compounds where B is equal to hydroxy are prepared by the reaction of hydrazine with a suitably substituted epoxide of Formula VI (Scheme 5). The epoxides are available from the enones of Formula IV by procedures known in the art, the most widely employed method being epoxidation via the use of alkaline hydrogen peroxide (see, e.g., Wasson and House, Org. Syn., Coll. Vol. 4, 552 (1963)).

Compounds of Formula I where B is equal to OR7 and R7 is other than hydrogen, can be preferred from the Formula I compounds where B is equal to hydroxy via reaction with electrophilic reagents such as alkyl halides, acyl halides, alkyl chloroformates, chlorosulfonate, isocyanates and dialkyl carbamoylhalides. Those skilled in the art will recognize that conditions necessary for this transformation including solvent, catalyst, temperature, etc., will vary with the specific electrophile chosen and the specific Formula I compound used.

SCHEME 5

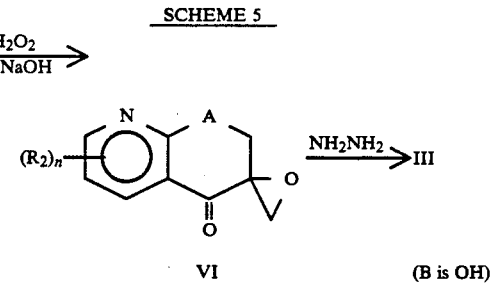

Compounds of Formula III where B is phenyl or substituted phenyl can be prepared by reaction of a ketone of Formula IX, where L is a suitable leaving group such as chloride, bromide, tosylate or mesylate, with hydrazine. The formula IX compounds are in turn prepared from the compounds of Formula VII in a two-step process involving first an aldol reaction of formaldehyde to produce the aldol product of Formula VIII followed by conversion of the hydroxyl group to a leaving group L. As an example, treatment of the Formula VIII compound with methanesulfonylchloride in the presence of an amine base produces the Formula IX compound where L is mesylate.

SCHEME 6

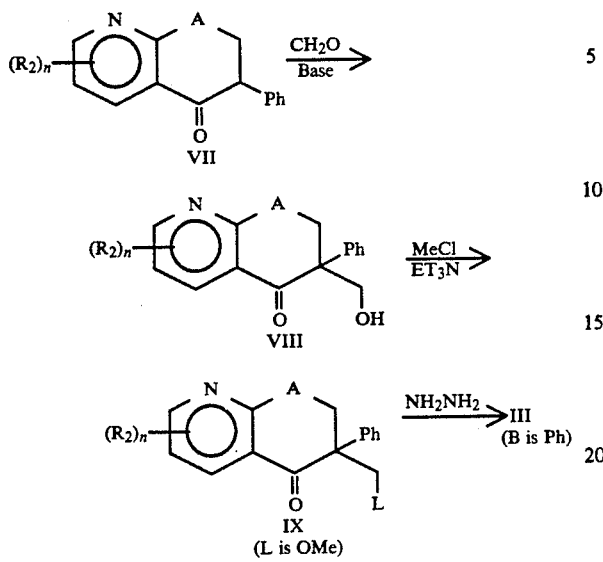

The α-methylene ketones of Formula IV can be prepared from the ketones of Formula X by a variety of procedures well documented in the literature. For example, treatment of X with tetramethyldiaminomethane and acetic anhydride produces the Formula IV compound directly. Another useful procedures is to treat the Formula X compound with formaldehyde under conditions of a Mannich reaction. The dialkylamino group can be eliminated in situ upon treatment with base to form the intermediate of Formula IV.

SCHEME 7

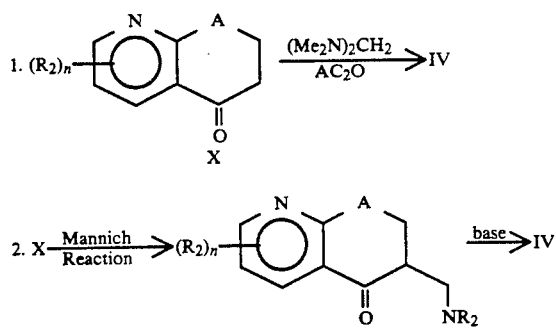

Those skilled int he art will recognize the intermediates of Formula X as substituted quinolones. Isoquinolones and the isomer benzothiophenones used for preparation of compounds of Formula I, where Q is Q-2 through Q-7, are also known in the chemical literature as are procedures for their preparation. A few selected references include: where Q is Q-1 see *J. Chem. Soc., Perkin I*, 975 (1976), where Q is Q-2 see *J. Amer. Chem. Soc.*, 107, 4998 (1985), where Q is Q-3 see *J. Org. Chem.* 43, 966 (1978), where Q is Q-4 see *J. Het. Chem.* 15, 249 (1978), when Q is Q-5 or Q-7 see *Tetrahedron Letters*, 2885 (1975) or *J. Heterocyclic Chem.*, 17, 87 (1980), and where Q is Q-6 see *Bull. Soc. Chim. Fr.*, 335 (1973).

An alternative method for preparing compounds of Formula I, where Q is Q-1 through Q-7, involves intramolecular cyclization of hydrazone XI or produce the N-phosphorylated dihydropyrazole XII. The phosphorus group can then be removed under acidic conditions and neutralized with base to yield the substituted indazoles of Formula III.

SCHEME 8

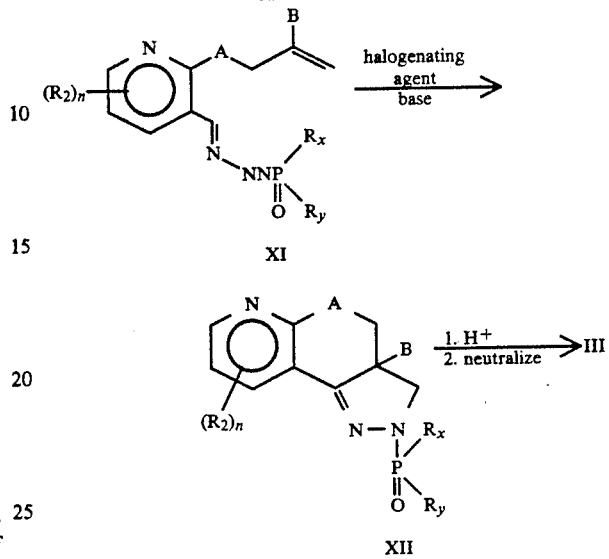

wherein: $R_x$ and $R_y$ are independently selected from $C_1$ to $C_4$ alkyl and $C_1$ to $C_4$ alkoxy.

The intramolecular cyclization can be conducted by gradual addition of a moderately reactive halogenating agent such as N-chlorosuccinimide to a mixture of a base, such as triethylamine, and the compound of Formula XI in a dry inert solvent such as ether, dichloromethane or toluene. Alternatively, when Q is Q-5, Q-6 or Q-7, the base can be added gradually to a mixture of the halogenating agent and compound XI. It is preferable that the concentration of reactant be kept relatively low (0.01 to 0.5 M) and that the compound being added to the reaction mixture is added gradually to avoid competing side reactions which occur at higher concentrations. For optimum yields, it is also important to maintain anhydrous conditions.

Hydrolysis of the phosphorus group is best accomplished by treatment of XII with 1 t 5 equivalents of a strong acid such as hydrochloric, sulfuric or p-toluenesulfonic in a suitable solvent such as methanol, ethanol or tetrahydrofuran, optionally containing about 0.1 to 10 equivalents of water. The reaction can be conducted at temperatures generally ranging from about 20° to 100° C. with the reflux temperature of the solvent being generally preferred. Once the reaction is complete, the acid salt can be precipitated by cooling to 0° C., or if it does not precipitate, the solvent can be removed and ether added to facilitate crystallization. The acid salt of III can then be neutralized with an inorganic base such as sodium carbonate or sodium bicarbonate to give the free base III. In some instances, it is preferable to convert the acid salt of III directly to compounds of Formula I by addition of an aqueous solution of an inorganic base to a suspension of the salt III in an organic solvent such as tetrahydrofuran, followed by addition of the isocyanate II.

Compounds of Formula XI are prepared by condensation of an aldehyde of Formula XIII with a phosphorus hydrazid of Formula XIV.

SCHEME 9

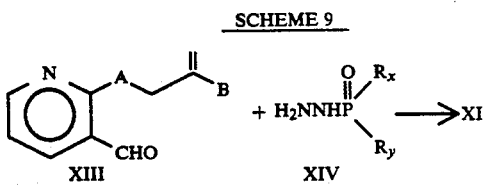

This reaction is typically run in an inert organic solvent. Alcohol solvents such as methanol and ethanol and ether solvent such as tetrahydrofuran and diethyl ether are generally preferred. The reaction can also be conducted with a catalytic amount of acid such as p-toluenesulfonic acid although typically acid catalysis is not necessary. The products of Formula XI generally precipitate from the reaction mixture as they are formed.

Starting materials of Formula XIII and XIV can be prepared by analogy with procedures known in the art.

Compounds of Formula I, where Q is Q-8, can be obtained by the reaction of activated carbonyl or thiocarbonyl compounds of Formula II with substituted anilines in the presence or absence of an acid acceptor or suitable condensing agent. Methods for performing this transformation as well known in the art; see, Zabicky, "The Chemistry of the Amides", Interscience, 1970.

One particularly useful method involves the chlorination of an acid derivative (XV, $X_1$=OH) with thionyl chloride or another chlorinating agent followed by treatment with an aniline (XVI) in the presence of an acid acceptor such as an amine base, preferably triethylamine. Suitable solvents for the chlorination reaction are inert to hydrogen chloride and include benzene, toluene, and dichloromethane. Preferred temperatures for this process are from 20° to 100° C. with temperatures between 20° and 80° C. being particularly preferred. The latter reaction can be carried out in many different inert solvents such as dialkylethers, chlorinated hydrocarbons, and aromatic hydrocarbons. While temperatures at or below 25° C. are preferred, higher temperatures can also be employed. These reactions are normally run at atmospheric pressure, but can also be carried out at elevated pressures.

SCHEME 10

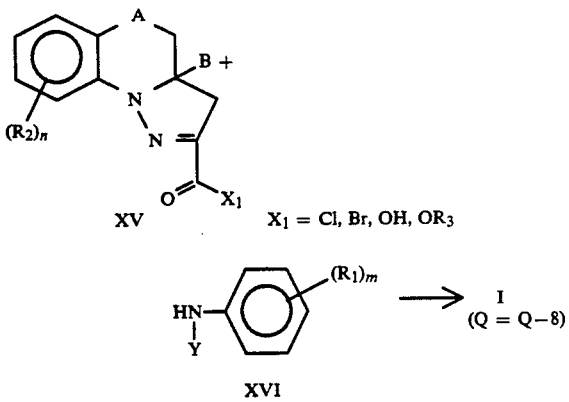

Esters of Formula XV ($X_1$=$C_1$ to $C_6$ alkoxy) can be converted directly to compounds of Formula I (Q=Q-8) in several ways. In the presence of Lewis acids such as $AlMe_3$, anilines react readily with esters of Formula XV. The reaction is best carried out at room temperature to 120° C. Suitable solvents include dichloromethane, 1,2-dichloroethane, and toluene. The method described by Weinreb et al., Organic Synthesis, 59, 49, (1982), proceeds best with esters of lower alcohols such as methanol and ethanol.

Acids of Formula XV ($X_1$=OH) can be converted directly to compounds of Formula I by use of coupling agents known in the peptide art in conjunction with anilines. Coupling agents include dicyclohexylcarbodiimide (DCC), N-hydroxysuccinimide, 2-chloro-N-methylpyridinium iodide, carbonyl diimidazole, or other agents capable of activating an acid function or acting as a dehydrating agent. These and other methods are described in Gross et al., "The Peptides," 3 Vols., Academic Press, New York, 1979 to 1981.

Compounds of Formula I (Q=Q-8) and intermediates of Formula XV can also be obtained by the intramolecular dipolar cycloaddition reaction of nitrile-imines, generated from substituted phenylhydrazones of Formula XVII (Scheme 11). The presence of an acid acceptor (generally an amine base, for example, triethylamine) is necessary for the formation of the nitrile-imine. Suitable solvents include but are not restricted to benzene, toluene, 1,2-dichloroethane, chloroform, and tetrahydrofuran. The reaction can be carried out at temperatures ranging from 20° to 120° C. with the relative reactivity of the alkene moiety governing the required temperature for a given example.

SCHEME 11

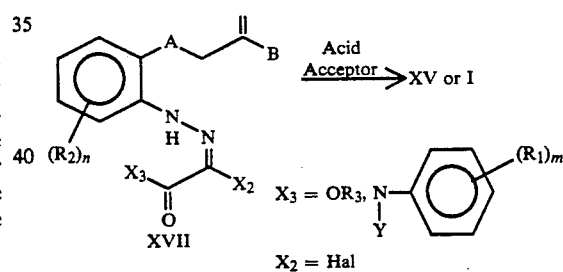

The required hydrazones of Formula XVII can be synthesized by the Japp-Klingemann reaction (Scheme 12). The coupling of diazonium salts with active methylene compounds is known. The more specific coupling of chloroacetoacetic acid derivatives of Formula XVIII with diazotized anilines of Formula XVIV containing alkenyl substituents is described by Padwa et al. in J. Org. Chem., 43, 1664 (1978) and J. Org. Chem., 46, 1402 (1981). A similar process for this type of aniline is described by Garanti et al. in J. Org. Chem., 42, 1389 (1977), and J. Chem. Soc. Perkin I, 2245 (1981).

SCHEME 12

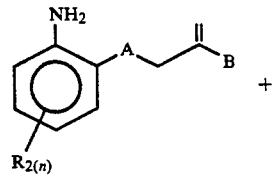

-continued
SCHEME 12

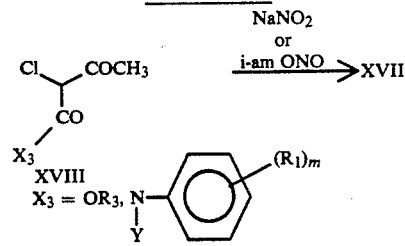

The anilines of Formula XVIV can be obtained by the reduction of aromatic nitro compounds of Formula XX (Scheme 13). There are many methods known for this transformation. See, March, "Advanced Organic Chemistry", 1985, Wiley, page 1103-1104. A particularly suitable method involves the treatment of the nitro compound with tin (II) chloride in alcoholic solvents. Refer to Bellamy et al. *Tetrahedron Letters*, 1984, 839.

SCHEME 13

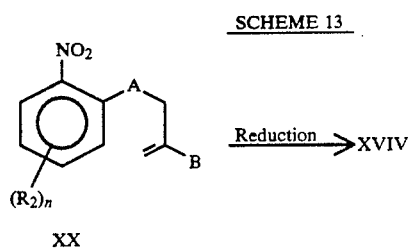

Nitro compounds of Formula XX containing a heteroatom in the alkenyl chain can be obtained by alkylation reactions (Scheme 14). Treatment of a substituted phenol, thiophenol, or aniline or Formula XXI with an acid acceptor and an alkyl or homoallyl halide or sulfonate of Formula XXII gives compounds of Formula XX as products. Preferred acid acceptors for the process are inorganic bases such as potassium carbonate. Preferred solvents include dimethylformamide, dimethylsulfoxide, methylethyl ketone, and ethanol. The reaction is generally carried out at room temperature, but higher temperatures may be necessary in some cases. Alternative methods for these nitro compounds of Formula XX have been described by Oae et al. in *Bull. Chem. Jap.*, 54, 2374 (1981).

SCHEME 14

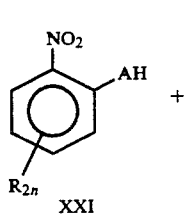

Anilines of Formula XVIV containing sulfur can be obtained by alkylation on the sulfur of Formula XXIII (Scheme 15). The conditions which favor this process are alcoholic solvents and sodium hydroxide or sodium alkoxides as bases. The reaction is generally carried out using a allylic halides of Formula XXII at 20° to 80° C. in lower alcoholic solvents, preferably ethanol.

SCHEME 15

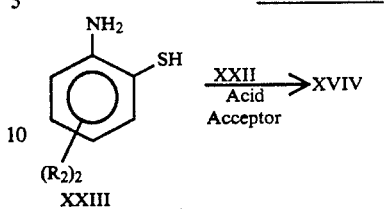

Anilines of Formula XVIV which do not contain a heteroatom in the alkenyl portion can be synthesized by the Claisen rearrangement (Scheme 16). The thermal and acid catalyzed rearrangement of N-allylanilines of Formula XXIV has been described by Hansen et al. in *Helv. Chim. Acta.*, 60, 978 (1977).

SCHEME 16

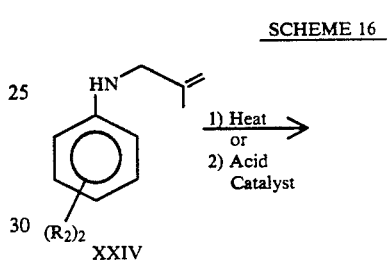

The hydrazonyl halides of Formula XVII (A=S, q—1 or 2) in which a sulfoxide or sulfone are present may be obtained by the oxidation of the corresponding sulfide of Formula XVII (A=S, q=O) (Scheme 17). Oxidation of hydrazones of Formula XVII (A=S), q=O) by hydrogen peroxide in acetic acid is known. See Zecchi et al., *J. Chem. Res.* 1887 (1986). By modifications of the amount of oxidant, reaction time and temperature the product obtained can be specifically the sulfoxide of Formula XVII (A=S, q—1) or the sulfone of Formula XVII (A=S, q=2).

SCHEME 17

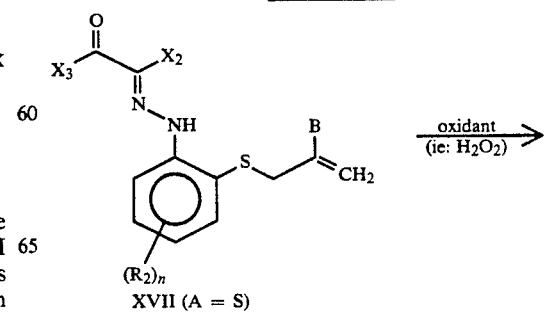

-continued
SCHEME 17

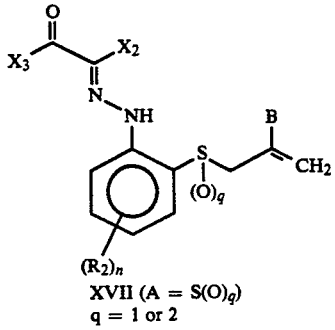

XVII (A = S(O)$_q$)
q = 1 or 2

Cycloaddition of the hydrazones of Formula XVII (A=S, q=0) proceeds only in low yield. Synthesis of sulfur containing compounds XV (A=S, q=0) can be accomplished by reducing the sulfoxides of Formula XV (A=S, q=1) (Scheme 18). Many reagents are known in the art to reduce sulfoxides. See March, "Advanced Organic Chemistry", 1985, Wiley, page 1108. One particularly useful method uses titanium (III) chloride at room temperature and was described by Ho in *Synthetic Comm.*, 3, 37 (1973).

SCHEME 18

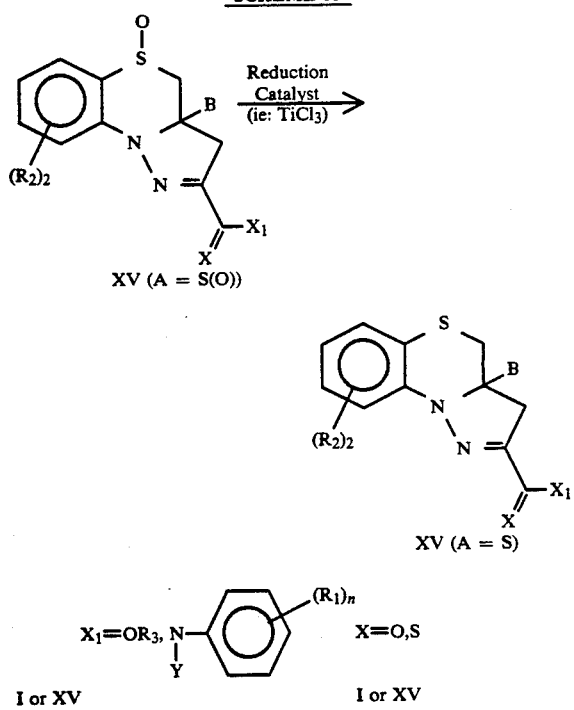

Compounds of Formula I, where Y is H and Q is Q-1 through Q-8, can be converted to other compounds of Formula I by alkylation, acylation, and sulphenylation reactions to form derivatives where Y is other than H. Reaction of compounds of Formula I in the presence of an acid acceptor with electrophilic agents results in substitution on nitrogen. Strong bases such as sodium hydride, potassium t-butoxide, potassium hydride, and other bases known in the art to deprotonate amides are preferred in the process. Suitable electrophiles include, but are not restricted to alkyl halides, acyl halides, acid anhydrides, carbonates, chloroformate, disulphides, and sulphenyl halides. This reaction is normally run in the temperature range of 0°–25° C., but can be run at temperature up to 120° C. if unreactive electrophiles are used. Solvents not deprotonated under the reactions conditions such as tetrahydrofuran, dimethylformamide, dimethoxyethane, and diethyl ether are preferred.

Compounds of Formula I (X=O) can be converted to compounds of Formula I (X=S) by means of thiating agents. Conversion of amides to thioamides is well known in the art. Phosphorous pentasulfide either alone or in combination with organic or inorganic bases is a preferred reagent to effect this conversion. When phosphorous pentasulfide is used alone, organic bases such as pyridine are the preferred solvents. When it is used in conjunction with inorganic bases such as sodium bicarbonate, the preferred solvents are ethers such as diglyme. Temperatures between 20° to 160° C. can be employed successfully with temperatures between 90° to 120° C. preferred. These and other means to convert amides to thioamides are described by Lapucha, *Synthesis*, 256 (1987).

The following Examples further illustrate the invention.

EXAMPLE 1

3,3A,4,5-tetrahydro-N-[4-(trifluoromethyl)phenyl]-2H-thieno[2,3-g]indazole-2-carboxamide

Step A:
6,7-Dihydro-5-methylenebenzo[b]thiophen-4(5H)-one

To 20.0 mL of tetramethyldiaminomethane was added 10.0 g of 6,7-dihydrobenzo[b]thiophen-4(5H)-one all at once. To this mixture was added 20.0 mL of acetic anhydride, dropwise. The reaction mixture exothermed to 45° C. and was heated to 122° C. for 15 minutes and then cooled to 90° C. where it was kept for 60 minutes. The dark solution was poured into cold water and extracted with ether. The ether was extracted with a saturated solution of NaHCO$_3$ and then washed with brine. The ether layer was dried over anhydrous magnesium sulfate, filtered and concentrated in vacuo to afford a yellow oil. The yellow oil was flash-chromatographed using 10% ethyl acetate and 90% hexanes as eluent to afford 6.18 g of a white solid, m.p. 47°–49° C. 200 MHz$^1$H NMR(CDCl$_3$) δ2.97 (t, 2H), 3.07 (t, 2H), 5.46 (s, 1H), 6.17 (s,1H), 7.11 (d, 1H), 7.48 (d, 1H); I. R. (Nugol) 1660 cm$^{-1}$.

Step B: 3,3a,4,5-tetrahydro-2H-thieno[2,3-g]indazole

To 20 mL of anhydrous ethanol was added 1.2 g of the product from Step A and 0.40 g of hydrazine hydrate. The reaction mixture was heated at reflux for 2 h, cooled, poured into cold water and extracted with ether. The ether extracts were washed with water and brine, dried over anhydrous magnesium sulfate, filtered and utilized without concentration or purification in Step C.

Step C

Preparation of title compound was as follows. To a 150 mL solution of the product from Step B in ether was added 1.50 g of α,α,α-terifluoro-p-tolylisocyanate. The reaction mixture was stirred at room temperature for 1 hr. where a precipitate was formed. The reaction mixture was filtered and the precipitate was washed with ether to afford 0.20 g of a white solid, m.p. 219°–221° C. 200 MHz$^1$H NMR(CDCl$_3$) δ1.98 (bm, 1H), 2.48 (bm, 1H), 3.10 (m, 2H), 3.42 (m, 2H), 4.43 (m, 1H), 7.25 (d, 1H), 7.36 (d, 1H), 7.56 (d, 2H), 7.67 (d,2H), 8.18 (bs, 1H); I.R. (Nujol) 3370,1668 cm$^{-1}$.

EXAMPLE 2

7-Chloro-3a,4,-dihydro-3a-phenyl-N-[4-(trifluoromethyl)phenyl)-3H-pyrazolo[5,1-c][1,4]benzoxazine-2-carboxamide

Step A:
4-chloro-1-nitro-2-(phenyl-2-propenyloxy)benzene

A solution of 5-chloro-2-nitrophenol (7 g) in dimethylformamide (40 ml) was stirred at room temperature with 1-bromo-2-phenyl-2-propene (8 ml) and potassium carbonate (5.5 g) for 18 h. The reaction mixture was diluted with water (200 ml) was extracted with ether (100 ml). The ether was washed with water (3×100 ml). The solvent was removed under reduced pressure and the residue was crystallized from hexanes. The yellow solid (8.6 g) was the desired product. m.p. 74.5°–75.5° C.

NMR (200 MHz) CDCl$_3$; δ7.8 (d, 1H,ArH), 7.4–7.0 (m, 7H, ArH), 5.6 (S,S, 2H, CH$_2$), 5.0 (S, 2H, CH$_2$O).

Step B:
4-chloro-2-[(2-phenyl-2-propenyl)oxyl]benzenamine

The compound of Step A (7.2 g) was added to a suspension of tin (II) chloride (28 g) in ethanol (45 ml). The mixture was refluxed for 1.5 h. The reaction was diluted with ethyl acetate and neutralized by careful addition of saturated sodium bicarbonate solution. The organic solution was washed with brine and the solvent was dried over magnesium sulfate. Evaporation of the solution left a thick oil of the title compound (5.8 g).

NMR (200 MHz) CDCl$_3$ δ7.4–6.6 (m, 8H, ArH), 5.6–5.4 (S,S, 2H, CH$_2$), 4.9 (S, 2H, CH$_2$O), 3.2 (Br, NH$_2$).

Step C: methyl chloro [[4-chloro-2[(2-phenyl-2-propenyl)oxy]phenyl]hydrazono]acetate Using the procedure of Example 4 (Step B), the compound of Step B (5.6 g) was converted to the title compound (2.8 g). The chromatography was carried out with hexanes/ethyl acetate (8:1); m.p. 88°–90° C.

NMR (200 MHz) CDCl$_3$ δ8.6 (br. s, NH$_2$), 7.3–6.9 (m, 8H, ArH), 5.7–5.6 (m, 2H, CH$_2$), 4.9 (s, 2H, CH$_2$O).

Step D: methyl 7-chloro-3a-4-dihydro-3a-phenyl-3H-pyrazolo[5,1-c[]1,4]benzoxazine-2-carboxylate The compound of Step C (2.5 g) was dissolved in benzene (100 ml), treated with triethylamine (5 ml), and heated at reflux for 24 h. The cooled mixture was diluted with ethyl acetate (100 ml) and 1N HCL (100 ml). The organic layer was dried and evaporated. The residue was chromatographed on silica gel with hexane/ethyl acetate (5:1). The title compound (1 g) was a solid. m.p. 145°–146° C.

NMR (200 MHz) CDCl$_3$ δ7.6–6.8 (m, 8H, ArH), 4.65 (d, 1H, CH), 3.9 (d, 1H, CH), 3.8 (S, 3H, CH$_3$), 3.4 (m, 2H, CH$_2$).

Step E

Preparation of title compound was as follows. The compound of Step D (1.0 g) was suspended in methanol (10 ml) and treated with 50% aqueous sodium hydroxide (1 ml) and heated to reflux for 10 min. The mixture was acidified and extracted with ethyl acetate. The dried organic extract was evaporated. The residue was dissolved in benzene (15 ml) and treated with thionyl chloride (1.5 ml). The mixture was heated to reflux for 2H and then evaporated. The residue was dissolved in tetrahydrofuran (20 ml) and one half was added to a solution of p-trifluoromethoxyaniline (0.4 g) and triethylamine (1.0 ml) in tetrahydrofuran (10 ml). After stirring for 1h the mixture was partitioned between ethyl acetate (50 ml) and 1N HCl (50 ml). The dried organic layer was evaporated. Chromatography of the residue on silica gel in hexanes/ethyl acetate (7:1) gave the title compound (0.39 g). m.p. 140°–146° C.

NMR (200 MHz) CDCl$_3$ δ8.6 (br, NH), 7.8–6.9 (m, 12H, ArH), 4.7 (d, 1H, CH), 3.8 (d, 1H, CH), 3.4 (dd, 2H, CH$_2$).

EXAMPLE 3

Methyl 7-fluoro-3a,4-dihydro-2-[[[4-(trifluoromethyl)phenyl]amino]carbonyl]-3H-pyrazolo[5,1-c]-[1,4]benzoxazine-3a-carboxylate

Step A: methyl 2-[(5-fluoro-2-nitrophenoxy)methyl]-2-propenoate

The compounds 5-fluoro-2-nitrophenol (8.0 g), methyl 2-bromomethylacrylate (9.5 g) and potassium carbonate (7 g) under the conditions of Example 2, (Step A) gave the title compound (11.6 g). m.p. 89°–92° C.

NMR (200 MHz) CDCl$_3$ δ8.0 (m, 1H, ArH), 6.9 (m,2H, ArH), 6.4–6.2 (S,S, 2H, CH$_2$), 4.8 (S, 2H, CH$_2$O), 3.8 (S, 3H, CH$_3$O).

Step B: methyl 2-[(2-amino-5-fluorophenoxy)methyl]-2-propenoate

The compound of Step A (11.0 g) was converted to the title compound (8 g) by the method of the Example 2 (Step B).

NMR (200 MHz) CDCl$_3$ δ6.8 (m, 3H, ArH), 6.5 & 6.0 (S, S, 2H, CH$_2$), 4.8 (S, 2H, CH$_2$O), 4.2 (Br, NH$_2$), 3.8 (S, 3H, CH$_3$O).

Step C: methyl 2-[[2-[2-(1-chloro-2-methoxy-2-oxo-ethylidene)hydrazino]-5-fluorophenoxy]methyl]-2-propenoate Using the procedure of Example 4 (Step C) the title compound (2.1 g) was prepared from the compound of Step B (7.5 g).

NMR (200 MHz) CDCl$_3$ δ8.7 (br. s, NH), 7.6 (m, 1H, ArH), 6.9 (m, 2H, ArH), 6.5 (S, 1H, CH$_2$), 6.0 (S, 1H, CH$_2$), 4.8 (S, 2H, CH$_2$), 3.8 (S, 6H, 2OCH$_3$).

Step D

Preparation of title compound (0.13 g) was as follows. The procedure of Example 2 (Steps D and E) were used with the compound of Step C (1.8 g) and the p-trifluoromethoxyaniline was replaced with p-trifluoromethyl-aniline. m.p. 177.5°–181° C.

NMR (200 MHz) CDCl$_3$ δ8.6 (br, NH), 7.7–6.8 (m, 7H, ArH), 4.7 (d, 1H, CH$_2$O), 3.8 (S, 3H, CH$_3$O), 3.8–3.4 (m, 3H, CH$_2$, CH$_2$O).

EXAMPLE 4

Methyl 3a,4-dihydro-3a-phenyl-3H-pyrazolo[5,1-c[]1,4]benzothiazine-2-carboxylate-5-oxide

Step A: 2-[(2-phenyl-2-propenyl)thio]benzenamine

The compound, 2-aminothiophenol, (12.5 g) was added to a solution of sodium hydroxide (4.5 g) in ethanol (100 ml) keeping the temperature less than 30° C. Then 1-bromo-2phenyl-2-propene (21 g) was added and the mixture was stirred at 60° C. for 3 h. The precipitated solid was filtered and washed with ethanol. The solvent was removed and the residue was chromatographed on silica gel with hexanes/ethyl acetate (7:1) to yield the title compound (14.5 g). As an oil.

NMR (200 MHz) CDCl$_3$ $\delta$7.3–7.0 (m, 9H, ArH), 5.3–5.0 (m, 2H, CH$_2$), 4.0 (Br, NH$_2$), 3.8 (S, 2H, CH$_2$S).

Step B: methyl chloro[[2-[(2-phenyl-2-propenyl)thio]-phenyl]hydrazono]acetate The compound of Step A (14.5 g) was treated with 6N HCl (22 ml) and water (100 ml). This mixture was cooled to below 0° C. and treated dropwise with an aqueous solution of sodium nitrite (4.2 g). The resulting mixture was decanted into an insulated dropping funnel. The mixture was added to a cooled (−5° to −10° C.) mixture of sodium acetate (15 g) and methyl 2-chloroacetoacetate (5 ml) in ethanol (100 ml) so that the internal temperature did not exceed 5° C. The mixture was allowed to come to room temperature over 2 h and then extracted with ether. The dried organic layer was evaporated and chromatographed on silica el with ether/hexanes (1:2). The title compound (11.5 g) was isolated as a yellow oil. NMR (200 MHz) CDCl$_3$ $\delta$9.4 (br, NH) 7.5–7.0 (m, 9H, ArH), 5.2 (S, 1H, CH$_2$), 4.8 (S, 1H, CH$_2$), 3.9 (S, 3H, CH$_3$), 3.8 (S, 2H, CH$_2$S).

Step C: methyl chloro[[2-[(2-phenyl-2-propenyl)sulfinyl]phenyl]-hydrazono]acetate The compound of Step B (5 g) was stirred with occasional warming in acetic acid (45 ml) and treated with 30% aqueous hydrogen peroxide (2.0 ml). After stirring for 5 h, water (200 ml) was added and the P.h. was adjusted to 6 with sodium bicarbonate. Saturated sodium bisulfite solution (3 ml) was added and the mixture was extracted with dichloromethane (200 ml). The organic layer was dried and evaporated to give the title compound (4.9 g).

NMR (200 MHz) CDCl$_3$ $\delta$7.6–7.0 (m, 9H, ArH), 5.6–4.2 (m, 4H, CH$_2$), 4.0 (S, 3H, CH$_3$O).

Step D

Preparation of title compound (1.0 g) was as follows. The method of Example 2 (Step D) was applied to the compound of Example 12 (4.5 g). Purification was accomplished by chromatography on silica gel with hexanes/ethyl acetate (1:1).

NMR (200 MHz) CDCl$_3$ $\delta$7.3–7.0 (m, 9H, ArH), 4.2 (dd, 1H, CH$_2$), 3.9 (S, CH$_3$O, 3H), 3.6 (m, 3H, CH$_2$).

EXAMPLE 5

3a,4-Dihydro-3a-phenyl-N-[4-(trifluoromethyl)phenyl]-3H-pyrazolo[5,1-c]benzothiazine-2-carboxamide The compound of Example 4 (Step D) (1 g) was treated with 20% aqueous titanium (III) chloride (2 ml) in dichloromethane (20 ml) and methanol (20 ml). The mixture was stirred for 20 min. at room temperature and partitioned between ethyl acetate (150 ml) and water (200 ml). The dried organic phase was concentrated and the residue was subjected to the conditions of Example 10 with p-trifluoromethylaniline in place of p-trifluoromethoxyaniline. The title compound (0.6 g) was isolated as a solid. m.p. 238°–240° C.

NMR (200 MHz) CDCl$_3$ $\delta$8.6 (br, NH), 7.8–6.9 (m, 13H, ArH), 3.6 (S, 2H, CH$_2$), 3.4 (S, 2H, CH$_2$).

By the general procedures described herein, or obvious modifications thereof, the compounds of Tables 1through 16 can be prepared.

| SUMMARY OF TABLES | | | |
|---|---|---|---|
| Table | Q | Y | G |
| 1 | Q-1 | H | — |
| 2 | Q-2 | H | — |
| 3 | Q-3 | H | — |
| 4 | Q-4 | H | — |
| 5 | Q-5 | H | S |
| 6 | Q-6 | H | S |
| 7 | Q-7 | H | S |
| 8 | Q-5 | H | O |
| 9 | Q-6 | H | O |
| 10 | Q-7 | H | O |
| Table 11 | R$_a$ is H, X is O, G is S | | |
| Table 12 | R$_a$ is H, X is O, G is S, Y is S—J | | |
| Table 13 | Q is Q-8, R$_a$ is H, Y is H, A is CH$_2$ | | |
| Table 14 | Q is Q-8, R$_a$ is H, Y is H | | |
| Table 15 | Q is Q-8, R$_a$ is H | | |
| Table 16 | Q is Q-8, Y is H | | |

In the Tables that follow, the values of Q will be referred to by the following numbering system:

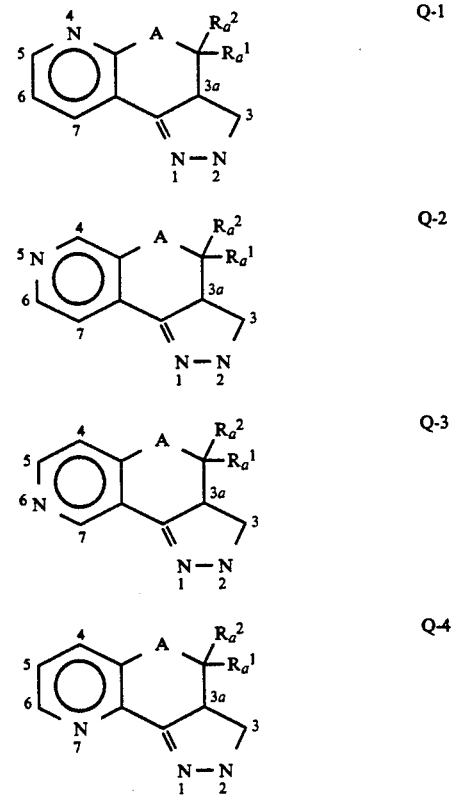

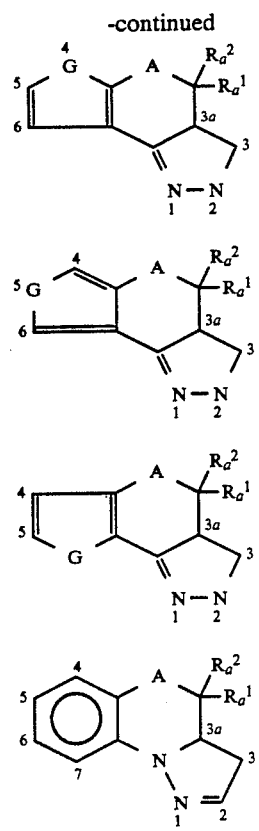

Q-5

Q-6

Q-7

Q-8

TABLE 1

| R₁ | R₂ | A | B | X | $R_a^1$, $R_a^2$ |
|---|---|---|---|---|---|
| 4-CF₃ | H | CH₂ | H | O | H, H |
| 4-Cl | H | CH₂ | H | O | H, H |
| 4-Br | H | CH₂ | H | O | H, H |
| 4-CF₃ | 5-Cl | CH₂ | H | O | H, H |
| 4-Cl | 5-Cl | CH₂ | H | O | H, H |
| 4-Br | 5-Cl | CH₂ | H | O | H, H |
| 4-CF₃ | 5-F | CH₂ | H | O | H, H |
| 4-Cl | 5-F | CH₂ | H | O | H, H |
| 4-Br | 5-F | CH₂ | H | O | H, H |
| 4-CF₃ | 5-CN | CH₂ | H | O | H, H |
| 4-Cl | 5-CN | CH₂ | H | O | H, H |
| 4-Br | 5-CN | CH₂ | H | O | H, H |
| 4-CF₃ | 5-Br | CH₂ | H | O | H, H |
| 4-Cl | 5-Br | CH₂ | H | O | H, H |
| 4-Br | 5-Br | CH₂ | H | O | H, H |
| 4-CF₃ | 5-Me | CH₂ | H | O | H, H |
| 4-Cl | 5-Me | CH₂ | H | O | H, H |
| 4-Br | 5-Me | CH₂ | H | O | H, H |
| 4-CF₃ | 7-F | CH₂ | H | O | H, H |
| 4-Cl | 7-F | CH₂ | H | O | H, H |
| 4-Br | 7-F | CH₂ | H | O | H, H |
| 4-CF₃ | 5-NMe₂ | CH₂ | H | O | H, H |
| 4-Cl | 5-NMe₂ | CH₂ | H | O | H, H |
| 4-Br | 5-NMe₂ | CH₂ | H | O | H, H |
| 4-CF₃ | 5-CF₃ | CH₂ | H | O | H, H |
| 4-Cl | 5-CF₃ | CH₂ | H | O | H, H |
| 4-Br | 5-CF₃ | CH₂ | H | O | H, H |
| 4-CF₃ | H | CH₂ | Me | O | H, H |
| 4-Cl | H | CH₂ | Me | O | H, H |
| 4-Br | H | CH₂ | Me | O | H, H |
| 4-CF₃ | 5-Cl | CH₂ | Me | O | H, H |
| 4-Cl | 5-Cl | CH₂ | Me | O | H, H |
| 4-Br | 5-Cl | CH₂ | Me | O | H, H |
| 4-CF₃ | 5-CF₃ | CH₂ | Me | O | H, H |
| 4-Cl | 5-CF₃ | CH₂ | Me | O | H, H |
| 4-Br | 5-CF₃ | CH₂ | Me | O | H, H |
| 4-CF₃ | H | CH₂ | Et | O | H, H |
| 4-Cl | H | CH₂ | Et | O | H, H |
| 4-Br | H | CH₂ | Et | O | H, H |
| 4-CF₃ | 5-F | CH₂ | Et | O | H, H |
| 4-Cl | 5-F | CH₂ | Et | O | H, H |
| 4-Br | 5-F | CH₂ | Et | O | H, H |
| 4-CF₃ | 5-CN | CH₂ | Et | O | H, H |
| 4-Cl | 5-CN | CH₂ | Et | O | H, H |
| 4-Br | 5-CN | CH₂ | Et | O | H, H |
| 4-CF₃ | H | CH₂ | allyl | O | H, H |
| 4-Cl | H | CH₂ | allyl | O | H, H |
| 4-Br | H | CH₂ | allyl | O | H, H |
| 4-CF₃ | 5-Br | CH₂ | allyl | O | H, H |
| 4-Cl | 5-Br | CH₂ | allyl | O | H, H |
| 4-Br | 5-Br | CH₂ | allyl | O | H, H |
| 4-CF₃ | 5-Cl | CH₂ | allyl | O | H, H |
| 4-Cl | 5-Cl | CH₂ | allyl | O | H, H |
| 4-Br | 5-Cl | CH₂ | allyl | O | H, H |
| 4-CF₃ | H | CH₂ | CO₂Me | O | H, H |
| 4-Cl | H | CH₂ | CO₂Me | O | H, H |
| 4-Br | H | CH₂ | CO₂Me | O | H, H |
| 4-CF₃ | 5-F | CH₂ | CO₂Me | O | H, H |
| 4-Cl | 5-F | CH₂ | CO₂Me | O | H, H |
| 4-Br | 5-F | CH₂ | CO₂Me | O | H, H |
| 4-CF₃ | 5-Cl | CH₂ | CO₂Me | O | H, H |
| 4-Cl | 5-Cl | CH₂ | CO₂Me | O | H, H |
| 4-Br | 5-Cl | CH₂ | CO₂Me | O | H, H |
| 4-CF₃ | 5-Br | CH₂ | CO₂Me | O | H, H |
| 4-Cl | 5-Br | CH₂ | CO₂Me | O | H, H |
| 4-Br | 5-Br | CH₂ | CO₂Me | O | H, H |
| 4-CF₃ | 5-CN | CH₂ | CO₂Me | O | H, H |
| 4-Cl | 5-CN | CH₂ | CO₂Me | O | H, H |
| 4-Br | 5-CN | CH₂ | CO₂Me | O | H, H |
| 4-CF₃ | 5-CF₃ | CH₂ | CO₂Me | O | H, H |
| 4-Cl | 5-CF₃ | CH₂ | CO₂Me | O | H, H |
| 4-Br | 5-CF₃ | CH₂ | CO₂Me | O | H, H |
| 4-CF₃ | 5-Me | CH₂ | CO₂Me | O | H, H |
| 4-Cl | 5-Me | CH₂ | CO₂Me | O | H, H |
| 4-Br | 5-Me | CH₂ | CO₂Me | O | H, H |
| 4-CF₃ | H | CH₂ | CO₂Et | O | H, H |
| 4-Cl | H | CH₂ | CO₂Et | O | H, H |
| 4-Br | H | CH₂ | CO₂Et | O | H, H |
| 4-CF₃ | 5-Cl | CH₂ | CO₂Et | O | H, H |
| 4-Cl | 5-Cl | CH₂ | CO₂Et | O | H, H |
| 4-Br | 5-Cl | CH₂ | CO₂Et | O | H, H |
| 4-CF₃ | H | CH₂ | CO₂-i-Pr | O | H, H |
| 4-Cl | H | CH₂ | CO₂i-Pr | O | H, H |
| 4-Br | H | CH₂ | CO₂i-Pr | O | H, H |
| 4-CF₃ | H | CH₂ | CO₂CH₂CF₃ | O | H, H |
| 4-Cl | H | CH₂ | CO₂CH₂CF₃ | O | H, H |
| 4-Br | H | CH₂ | CO₂CH₂CF₃ | O | H, H |
| 4-CF₃ | H | CH₂ | CO₂allyl | O | H, H |
| 4-Cl | H | CH₂ | CO₂allyl | O | H, H |
| 4-Br | H | CH₂ | CO₂allyl | O | H, H |
| 4-CF₃ | H | CH₂ | CO₂CH₂CH₂Cl | O | H, H |
| 4-Cl | H | CH₂ | CO₂CH₂CH₂Cl | O | H, H |
| 4-Br | H | CH₂ | CO₂CH₂CH₂Cl | O | H, H |
| 4-CF₃ | H | CH₂ | Ph | O | H, H |
| 4-Cl | H | CH₂ | Ph | O | H, H |
| 4-Br | H | CH₂ | Ph | O | H, H |
| 4-CF₃ | 5-Cl | CH₂ | Ph | O | H, H |
| 4-Cl | 5-Cl | CH₂ | Ph | O | H, H |
| 4-Br | 5-Cl | CH₂ | Ph | O | H, H |
| 4-CF₃ | H | CH₂ | 4-Cl—Ph | O | H, H |
| 4-Cl | H | CH₂ | 4-Cl—Ph | O | H, H |
| 4-Br | H | CH₂ | 4-Cl—Ph | O | H, H |
| 4-CF₃ | 5-CF₃ | CH₂ | 4-Cl—Ph | O | H, H |
| 4-Cl | 5-CF₃ | CH₂ | 4-Cl—Ph | O | H, H |
| 4-Br | 5-CF₃ | CH₂ | 4-Cl—Ph | O | H, H |
| 4-CF₃ | H | CH₂ | 4-F—Ph | O | H, H |
| 4-Cl | H | CH₂ | 4-F—Ph | O | H, H |
| 4-Br | H | CH₂ | 4-F—Ph | O | H, H |
| 4-CF₃ | H | CH₂ | H | O | Me, H |
| 4-Cl | H | CH₂ | H | O | Me, H |
| 4-Br | H | CH₂ | H | O | Me, H |
| 4-CF₃ | 5-Cl | CH₂ | H | O | Me, Me |
| 4-Cl | 5-Cl | CH₂ | H | O | Me, Me |
| 4-Br | 5-Cl | CH₂ | H | O | Me, Me |
| 4-CF₃ | H | CH₂ | H | S | H, H |
| 4-Cl | H | CH₂ | H | S | H, H |

TABLE 1-continued

| R₁ | R₂ | A | B | X | Rₐ¹, Rₐ² |
|---|---|---|---|---|---|
| 4-Br | H | CH₂ | H | S | H, H |
| 4-CF₃ | H | CH₂ | Me | S | H, H |
| 4-Cl | H | CH₂ | Me | S | H, H |
| 4-Br | H | CH₂ | Me | S | H, H |
| 4-CF₃ | H | CH₂ | CO₂Me | S | H, H |
| 4-Cl | H | CH₂ | CO₂Me | S | H, H |
| 4-Br | H | CH₂ | CO₂Me | S | H, H |
| 4-CF₃ | 5-Cl | CH₂ | H | S | H, H |
| 4-Cl | 5-Cl | CH₂ | H | S | H, H |
| 4-Br | 5-Cl | CH₂ | H | S | H, H |
| 4-CF₃ | 5-Cl | CH₂ | Me | S | H, H |
| 4-Cl | 5-Cl | CH₂ | Me | S | H, H |
| 4-Br | 5—Cl | CH₂ | Me | S | H, H |
| 4-CF₃ | 5—Cl | CH₂ | CO₂Me | S | H, H |
| 4-Cl | 5-Cl | CH₂ | CO₂Me | S | H, H |
| Br | 5-Cl | CH₂ | CO₂Me | S | H, H |
| 4-CF₃ | 5-Me | CH₂ | H | S | H, H |
| 4-Cl | 5-Me | CH₂ | H | S | H, H |
| 4-Br | 5-Me | CH₂ | H | S | H, H |
| 4-CF₃ | H | O | H | O | H, H |
| 4-Cl | H | O | H | O | H, H |
| 4-Br | H | O | H | O | H, H |
| 4-CF₃ | 5-Cl | O | H | O | H, H |
| 4-Cl | 5-Cl | O | H | O | H, H |
| 4-Br | 5-Cl | O | H | O | H, H |
| 4-CF₃ | 5-Br | O | H | O | H, H |
| 4-Cl | 5-Br | O | H | O | H, H |
| 4-Br | 5-Br | O | H | O | H, H |
| 4-CF₃ | 5-CF₃ | O | H | O | H, H |
| 4-Cl | 5-CF₃ | O | H | O | H, H |
| 4-Br | 5-CF₃ | O | H | O | H, H |
| 4-CF₃ | H | O | Me | O | H, H |
| 4-Cl | H | O | Me | O | H, H |
| 4-Br | H | O | Me | O | H, H |
| 4-CF₃ | 5-Cl | O | Me | O | H, H |
| 4-Cl | 5-Cl | O | Me | O | H, H |
| 4-Br | 5-Cl | O | Me | O | H, H |
| 4-CF₃ | 5-Br | O | Me | O | H, H |
| 4-Cl | 5-Br | O | Me | O | H, H |
| 4-Br | 5-Br | O | Me | O | H, H |
| 4-CF₃ | 5-CF₃ | O | Me | O | H, H |
| 4-Cl | 5-CF₃ | O | Me | O | H, H |
| 4-Br | 5-CF₃ | O | Me | O | H, H |
| 4-CF₃ | 5-F | O | Me | O | H, H |
| 4-Cl | 5-F | O | Me | O | H, H |
| 4-Br | 5-F | O | Me | O | H, H |
| 4-CF₃ | H | O | CO₂Me | O | H, H |
| 4-Cl | H | O | CO₂Me | O | H, H |
| 4-Cl | H | O | CO₂Me | O | H, H |
| 4-Br | H | O | CO₂Me | O | H, H |
| 4-CF₃ | 5-Cl | O | CO₂Me | O | H, H |
| 4-Cl | 5-Cl | O | CO₂Me | O | H, H |
| 4-Br | 5-Cl | O | CO₂Me | O | H, H |
| 4-CF₃ | H | O | Ph | O | H, H |
| 4-Cl | H | O | Ph | O | H, H |
| 4-Br | H | O | Ph | O | H, H |
| 4-CF₃ | 5-Br | O | Ph | O | H, H |
| 4-Cl | 5-Br | O | Ph | O | H, H |
| 4-Br | 5-Br | O | Ph | O | H, H |
| 4-CF₃ | H | O | H | O | Me, Me |
| 4-Cl | H | O | H | O | Me, Me |
| 4-Br | H | O | H | O | Me, Me |
| 4-CF₃ | H | O | H | O | H, Me |
| 4-Cl | H | O | H | O | H, Me |
| 4-Br | H | O | H | O | H, Me |
| 4-CF₃ | H | O | H | O | H, Ph |
| 4-Cl | H | O | H | O | H, Ph |
| 4-Br | H | O | H | O | H, Ph |
| 4-CF₃ | H | O | H | O | H, CO₂Me |
| 4-Cl | H | O | H | O | H, CO₂Me |
| 4-Br | H | O | H | O | H, CO₂Me |
| 4-CF₃ | H | O | H | S | H, H |
| 4-Cl | H | O | H | S | H, H |
| 4-Br | H | O | H | S | H, H |
| 4-CF₃ | H | S | H | O | H, H |
| 4-Cl | H | S | H | O | H, H |
| 4-Br | H | S | H | O | H, H |
| 4-CF₃ | 5-Cl | S | H | O | H, H |
| 4-Cl | 5-Cl | S | H | O | H, H |
| 4-Br | 5-Cl | S | H | O | H, H |
| 4-CF₃ | 5-Br | S | H | O | H, H |
| 4-Cl | 5-Br | S | H | O | H, H |
| 4-Br | 5-Br | S | H | O | H, H |
| 4-CF₃ | 5-CF₃ | S | H | O | H, H |
| 4-Cl | 5-CF₃ | S | H | O | H, H |
| 4-Br | 5-CF₃ | S | H | O | H, H |
| 4-CF₃ | H | S | Me | O | H, H |
| 4-Cl | H | S | Me | O | H, H |
| 4-Br | H | S | Me | O | H, H |
| 4-CF₃ | 5-Cl | S | Me | O | H, H |
| 4-Cl | 5-Cl | S | Me | O | H, H |
| 4-Br | 5-Cl | S | Me | O | H, H |
| 4-CF₃ | 5-Br | S | Me | O | H, H |
| 4-Cl | 5-Br | S | Me | O | H, H |
| 4-Br | 5-Br | S | Me | O | H, H |
| 4-CF₃ | 5-CF₃ | S | Me | O | H, H |
| 4-Cl | 5-CF₃ | S | Me | O | H, H |
| 4-Br | 5-CF₃ | S | Me | O | H, H |
| 4-CF₃ | 5-F | S | Me | O | H, H |
| 4-Cl | 5-F | S | Me | O | H, H |
| 4-Br | 5-F | S | Me | O | H, H |
| 4-CF₃ | H | S | CO₂Me | O | H, H |
| 4-Cl | H | S | CO₂Me | O | H, H |
| 4-Br | H | S | CO₂Me | O | H, H |
| 4-CF₃ | 5-Cl | S | CO₂Me | O | H, H |
| 4-Cl | 5-Cl | S | CO₂Me | O | H, H |
| 4-Br | 5-Cl | S | CO₂Me | O | H, H |
| 4-CF₃ | H | S | Ph | O | H, H |
| 4-Cl | H | S | Ph | O | H, H |
| 4-Br | H | S | Ph | O | H, H |
| 4-CF₃ | 5-Br | S | Ph | O | H, H |
| 4-Cl | 5-Br | S | Ph | O | H, H |
| 4-Br | 5-Br | S | Ph | O | H, H |
| 4-CF₃ | H | S | H | O | Me, Me |
| 4-Cl | H | S | H | O | Me, Me |
| 4-Br | H | S | H | O | Me, Me |
| 4-CF₃ | H | S | H | O | H, Me |
| 4-Cl | H | S | H | O | H, Me |
| 4-Br | H | S | H | O | H, Me |
| 4-CF₃ | H | S | H | O | H, Ph |
| 4-Cl | H | S | H | O | H, Ph |
| 4-Br | H | S | H | O | H, Ph |
| 4-CF₃ | H | S | H | O | H, CO₂Me |
| 4-Cl | H | S | H | O | H, CO₂Me |
| 4-Br | H | S | H | O | H, CO₂Me |
| 4-CF₃ | H | S | H | S | H, H |
| 4-Cl | H | S | H | S | H, H |
| 4-Br | H | S | H | S | H, H |
| 4-SMe | H | CH₂ | CO₂Me | O | H, H |
| 4-SO₂Me | H | CH₂ | CO₂Me | O | H, H |
| 4-OCF₂CF₂H | H | CH₂ | CO₂Me | O | H, H |
| 4-CF₂Cl | H | CH₂ | CO₂Me | O | H, H |
| 4-CO₂Me | H | CH₂ | CO₂Me | O | H, H |
| 4-CO₂CF₃ | H | CH₂ | CO₂Me | O | H, H |
| 4-F | H | CH₂ | CO₂Me | O | H, H |
| 4-CN | H | CH₂ | CO₂Me | O | H, H |
| 4-Me | H | CH₂ | CO₂Me | O | H, H |
| 3,4-CH₂C(Me)₂O¹ | H | CH₂ | CO₂Me | O | H, H |
| 3,4-CF₂CF₂O² | H | CH₂ | CO₂Me | O | H, H |
| 4-CF₃, 3-Cl | H | CH₂ | CO₂Me | O | H, H |
| 4-I | H | CH₂ | CO₂Me | O | H, H |
| 4-OMe | H | CH₂ | CO₂Me | O | H, H |
| 4-O-t-Bu | H | CH₂ | CO₂Me | O | H, H |
| 4-t-Bu | H | CH₂ | CO₂Me | O | H, H |
| 4-CF₃ | H | CH₂ | CO₂H | O | H, H |
| 4-CF₃ | H | CH₂ | CONH₂ | O | H, H |
| 4-CF₃ | H | CH₂ | CONHMe | O | H, H |

TABLE 1-continued

| $R_1$ | $R_2$ | A | B | X | $R_a^1, R_a^2$ |
|---|---|---|---|---|---|
| 4-CF$_3$ | H | CH$_2$ | CONMe | O | H, H |
| 4-CF$_3$ | H | CH$_2$ | CO$_2$CH$_2$Ph | O | H, H |
| 4-CF$_3$ | H | CH$_2$ | CH$_2$Ph | O | H, H |
| 4-CF$_3$ | H | CH$_2$ | OH | O | H, H |
| 4-CF$_3$ | H | CH$_2$ | OAc | O | H, H |
| 4-CF$_3$ | H | CH$_3$ | CH$_2$CF$_3$ | O | H, H |
| 4-CF$_3$ | H | CH$_2$ | CH$_2$OCH$_3$ | O | H, H |
| 4-CF$_3$ | H | CH$_2$ | CH$_2$CO$_2$Me | O | H, H |
| 4-CF$_3$ | H | CH$_2$ | CH$_2$CH$_2$CN | O | H, H |

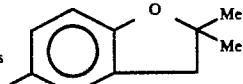

[1] designates Ph(R$_1$) as

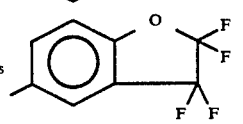

[2] designates Ph(R$_1$) as

TABLE 2

| $R_1$ | $R_2$ | A | B | X | $R_a^1, R_a^2$ |
|---|---|---|---|---|---|
| 4-CF$_3$ | H | CH$_2$ | H | O | H,H |
| 4-Cl | H | CH$_2$ | H | O | H,H |
| 4-Br | H | CH$_2$ | H | O | H,H |
| 4-CF$_3$ | 4-F | CH$_2$ | H | O | H,H |
| 4-Cl | 4-F | CH$_2$ | H | O | H,H |
| 4-Br | 4-F | CH$_2$ | H | O | H,H |
| 4-CF$_3$ | 4-Cl | CH$_2$ | H | O | H,H |
| 4-Cl | 4-Cl | CH$_2$ | H | O | H,H |
| 4-Br | 4-Cl | CH$_2$ | H | O | H,H |
| 4-CF$_3$ | 4-Me | CH$_2$ | H | O | H,H |
| 4-Cl | 4-Me | CH$_2$ | H | O | H,H |
| 4-Br | 4-Me | CH$_2$ | H | O | H,H |
| 4-CF$_3$ | 4-OMe | CH$_2$ | H | O | H,H |
| 4-Cl | 4-OMe | CH$_2$ | H | O | H,H |
| 4-Br | 4-OMe | CH$_2$ | H | O | H,H |
| 4-CF$_3$ | 4-Br | CH$_2$ | H | O | H,H |
| 4-Cl | 4-Br | CH$_2$ | H | O | H,H |
| 4-Br | 4-Br | CH$_2$ | H | O | H,H |
| 4-CF$_3$ | 6-F | CH$_2$ | H | O | H,H |
| 4-Cl | 6-F | CH$_2$ | H | O | H,H |
| 4-Br | 6-F | CH$_2$ | H | O | H,H |
| 4-CF$_3$ | 6-Cl | CH$_2$ | H | O | H,H |
| 4-Cl | 6-Cl | CH$_2$ | H | O | H,H |
| 4-Br | 6-Cl | CH$_2$ | H | O | H,H |
| 4-CF$_3$ | 7-F | CH$_2$ | H | O | H,H |
| 4-Cl | 7-F | CH$_2$ | H | O | H,H |
| 4-Br | 7-F | CH$_2$ | H | O | H,H |
| 4-CF$_3$ | H | CH$_2$ | Me | O | H,H |
| 4-Cl | H | CH$_2$ | Me | O | H,H |
| 4-Br | H | CH$_2$ | Me | O | H,H |
| 4-CF$_3$ | 4-F | CH$_2$ | CH$_3$ | O | H,H |
| 4-Cl | 4-F | CH$_2$ | CH$_3$ | O | H,H |
| 4-Br | 4-F | CH$_2$ | CH$_3$ | O | H,H |
| 4-CF$_3$ | 4-Cl | CH$_2$ | CH$_3$ | O | H,H |
| 4-Cl | 4-Cl | CH$_2$ | CH$_3$ | O | H,H |
| 4-Br | 4-Cl | CH$_2$ | CH$_3$ | O | H,H |
| 4-CF$_3$ | H | CH$_2$ | Et | O | H,H |
| 4-Cl | H | CH$_2$ | Et | O | H,H |
| 4-Br | H | CH$_2$ | Et | O | H,H |
| 4-CF$_3$ | 4-F | CH$_2$ | Et | O | H,H |
| 4-Cl | 4-F | CH$_2$ | Et | O | H,H |
| 4-Br | 4-F | CH$_2$ | Et | O | H,H |
| 4-CF$_3$ | 4-Cl | CH$_2$ | Et | O | H,H |
| 4-Cl | 4-Cl | CH$_2$ | Et | O | H,H |
| 4-Br | 4-Cl | CH$_2$ | CH$_2$ | O | H,H |
| 4-CF$_3$ | H | CH$_2$ | allyl | O | H,H |
| 4-Cl | H | CH$_2$ | allyl | O | H,H |
| 4-Br | H | CH$_2$ | allyl | O | H,H |
| 4-CF$_3$ | 4-F | CH$_2$ | allyl | O | H,H |
| 4-Cl | 4-F | CH$_2$ | allyl | O | H,H |
| 4-Br | 4-F | CH$_2$ | allyl | O | H,H |
| 4-CF$_3$ | 4-Cl | CH$_2$ | allyl | O | H,H |
| 4-Cl | 4-Cl | CH$_2$ | allyl | O | H,H |
| 4-Br | 4-Cl | CH$_2$ | allyl | O | H,H |
| 4-CF$_3$ | H | CH$_2$ | CO$_2$Me | O | H,H |
| 4-Cl | H | CH$_2$ | CO$_2$Me | O | H,H |
| 4-Br | H | CH$_2$ | CO$_2$Me | O | H,H |
| 4-CF$_3$ | 4-F | CH$_2$ | CO$_2$Me | O | H,H |
| 4-Cl | 4-F | CH$_2$ | CO$_2$Me | O | H,H |

TABLE 2-continued

| $R_1$ | $R_2$ | A | B | X | $R_a^1, R_a^2$ |
|---|---|---|---|---|---|
| 4-Br | 4-F | CH$_2$ | CO$_2$Me | O | H,H |
| 4-CF$_3$ | 4-Cl | CH$_2$ | CO$_2$Me | O | H,H |
| 4-Cl | 4-Cl | CH$_2$ | CO$_2$Me | O | H,H |
| 4-Br | 4-Cl | CH$_2$ | CO$_2$Me | O | H,H |
| 4-CF$_3$ | 4-CN | CH$_2$ | CO$_2$Me | O | H,H |
| 4-Cl | 4-CN | CH$_2$ | CO$_2$Me | O | H,H |
| 4-Br | 4-CN | CH$_2$ | CO$_2$Me | O | H,H |
| 4-CF$_3$ | 4-Br | CH$_2$ | CO$_2$Me | O | H,H |
| 4-Cl | 4-Br | CH$_2$ | CO$_2$Me | O | H,H |
| 4-Br | 4-Br | CH$_2$ | CO$_2$Me | O | H,H |
| 4-CF$_3$ | 4-CF$_3$ | CH$_2$ | CO$_2$Me | O | H,H |
| 4-Cl | 4-CF$_3$ | CH$_2$ | CO$_2$Me | O | H,H |
| 4-Br | 4-CF$_3$ | CH$_2$ | CO$_2$Me | O | H,H |
| 4-CF$_3$ | 4-Me | CH$_2$ | CO$_2$Me | O | H,H |
| 4-Cl | 4-Me | CH$_2$ | CO$_2$Me | O | H,H |
| 4-Br | 4-Me | CH$_2$ | CO$_2$Me | O | H,H |
| 4-CF$_3$ | H | CH$_2$ | CO$_2$Et | O | H,H |
| 4-Cl | H | CH$_2$ | CO$_2$Et | O | H,H |
| 4-Br | H | CH$_2$ | CO$_2$Et | O | H,H |
| 4-CF$_3$ | 4-F | CH$_2$ | CO$_2$Et | O | H,H |
| 4-Cl | 4-F | CH$_2$ | CO$_2$Et | O | H,H |
| 4-Br | 4-F | CH$_2$ | CO$_2$Et | O | H,H |
| 4-CF$_3$ | H | CH$_2$ | CO$_2$-i-Pr | O | H,H |
| 4-Cl | H | CH$_2$ | CO$_2$-i-Pr | O | H,H |
| 4-Br | H | CH$_2$ | CO$_2$-i-Pr | O | H,H |
| 4-CF$_3$ | H | CH$_2$ | CO$_2$CH$_2$CF$_3$ | O | H,H |
| 4-Cl | H | CH$_2$ | CO$_2$CH$_2$CF$_3$ | O | H,H |
| 4-Br | H | CH$_2$ | CO$_2$CH$_2$CF$_3$ | O | H,H |
| 4-CF$_3$ | H | CH$_2$ | CO$_2$allyl | O | H,H |
| 4-Cl | H | CH$_2$ | CO$_2$allyl | O | H,H |
| 4-Br | H | CH$_2$ | CO$_2$allyl | O | H,H |
| 4-CF$_3$ | H | CH$_2$ | CO$_2$CH$_2$CH$_2$Cl | O | H,H |
| 4-Cl | H | CH$_2$ | CO$_2$CH$_2$CH$_2$Cl | O | H,H |
| 4-Br | H | CH$_2$ | CO$_2$CH$_2$CH$_2$Cl | O | H,H |
| 4-CF$_3$ | H | CH$_2$ | Ph | O | H,H |
| 4-Cl | H | CH$_2$ | Ph | O | H,H |
| 4-Br | H | CH$_2$ | Ph | O | H,H |
| 4-CF$_3$ | 4-F | CH$_2$ | Ph | O | H,H |
| 4-Cl | 4-F | CH$_2$ | Ph | O | H,H |
| 4-Br | 4-F | CH$_2$ | Ph | O | H,H |
| 4-CF$_3$ | H | CH$_2$ | 4-Cl-Ph | O | H,H |
| 4-Cl | H | CH$_2$ | 4-Cl-Ph | O | H,H |
| 4-Br | H | CH$_2$ | 4-Cl-Ph | O | H,H |
| 4-CF$_3$ | 4-F | CH$_2$ | 4-Cl-Ph | O | H,H |
| 4-Cl | 4-F | CH$_2$ | 4-Cl-Ph | O | H,H |
| 4-Br | 4-F | CH$_2$ | 4-Cl-Ph | O | H,H |
| 4-CF$_3$ | H | CH$_2$ | 4-F-Ph | O | H,H |
| 4-Cl | H | CH$_2$ | 4-F-Ph | O | H,H |
| 4-Br | H | CH$_2$ | 4-F-Ph | O | H,H |
| 4-CF$_3$ | H | CH$_2$ | H | O | H,Me |
| 4-Cl | H | CH$_2$ | H | O | H,Me |
| 4-Br | H | CH$_2$ | H | O | H,Me |
| 4-CF$_3$ | H | CH$_2$ | H | O | Me,Me |
| 4-Cl | H | CH$_2$ | H | O | Me,Me |
| 4-Br | H | CH$_2$ | H | O | Me,Me |
| 4-CF$_3$ | H | CH$_2$ | H | S | H,H |
| 4-Cl | H | CH$_2$ | H | S | H,H |
| 4-Br | H | CH$_2$ | H | S | H,H |
| 4-CF$_3$ | H | CH$_2$ | Me | S | H,H |
| 4-Cl | H | CH$_2$ | Me | S | H,H |
| 4-Br | H | CH$_2$ | Me | S | H,H |
| 4-CF$_3$ | H | CH$_2$ | CO$_2$Me | S | H,H |
| 4-Cl | H | CH$_2$ | CO$_2$Me | S | H,H |
| 4-Br | H | CH$_2$ | CO$_2$Me | S | H,H |
| 4-CF$_3$ | H | CH$_2$ | H | S | H,H |
| 4-Cl | H | CH$_2$ | H | S | H,H |
| 4-Br | H | CH$_2$ | H | S | H,H |
| 4-CF$_3$ | 4-F | CH$_2$ | Me | S | H,H |
| 4-Cl | 4-F | CH$_2$ | Me | S | H,H |
| 4-Br | 4-F | CH$_2$ | Me | S | H,H |
| 4-CF$_3$ | 4-F | CH$_2$ | CO$_2$Me | S | H,H |
| 4-Cl | 4-F | CH$_2$ | CO$_2$Me | S | H,H |
| 4-Br | 4-F | CH$_2$ | CO$_2$Me | S | H,H |
| 4-CF$_3$ | 4-F | CH$_2$ | H | S | H,H |
| 4-Cl | 4-F | CH$_2$ | H | S | H,H |
| 4-Br | 4-F | CH$_2$ | H | S | H,H |
| 4-CF$_3$ | H | O | H | O | H,H |
| 4-Cl | H | O | H | O | H,H |
| 4-Br | H | O | H | O | H,H |
| 4-CF$_3$ | 4-F | O | H | O | H,H |
| 4-Cl | 4-F | O | H | O | H,H |

TABLE 2-continued

| R₁ | R₂ | A | B | X | $R_a^1, R_a^2$ |
|---|---|---|---|---|---|
| 4-Br | 4-F | O | H | O | H,H |
| 4-CF₃ | 4-Cl | O | H | O | H,H |
| 4-Cl | 4-Cl | O | H | O | H,H |
| 4-Br | 4-Cl | O | H | O | H,H |
| 4-CF₃ | 4-Me | O | H | O | H,H |
| 4-Cl | 4-Me | O | H | O | H,H |
| 4-Br | 4-Me | O | H | O | H,H |
| 4-CF₃ | H | O | Me | O | H,H |
| 4-Cl | H | O | Me | O | H,H |
| 4-Br | H | O | Me | O | H,H |
| 4-CF₃ | 4-F | O | Me | O | H,H |
| 4-Cl | 4-F | O | Me | O | H,H |
| 4-Br | 4-F | O | Me | O | H,H |
| 4-CF₃ | 4-Cl | O | Me | O | H,H |
| 4-Cl | 4-Cl | O | Me | O | H,H |
| 4-Br | 4-Cl | O | Me | O | H,H |
| 4-CF₃ | 4-Me | O | Me | O | H,H |
| 4-Cl | 4-Me | O | Me | O | H,H |
| 4-Br | 4-Me | O | Me | O | H,H |
| 4-CF₃ | 4-CF₃ | O | Me | O | H,H |
| 4-Cl | 4-CF₃ | O | Me | O | H,H |
| 4-Br | 4-CF₃ | O | Me | O | H,H |
| 4-CF₃ | H | O | CO₂Me | O | H,H |
| 4-Cl | H | O | CO₂Me | O | H,H |
| 4-Br | H | O | CO₂Me | O | H,H |
| 4-CF₃ | 4-F | O | CO₂Me | O | H,H |
| 4-Cl | 4-F | O | CO₂Me | O | H,H |
| 4-Br | 4-F | O | CO₂Me | O | H,H |
| 4-CF₃ | H | O | Ph | O | H,H |
| 4-Cl | H | O | Ph | O | H,H |
| 4-Br | H | O | Ph | O | H,H |
| 4-CF₃ | 4-F | O | Ph | O | H,H |
| 4-Cl | 4-F | O | Ph | O | H,H |
| 4-Br | 4-F | O | Ph | O | H,H |
| 4-CF₃ | H | O | H | O | Me,Me |
| 4-Cl | H | O | H | O | Me,Me |
| 4-Br | H | O | H | O | Me,Me |
| 4-CF₃ | H | O | H | O | H,Me |
| 4-Cl | H | O | H | O | H,Me |
| 4-Br | H | O | H | O | H,Me |
| 4-CF₃ | H | O | H | O | H,Ph |
| 4-Cl | H | O | H | O | H,Ph |
| 4-Br | H | O | H | O | H,Ph |
| 4-CF₃ | H | O | H | O | H,CO₂Me |
| 4-Cl | H | O | H | O | H,CO₂Me |
| 4-Br | H | O | H | O | H,CO₂Me |
| 4-CF₃ | H | O | H | S | H,H |
| 4-Cl | H | O | H | S | H,H |
| 4-Br | H | O | H | S | H,H |
| 4-CF₃ | H | S | H | O | H,H |
| 4-Cl | H | S | H | O | H,H |
| 4-Br | H | S | H | O | H,H |
| 4-CF₃ | 4-F | S | H | O | H,H |
| 4-Cl | 4-F | S | H | O | H,H |
| 4-Br | 4-F | S | H | O | H,H |
| 4-CF₃ | 4-Cl | S | H | O | H,H |
| 4-Cl | 4-Cl | S | H | O | H,H |
| 4-Br | 4-Cl | S | H | O | H,H |
| 4-CF₃ | 4-Me | S | H | O | H,H |
| 4-Cl | 4-Me | S | H | O | H,H |
| 4-Br | 4-Me | S | H | O | H,H |
| 4-CF₃ | H | S | Me | O | H,H |
| 4-Cl | H | S | Me | O | H,H |
| 4-Br | H | S | Me | O | H,H |
| 4-CF₃ | 4-F | S | Me | O | H,H |
| 4-Cl | 4-F | S | Me | O | H,H |
| 4-Br | 4-F | S | Me | O | H,H |
| 4-CF₃ | 4-Cl | S | Me | O | H,H |
| 4-Cl | 4-Cl | S | Me | O | H,H |
| 4-Br | 4-Cl | S | Me | O | H,H |
| 4-CF₃ | 4-Me | S | Me | O | H,H |
| 4-Cl | 4-Me | S | Me | O | H,H |
| 4-Br | 4-Me | S | Me | O | H,H |
| 4-CF₃ | 6-F | S | Me | O | H,H |
| 4-Cl | 6-F | S | Me | O | H,H |
| 4-Br | 6-F | S | Me | O | H,H |
| 4-CF₃ | H | S | CO₂Me | O | H,H |
| 4-Cl | H | S | CO₂Me | O | H,H |
| 4-Br | H | S | CO₂Me | O | H,H |
| 4-CF₃ | 4-F | S | CO₂Me | O | H,H |
| 4-Cl | 4-F | S | CO₂Me | O | H,H |
| 4-Br | 4-F | S | CO₂Me | O | H,H |
| 4-CF₃ | 4-Cl | S | Ph | O | H,H |
| 4-Cl | 4-Cl | S | Ph | O | H,H |
| 4-Br | 4-Cl | S | Ph | O | H,H |
| 4-CF₃ | H | S | Ph | O | H,H |
| 4-Cl | H | S | Ph | O | H,H |
| 4-Br | H | S | Ph | O | H,H |
| 4-CF₃ | H | S | H | O | Me,Me |
| 4-Cl | H | S | H | O | Me,Me |
| 4-Br | H | S | H | O | Me,Me |
| 4-CF₃ | H | S | H | O | H,Me |
| 4-Cl | H | S | H | O | H,Me |
| 4-Br | H | S | H | O | H,Me |
| 4-CF₃ | H | S | H | O | H,Ph |
| 4-Cl | H | S | H | O | H,Ph |
| 4-Br | H | S | H | O | H,Ph |
| 4-CF₃ | H | S | H | O | H,CO₂Me |
| 4-Cl | H | S | H | O | H,CO₂Me |
| 4-Br | H | S | H | O | H,CO₂Me |
| 4-CF₃ | H | S | H | S | H,H |
| 4-Cl | H | S | H | S | H,H |
| 4-Br | H | S | H | S | H,H |

TABLE 3

| R₁ | R₂ | A | B | X | $R_a^1, R_a^2$ |
|---|---|---|---|---|---|
| 4-CF₃ | H | CH₂ | H | O | H,H |
| 4-Cl | H | CH₂ | H | O | H,H |
| 4-Br | H | CH₂ | H | O | H,H |
| 4-CF₃ | 5-Cl | CH₂ | H | O | H,H |
| 4-Cl | 5-Cl | CH₂ | H | O | H,H |
| 4-Br | 5-Cl | CH₂ | H | O | H,H |
| 4-CF₃ | 5-F | CH₂ | H | O | H,H |
| 4-Cl | 5-F | CH₂ | H | O | H,H |
| 4-Br | 5-F | CH₂ | H | O | H,H |
| 4-CF₃ | 5-CN | CH₂ | H | O | H,H |
| 4-Cl | 5-CN | CH₂ | H | O | H,H |
| 4-Br | 5-CN | CH₂ | H | O | H,H |
| 4-CF₃ | 5-Br | CH₂ | H | O | H,H |
| 4-Cl | 5-Br | CH₂ | H | O | H,H |
| 4-Br | 5-Br | CH₂ | H | O | H,H |
| 4-CF₃ | 5-Me | CH₂ | H | O | H,H |
| 4-Cl | 5-Me | CH₂ | H | O | H,H |
| 4-Br | 5-Me | CH₂ | H | O | H,H |
| 4-CF₃ | 7-F | CH₂ | H | O | H,H |
| 4-Cl | 7-F | CH₂ | H | O | H,H |
| 4-Br | 7-F | CH₂ | H | O | H,H |
| 4-CF₃ | 5-NMe₂ | CH₂ | H | O | H,H |
| 4-Cl | 5-NMe₂ | CH₂ | H | O | H,H |
| 4-Br | 5-NMe₂ | CH₂ | H | O | H,H |
| 4-CF₃ | 5-CF₃ | CH₂ | H | O | H,H |
| 4-Cl | 5-CF₃ | CH₂ | H | O | H,H |
| 4-Br | 5-CF₃ | CH₂ | H | O | H,H |
| 4-CF₃ | H | CH₂ | Me | O | H,H |
| 4-Cl | H | CH₂ | Me | O | H,H |
| 4-Br | H | CH₂ | Me | O | H,H |
| 4-CF₃ | 5-Cl | CH₂ | Me | O | H,H |
| 4-Cl | 5-Cl | CH₂ | Me | O | H,H |
| 4-Br | 5-Cl | CH₂ | Me | O | H,H |
| 4-CF₃ | 5-CF₃ | CH₂ | Me | O | H,H |
| 4-Cl | 5-CF₃ | CH₂ | Me | O | H,H |
| 4-Br | 5-CF₃ | CH₂ | Me | O | H,H |
| 4-CF₃ | H | CH₂ | Et | O | H,H |
| 4-Cl | H | CH₂ | Et | O | H,H |
| 4-Br | H | CH₂ | Et | O | H,H |
| 4-CF₃ | 5-F | CH₂ | Et | O | H,H |
| 4-Cl | 5-F | CH₂ | Et | O | H,H |
| 4-Br | 5-F | CH₂ | Et | O | H,H |
| 4-CF₃ | 5-CN | CH₂ | Et | O | H,H |
| 4-Cl | 5-CN | CH₂ | Et | O | H,H |
| 4-Br | 5-CN | CH₂ | Et | O | H,H |
| 4-CF₃ | H | CH₂ | allyl | O | H,H |
| 4-Cl | H | CH₂ | allyl | O | H,H |
| 4-Br | H | CH₂ | allyl | O | H,H |
| 4-CF₃ | 5-Br | CH₂ | allyl | O | H,H |
| 4-Cl | 5-Br | CH₂ | allyl | O | H,H |
| 4-Br | 5-Br | CH₂ | allyl | O | H,H |
| 4-CF₃ | 5-Cl | CH₂ | allyl | O | H,H |
| 4-Cl | 5-Cl | CH₂ | allyl | O | H,H |

TABLE 3-continued

| R₁ | R₂ | A | B | X | Rₐ¹, Rₐ² |
|---|---|---|---|---|---|
| 4-Br | 5-Cl | CH₂ | allyl | O | H,H |
| 4-CF₃ | H | CH₂ | CO₂Me | O | H,H |
| 4-Cl | H | CH₂ | CO₂Me | O | H,H |
| 4-Br | H | CH₂ | CO₂Me | O | H,H |
| 4-CF₃ | 5-F | CH₂ | CO₂Me | O | H,H |
| 4-Cl | 5-F | CH₂ | CO₂Me | O | H,H |
| 4-Br | 5-F | CH₂ | CO₂Me | O | H,H |
| 4-CF₃ | 5-Cl | CH₂ | CO₂Me | O | H,H |
| 4-Cl | 5-Cl | CH₂ | CO₂Me | O | H,H |
| 4-Br | 5-Cl | CH₂ | CO₂Me | O | H,H |
| 4-CF₃ | 5-Br | CH₂ | CO₂Me | O | H,H |
| 4-Cl | 5-Br | CH₂ | CO₂Me | O | H,H |
| 4-Br | 5-Br | CH₂ | CO₂Me | O | H,H |
| 4-CF₃ | 5-CN | CH₂ | CO₂Me | O | H,H |
| 4-Cl | 5-CN | CH₂ | CO₂Me | O | H,H |
| 4-Br | 5-CN | CH₂ | CO₂Me | O | H,H |
| 4-CF₃ | 5-CF₃ | CH₂ | CO₂Me | O | H,H |
| 4-Cl | 5-CF₃ | CH₂ | CO₂Me | O | H,H |
| 4-Br | 5-CF₃ | CH₂ | CO₂Me | O | H,H |
| 4-CF₃ | 5-Me | CH₂ | CO₂Me | O | H,H |
| 4-Cl | 5-Me | CH₂ | CO₂Me | O | H,H |
| 4-Br | 5-Me | CH₂ | CO₂Me | O | H,H |
| 4-CF₃ | H | CH₂ | CO₂Et | O | H,H |
| 4-Cl | H | CH₂ | CO₂Et | O | H,H |
| 4-Br | H | CH₂ | CO₂Et | O | H,H |
| 4-CF₃ | 5-Cl | CH₂ | CO₂Et | O | H,H |
| 4-Cl | 5-Cl | CH₂ | CO₂Et | O | H,H |
| 4-Br | 5-Cl | CH₂ | CO₂Et | O | H,H |
| 4-CF₃ | H | CH₂ | CO₂-i-Pr | O | H,H |
| 4-Cl | H | CH₂ | CO₂-i-Pr | O | H,H |
| 4-Br | H | CH₂ | CO₂-i-Pr | O | H,H |
| 4-CF₃ | H | CH₂ | CO₂CH₂CF₃ | O | H,H |
| 4-Cl | H | CH₂ | CO₂CH₂CF₃ | O | H,H |
| 4-Br | H | CH₂ | CO₂CH₂CF₃ | O | H,H |
| 4-CF₃ | H | CH₂ | CO₂allyl | O | H,H |
| 4-Cl | H | CH₂ | CO₂allyl | O | H,H |
| 4-Br | H | CH₂ | CO₂allyl | O | H,H |
| 4-CF₃ | H | CH₂ | CO₂CH₂CH₂Cl | O | H,H |
| 4-Cl | H | CH₂ | CO₂CH₂CH₂Cl | O | H,H |
| 4-Br | H | CH₂ | CO₂CH₂CH₂Cl | O | H,H |
| 4-CF₃ | H | CH₂ | Ph | O | H,H |
| 4-Cl | H | CH₂ | Ph | O | H,H |
| 4-Br | H | CH₂ | Ph | O | H,H |
| 4-CF₃ | 5-Cl | CH₂ | Ph | O | H,H |
| 4-Cl | 5-Cl | CH₂ | Ph | O | H,H |
| 4-Br | 5-Cl | CH₂ | Ph | O | H,H |
| 4-CF₃ | H | CH₂ | 4-Cl—Ph | O | H,H |
| 4-Cl | H | CH₂ | 4-Cl—Ph | O | H,H |
| 4-Br | H | CH₂ | 4-Cl—Ph | O | H,H |
| 4-CF₃ | 5-CF₃ | CH₂ | 4-Cl—Ph | O | H,H |
| 4-Cl | 5-CF₃ | CH₂ | 4-Cl—Ph | O | H,H |
| 4-Br | 5-CF₃ | CH₂ | 4-Cl—Ph | O | H,H |
| 4-CF₃ | H | CH₂ | 4-F—Ph | O | H,H |
| 4-Cl | H | CH₂ | 4-F—Ph | O | H,H |
| 4-Br | H | CH₂ | 4-F—Ph | O | H,H |
| 4-CF₃ | H | CH₂ | H | O | H,Me |
| 4-Cl | H | CH₂ | H | O | H,Me |
| 4-Br | H | CH₂ | H | O | H,Me |
| 4-CF₃ | 5-Cl | CH₂ | H | O | Me,Me |
| 4-Cl | 5-Cl | CH₂ | H | O | Me,Me |
| 4-Br | 5-Cl | CH₂ | H | O | Me,Me |
| 4-CF₃ | H | CH₂ | H | S | H,H |
| 4-Cl | H | CH₂ | H | S | H,H |
| 4-Br | H | CH₂ | H | S | H,H |
| 4-CF₃ | H | CH₂ | Me | S | H,H |
| 4-Cl | H | CH₂ | Me | S | H,H |
| 4-Br | H | CH₂ | Me | S | H,H |
| 4-CF₃ | H | CH₂ | CO₂Me | S | H,H |
| 4-Cl | H | CH₂ | CO₂Me | S | H,H |
| 4-Br | H | CH₂ | CO₂Me | S | H,H |
| 4-CF₃ | 5-Cl | CH₂ | H | S | H,H |
| 4-Cl | 5-Cl | CH₂ | H | S | H,H |
| 4-Br | 5-Cl | CH₂ | H | S | H,H |
| 4-CF₃ | 5-Cl | CH₂ | Me | S | H,H |
| 4-Cl | 5-Cl | CH₂ | Me | S | H,H |
| 4-Br | 5-Cl | CH₂ | Me | S | H,H |
| 4-CF₃ | 5-Cl | CH₂ | CO₂Me | S | H,H |
| 4-Cl | 5-Cl | CH₂ | CO₂Me | S | H,H |
| 4-Br | 5-Cl | CH₂ | CO₂Me | S | H,H |
| 4-CF₃ | 5-Me | CH₂ | H | S | H,H |
| 4-Cl | 5-Me | CH₂ | H | S | H,H |
| 4-Br | 5-Me | CH₂ | H | S | H,H |
| 4-CF₃ | H | O | H | O | H,H |
| 4-Cl | H | O | H | O | H,H |
| 4-Br | H | O | H | O | H,H |
| 4-CF₃ | 5-Cl | O | H | O | H,H |
| 4-Cl | 5-Cl | O | H | O | H,H |
| 4-Br | 5-Cl | O | H | O | H,H |
| 4-CF₃ | 5-Br | O | H | O | H,H |
| 4-Cl | 5-Br | O | H | O | H,H |
| 4-Br | 5-Br | O | H | O | H,H |
| 4-CF₃ | 5-CF₃ | O | H | O | H,H |
| 4-Cl | 5-CF₃ | O | H | O | H,H |
| 4-Br | 5-CF₃ | O | H | O | H,H |
| 4-CF₃ | H | O | Me | O | H,H |
| 4-Cl | H | O | Me | O | H,H |
| 4-Br | H | O | Me | O | H,H |
| 4-CF₃ | 5-Cl | O | Me | O | H,H |
| 4-Cl | 5-Cl | O | Me | O | H,H |
| 4-Br | 5-Cl | O | Me | O | H,H |
| 4-CF₃ | 5-Br | O | Me | O | H,H |
| 4-Cl | 5-Br | O | Me | O | H,H |
| 4-Br | 5-Br | O | Me | O | H,H |
| 4-CF₃ | 5-CF₃ | O | Me | O | H,H |
| 4-Cl | 5-CF₃ | O | Me | O | H,H |
| 4-Br | 5-CF₃ | O | Me | O | H,H |
| 4-CF₃ | 5-F | O | Me | O | H,H |
| 4-Cl | 5-F | O | Me | O | H,H |
| 4-Br | 5-F | O | Me | O | H,H |
| 4-CF₃ | H | O | CO₂Me | O | H,H |
| 4-Cl | H | O | CO₂Me | O | H,H |
| 4-Br | H | O | CO₂Me | O | H,H |
| 4-CF₃ | 5-Cl | O | CO₂Me | O | H,H |
| 4-Cl | 5-Cl | O | CO₂Me | O | H,H |
| 4-Br | 5-Cl | O | CO₂Me | O | H,H |
| 4-CF₃ | H | O | Ph | O | H,H |
| 4-Cl | H | O | Ph | O | H,H |
| 4-Br | H | O | Ph | O | H,H |
| 4-CF₃ | 5-Br | O | Ph | O | H,H |
| 4-Cl | 5-Br | O | Ph | O | H,H |
| 4-Br | 5-Br | O | Ph | O | H,H |
| 4-CF₃ | H | O | H | O | Me,Me |
| 4-Cl | H | O | H | O | Me,Me |
| 4-Br | H | O | H | O | Me,Me |
| 4-CF₃ | H | O | H | O | H,Me |
| 4-Cl | H | O | H | O | H,Me |
| 4-Br | H | O | H | O | H,Me |
| 4-CF₃ | H | O | H | O | H,Ph |
| 4-Cl | H | O | H | O | H,Ph |
| 4-Br | H | O | H | O | H,Ph |
| 4-CF₃ | H | O | H | O | H,CO₂Me |
| 4-Cl | H | O | H | O | H,CO₂Me |
| 4-Br | H | O | H | O | H,CO₂Me |
| 4-CF₃ | H | O | H | S | H,H |
| 4-Cl | H | O | H | S | H,H |
| 4-Br | H | O | H | S | H,H |
| 4-CF₃ | H | S | H | O | H,H |
| 4-Cl | H | S | H | O | H,H |
| 4-Br | H | S | H | O | H,H |
| 4-CF₃ | 5-Cl | S | H | O | H,H |
| 4-Cl | 5-Cl | S | H | O | H,H |
| 4-Br | 5-Cl | S | H | O | H,H |
| 4-CF₃ | 5-Br | S | H | O | H,H |
| 4-Cl | 5-Br | S | H | O | H,H |
| 4-Br | 5-Br | S | H | O | H,H |
| 4-CF₃ | 5-CF₃ | S | H | O | H,H |
| 4-Cl | 5-CF₃ | S | H | O | H,H |
| 4-Br | 5-CF₃ | S | H | O | H,H |
| 4-CF₃ | H | S | Me | O | H,H |
| 4-Cl | H | S | Me | O | H,H |
| 4-Br | H | S | Me | O | H,H |
| 4-CF₃ | 5-Cl | S | Me | O | H,H |
| 4-Cl | 5-Cl | S | Me | O | H,H |
| 4-Br | 5-Cl | S | Me | O | H,H |
| 4-CF₃ | 5-Br | S | Me | O | H,H |
| 4-Cl | 5-Br | S | Me | O | H,H |
| 4-Br | 5-Br | S | Me | O | H,H |
| 4-CF₃ | 5-CF₃ | S | Me | O | H,H |
| 4-Cl | 5-CF₃ | S | Me | O | H,H |
| 4-Br | 5-CF₃ | S | Me | O | H,H |
| 4-CF₃ | 5-F | S | Me | O | H,H |
| 4-Cl | 5-F | S | Me | O | H,H |

TABLE 3-continued

| R₁ | R₂ | A | B | X | $R_a^1, R_a^2$ |
|---|---|---|---|---|---|
| 4-Br | 5-F | S | Me | O | H,H |
| 4-CF₃ | H | S | CO₂Me | O | H,H |
| 4-Cl | H | S | CO₂Me | O | H,H |
| 4-Br | H | S | CO₂Me | O | H,H |
| 4-CF₃ | 5-Cl | S | CO₂Me | O | H,H |
| 4-Cl | 5-Cl | S | CO₂Me | O | H,H |
| 4-Br | 5-Cl | S | CO₂Me | O | H,H |
| 4-CF₃ | H | S | Ph | O | H,H |
| 4-Cl | H | S | Ph | O | H,H |
| 4-Br | H | S | Ph | O | H,H |
| 4-CF₃ | 5-Br | S | Ph | O | H,H |
| 4-Cl | 5-Br | S | Ph | O | H,H |
| 4-Br | 5-Br | S | Ph | O | H,H |
| 4-CF₃ | H | S | H | O | Me,Me |
| 4-Cl | H | S | H | O | Me,Me |
| 4-Br | H | S | H | O | Me,Me |
| 4-CF₃ | H | S | H | O | H,Me |
| 4-Cl | H | S | H | O | H,Me |
| 4-Br | H | S | H | O | H,Me |
| 4-CF₃ | H | S | H | O | H,Ph |
| 4-Cl | H | S | H | O | H,Ph |
| 4-Br | H | S | H | O | H,Ph |
| 4-CF₃ | H | S | H | O | H,CO₂Me |
| 4-Cl | H | S | H | O | H,CO₂Me |
| 4-Br | H | S | H | O | H,CO₂Me |
| 4-CF₃ | H | S | H | S | H,H |
| 4-Cl | H | S | H | S | H,H |
| 4-Br | H | S | H | S | H,H |

TABLE 4

| R₁ | R₂ | A | B | X | $R_a^1, R_a^2$ |
|---|---|---|---|---|---|
| 4-CF₃ | H | CH₂ | H | O | H, H |
| 4-Cl | H | CH₂ | H | O | H, H |
| 4-Br | H | CH₂ | H | O | H, H |
| 4-CF₃ | 4-Me | CH₂ | H | O | M, M |
| 4-Cl | 4-Me | CH₂ | H | O | H, H |
| 4-Br | 4-Me | CH₂ | H | O | H, H |
| 4-CF₃ | 4-F | CH₂ | H | O | H, H |
| 4-Cl | 4-F | CH₂ | H | O | H, H |
| 4-Br | 4-F | CH₂ | H | O | H, H |
| 4-CF₃ | 4-Cl | CH₂ | H | O | H, H |
| 4-Cl | 4-Cl | CH₂ | H | O | H, H |
| 4-Br | 4-Cl | CH₂ | H | O | H, H |
| 4-CF₃ | 5-F | CH₂ | H | O | H, H |
| 4-Cl | 5-F | CH₂ | H | O | H, H |
| 4-Br | 5-F | CH₂ | H | O | H, H |
| 4-CF₃ | 5-Cl | CH₂ | H | O | H, H |
| 4-Cl | 5-Cl | CH₂ | H | O | H, H |
| 4-Br | 5-Cl | CH₂ | H | O | H, H |
| 4-CF₃ | 5-Me | CH₂ | H | O | H, H |
| 4-Cl | 5-Me | CH₂ | H | O | H, H |
| 4-Br | 5-Me | CH₂ | H | O | H, H |
| 4-CF₃ | 5-Br | CH₂ | H | O | H, H |
| 4-Cl | 5-Br | CH₂ | H | O | H, H |
| 4-Br | 5-Br | CH₂ | H | O | H, H |
| 4-CF₃ | 5-OMe | CH₂ | H | O | H, H |
| 4-Cl | 5-OMe | CH₂ | H | O | H, H |
| 4-Br | 5-OMe | CH₂ | H | O | H, H |
| 4-CF₃ | H | CH₂ | Me | O | H, H |
| 4-Cl | H | CH₂ | Me | O | H, H |
| 4-Br | H | CH₂ | Me | O | H, H |
| 4-CF₃ | 4-F | CH₂ | Me | O | H, H |
| 4-Cl | 4-F | CH₂ | Me | O | H, H |
| 4-Br | 4-F | CH₂ | Me | O | H, H |
| 4-CF₃ | 5-F | CH₂ | Me | O | H, H |
| 4-Cl | 5-F | CH₂ | Me | O | H, H |
| 4-Br | 5-F | CH₂ | Me | O | H, H |
| 4-CF₃ | H | CH₂ | Me | O | H, H |
| 4-Cl | H | CH₂ | Et | O | H, H |
| 4-Br | H | CH₂ | Et | O | H, H |
| 4-CF₃ | 4-F | CH₂ | Et | O | H, H |
| 4-Cl | 4-F | CH₂ | Et | O | H, H |
| 4-Br | 4-F | CH₂ | Et | O | H, H |
| 4-CF₃ | 4-Cl | CH₂ | Et | O | H, H |
| 4-Cl | 4-Cl | CH₂ | Et | O | H, H |
| 4-Br | 4-Cl | CH₂ | et | O | H, H |
| 4-CF₃ | H | CH₂ | allyl | O | H, H |
| 4-Cl | H | CH₂ | allyl | O | H, H |

TABLE 4-continued

| R₁ | R₂ | A | B | X | $R_a^1, R_a^2$ |
|---|---|---|---|---|---|
| 4-Br | H | CH₂ | allyl | O | H, H |
| 4-CF₃ | 5-F | CH₂ | allyl | O | H, H |
| 4-Cl | 5-F | CH₂ | allyl | O | H, H |
| 4-Br | 5-F | CH₂ | allyl | O | H, H |
| 4-CF₃ | 5-Cl | CH₂ | allyl | O | H, H |
| 4-Cl | 5-Cl | CH₂ | allyl | O | H, H |
| 4-Br | 5-Cl | CH₂ | allyl | O | H, H |
| 4-CF₃ | H | CH₂ | CO₂Me | O | H, H |
| 4-Cl | H | CH₂ | CO₂Me | O | H, H |
| 4-Br | H | CH₂ | CO₂Me | O | H, H |
| 4-CF₃ | 4-F | CH₂ | CO₂Me | O | H, H |
| 4-Cl | 4-F | CH₂ | CO₂Me | O | H, H |
| 4-Br | 4-F | CH₂ | CO₂Me | O | H, H |
| 4-CF₃ | 4-F | CH₂ | CO₂Me | O | H, H |
| 4-Cl | 4-F | CH₂ | CO₂Me | O | H, H |
| 4-Br | 4-F | CH₂ | CO₂Me | O | H, H |
| 4-CF₃ | 5-F | CH₂ | CO₂Me | O | H, H |
| 4-Cl | 5-F | CH₂ | CO₂Me | O | H, H |
| 4-Br | 5-F | CH₂ | CO₂Me | O | H, H |
| 4-CF₃ | 4-Cl | CH₂ | CO₂Me | O | H, H |
| 4-Cl | 4-Cl | CH₂ | CO₂Me | O | H, H |
| 4-Br | 4-Cl | CH₂ | CO₂Me | O | H, H |
| 4-CF₃ | 5-Cl | CH₂ | CO₂Me | O | H, H |
| 4-Cl | 5-Cl | CH₂ | CO₂Me | O | H, H |
| 4-Br | 5-Cl | CH₂ | CO₂Me | O | H, H |
| 4-CF₃ | 5-CF₃ | CH₃ | CO₂Me | O | H, H |
| 4-Cl | 5-CF₃ | CH₂ | CO₂Me | O | H, H |
| 4-Br | 5-CF₃ | CH₂ | CO₂Me | O | H, H |
| 4-CF₃ | 5-Me | CH₂ | CO₂Me | O | H, H |
| 4-Cl | 5-Me | CH₂ | CO₂Me | O | H, H |
| 4-Br | 5-Me | CH₂ | CO₂Me | O | H, H |
| 4-CF₃ | H | CH₂ | CO₂Et | O | H, H |
| 4-Cl | H | CH₂ | CO₂Et | O | H, H |
| 4-Br | H | CH₂ | CO₂Et | O | H, H |
| 4-CF₃ | 5-Me | CH₂ | CO₂Et | O | H, H |
| 4-Cl | 5-Me | CH₂ | CO₂Et | O | H, H |
| 4-Br | 5-Me | CH₂ | CO₂Et | O | H, H |
| 4-CF₃ | H | CH₂ | CO₂i-Pr | O | H, H |
| 4-Cl | H | CH₂ | CO₂i-Pr | O | H, H |
| 4-Br | H | CH₂ | CO₂i-Pr | O | H, H |
| 4-CF₃ | H | CH₂ | CO₂CH₂CF₃ | O | H, H |
| 4-Cl | H | CH₂ | CO₂CH₂CF₃ | O | H, H |
| 4-Br | H | CH₂ | CO₂CH₂CF₃ | O | H, H |
| 4-CF₃ | H | CH₂ | CO₂allyl | O | H, H |
| 4-Cl | H | CH₂ | CO₂allyl | O | H, H |
| 4-Br | H | CH₂ | CO₂allyl | O | H, H |
| 4-CF₃ | H | CH₂ | CO₂CH₂CH₂Cl | O | H, H |
| 4-Cl | H | CH₂ | CO₂CH₂CH₂Cl | O | H, H |
| 4-Br | H | CH₂ | CO₂CH₂CH₂Cl | O | H, H |
| 4-CF₃ | H | CH₂ | Ph | O | H, H |
| 4-Cl | H | CH₂ | Ph | O | H, H |
| 4-Br | H | CH₂ | Ph | O | H, H |
| 4-CF₃ | 4-F | CH₂ | Ph | O | H, H |
| 4-Cl | 4-F | CH₂ | Ph | O | H, H |
| 4-Br | 4-F | CH₂ | Ph | O | H, H |
| 4-CF₃ | H | CH₂ | 4-Cl-Ph | O | H, H |
| 4-Cl | H | CH₂ | 4-Cl-Ph | O | H, H |
| 4-Br | H | CH₂ | 4-Cl-Ph | O | H, H |
| 4-CF₃ | 5-Cl | CH₂ | 4-Cl-Ph | O | H, H |
| 4-Cl | 5-Cl | CH₂ | 4-Cl-Ph | O | H, H |
| 4-Br | 5-Cl | CH₂ | 4-Cl-Ph | O | H, H |
| 4-CF₃ | H | CH₂ | 4-F-Ph | O | H, H |
| 4-Cl | H | CH₂ | 4-F-Ph | O | H, H |
| 4-Br | H | CH₂ | 4-F-Ph | O | H, H |
| 4-CF₃ | H | CH₂ | H | O | H, Me |
| 4-Cl | H | CH₂ | H | O | H, Me |
| 4-Br | H | CH₂ | H | O | H, Me |
| 4-CF₃ | 5-Cl | CH₂ | H | O | Me, Me |
| 4-Cl | 5-Cl | CH₂ | H | O | Me, Me |
| 4-Br | 5-Cl | CH₂ | H | O | Me, Me |
| 4-CF₃ | H | CH₂ | H | S | H, H |
| 4-Cl | H | CH₂ | H | S | H, H |
| 4-Br | H | CH₂ | H | S | H, H |
| 4-CF₃ | H | CH₂ | Me | S | H, H |
| 4-Cl | H | CH₂ | Me | S | H, H |
| 4-Br | H | CH₂ | Me | S | H, H |
| 4-CF₃ | H | CH₂ | CO₂Me | S | H, H |
| 4-Cl | H | CH₂ | CO₂Me | S | H, H |
| 4-Br | H | CH₂ | CO₂Me | S | H, H |
| 4-CF₃ | 5-Cl | CH₂ | H | S | H, H |
| 4-Cl | 5-Cl | CH₂ | H | S | H, H |

TABLE 4-continued

| $R_1$ | $R_2$ | A | B | X | $R_a^1, R_a^2$ |
|---|---|---|---|---|---|
| 4-Br | 5-Cl | $CH_2$ | H | S | H, H |
| 4-$CF_3$ | 5-Cl | $CH_2$ | Me | S | H, H |
| 4-Cl | 5-Cl | $CH_2$ | Me | S | H, H |
| 4-Br | 5-Cl | $CH_2$ | Me | S | H, H |
| 4-$CF_3$ | 5-Cl | $CH_2$ | $CO_2Me$ | S | H, H |
| 4-Cl | 5-Cl | $CH_2$ | $CO_2Me$ | S | H, H |
| 4-Br | 5-Cl | $CH_2$ | $CO_2Me$ | S | H, H |
| 4-$CF_3$ | H | O | H | O | H, H |
| 4-Cl | H | O | H | O | H, H |
| 4-Br | H | O | H | O | H, H |
| 4-$CF_3$ | 5-Cl | O | H | O | H, H |
| 4-Cl | 5-Cl | O | H | O | H, H |
| 4-Br | 5-Cl | O | H | O | H, H |
| 4-$CF_3$ | 4-F | O | H | O | H, H |
| 4-Cl | 4-F | O | H | O | H, H |
| 4-Br | 4-F | O | H | O | H, H |
| 4-$CF_3$ | 5-$CF_3$ | O | H | O | H, H |
| 4-Cl | 5-$CF_3$ | O | H | O | H, H |
| 4-Br | 5-$CF_3$ | O | H | O | H, H |
| 4-$CF_3$ | H | O | Me | O | H, H |
| 4-Cl | H | O | Me | O | H, H |
| 4-Br | H | O | Me | O | H, H |
| 4-$CF_3$ | 4-F | O | Me | O | H, H |
| 4-Cl | 4-F | O | Me | O | H, H |
| 4-Br | 4-F | O | Me | O | H, H |
| 4-$CF_3$ | 4-Cl | O | Me | O | H, H |
| 4-Cl | 4-Cl | O | Me | O | H, H |
| 4-Br | 4-Cl | O | Me | O | H, H |
| 4-$CF_3$ | 5-F | O | Me | O | H, H |
| 4-Cl | 5-F | O | Me | O | H, H |
| 4-Br | 5-F | O | Me | O | H, H |
| 4-$CF_3$ | 5-Cl | O | Me | O | H, H |
| 4-Cl | 5-Cl | O | Me | O | H, H |
| 4-Br | 5-Cl | O | Me | O | H, H |
| 4-$CF_3$ | H | O | $CO_2Me$ | O | H, H |
| 4-Cl | H | O | $CO_2Me$ | O | H, H |
| 4-Br | H | O | $CO_2Me$ | O | H, H |
| 4-$CF_3$ | 5-Cl | O | $CO_2Me$ | O | H, H |
| 4-Cl | 5-Cl | O | $CO_2Me$ | O | H, H |
| 4-Br | 5-Cl | O | $CO_2Me$ | O | H, H |
| 4-$CF_3$ | H | O | Ph | O | H, H |
| 4-Cl | H | O | Ph | O | H, H |
| 4-Br | H | O | Ph | O | H, H |
| 4-$CF_3$ | 5-Cl | O | Ph | O | H, H |
| 4-Cl | 5-Cl | O | Ph | O | H, H |
| 4-Br | 5-Cl | O | Ph |  | H, H |
| 4-$CF_3$ | H | O | H | O | Me, Me |
| 4-Cl | H | O | H | O | Me, Me |
| 4-Br | H | O | H | O | Me, Me |
| 4-$CF_3$ | H | O | H | O | H, Me |
| 4-Cl | H | O | H | O | H, Me |
| 4-Br | H | O | H | O | H, Me |
| 4-$CF_3$ | H | O | H | O | H, Ph |
| 4-Cl | H | O | H | O | H, Ph |
| 4-Br | H | O | H | O | H, Ph |
| 4-$CF_3$ | H | O | O | H | H, $CO_2Me$ |
| 4-Cl | H | O | H | O | H, $CO_2Me$ |
| 4-Br | H | O | H | O | H, $CO_2Me$ |
| 4-$CF_3$ | H | O | H | S | H, H |
| 4-Cl | H | O | H | S | H, H |
| 4-Br | H | O | H | S | H, H |
| 4-$CF_3$ | H | S | H | O | H, H |
| 4-Cl | H | S | H | O | H, H |
| 4-Br | H | S | H | O | H, H |
| 4-$CF_3$ | 5-Cl | S | H | O | H, H |
| 4-Cl | 5-Cl | S | H | O | H, H |
| 4-Br | 5-Cl | S | H | O | H, H |
| 4-$CF_3$ | 4-F | S | H | O | H, H |
| 4-Cl | 4-F | S | H | O | H, H |
| 4-Br | 4-F | S | H | O | H, H |
| 4-$CF_3$ | 5-$CF_3$ | S | H | O | H, H |
| 4-Cl | 5-$CF_3$ | S | H | O | H, H |
| 4-Br | 5-$CF_3$ | S | H | O | H, H |
| 4-$CF_3$ | H | S | Me | O | H, H |
| 4-Cl | H | S | Me | O | H, H |
| 4-Br | H | S | Me | O | H, H |
| 4-$CF_3$ | 4-F | S | Me | O | H, H |
| 4-Cl | 4-F | S | Me | O | H, H |
| 4-Br | 4-F | S | Me | O | H, H |
| 4-$CF_3$ | 4-Cl | S | Me | O | H, H |
| 4-Cl | 4-Cl | S | Me | O | H, H |
| 4-Br | 4-Cl | S | Me | O | H, H |
| 4-$CF_3$ | 5-F | S | Me | O | H, H |
| 4-Cl | 5-F | S | Me | O | H, H |
| 4-Br | 5-F | S | Me | O | H, H |
| 4-$CF_3$ | 5-Cl | S | Me | O | H, H |
| 4-Cl | 5-Cl | S | Me | O | H, H |
| 4-Br | 5-Cl | S | Me | O | H, H |
| 4-$CF_3$ | H | S | $CO_2Me$ | O | H, H |
| 4-Cl | H | S | $CO_2Me$ | O | H, H |
| 4-Br | H | S | $CO_2Me$ | O | H, H |
| 4-$CF_3$ | 5-Cl | S | $CO_2Me$ | O | H, H |
| 4-Cl | 5-Cl | S | $CO_2Me$ | O | H, H |
| 4-Br | 5-Cl | S | $CO_2Me$ | O | H, H |
| 4-$CF_3$ | H | S | Ph | O | H, H |
| 4-Cl | H | S | Ph | O | H, H |
| 4-Br | H | S | Ph | O | H, H |
| 4-$CF_3$ | 5-Cl | S | Ph | O | H, H |
| 4-Cl | 5-Cl | S | Ph | O | H, H |
| 4-Br | 5-Cl | S | Ph | O | H, H |
| 4-$CF_3$ | H | S | H | O | Me, Me |
| 4-Cl | H | S | H | O | Me, Me |
| 4-Br | H | S | H | O | Me, Me |
| 4-$CF_3$ | H | S | H | O | H, Me |
| 4-Cl | H | S | H | O | H, Me |
| 4-Br | H | S | H | O | H, Me |
| 4-$CF_3$ | H | S | H | O | H, Ph |
| 4-Cl | H | S | H | O | H, Ph |
| 4-Br | H | S | H | O | H, Ph |
| 4-$CF_3$ | H | S | H | O | H, $CO_2Me$ |
| 4-Cl | H | S | H | O | H, $CO_2Me$ |
| 4-Br | H | S | H | O | H, $CO_2Me$ |
| 4-$CF_3$ | H | S | H | S | H, H |
| 4-Cl | H | S | H | S | H, H |
| 4-Br | H | S | H | S | H,H |

TABLE 5

| $R_1$ | $R_2$ | A | B | X | $R_a^1, R_a^2$ |
|---|---|---|---|---|---|
| 4-$CF_3$ | H | $CH_2$ | H | O | H,H |
| 4-Cl | H | $CH_2$ | H | O | H,H |
| 4-Br | H | $CH_2$ | H | O | H,H |
| 4-$CF_3$ | 5-Cl | $CH_2$ | H | O | H,H |
| 4-Cl | 5-Cl | $CH_2$ | H | O | H,H |
| 4-Br | 5-Cl | $CH_2$ | H | O | H,H |
| 4-$CF_3$ | 5-F | $CH_2$ | H | O | H,H |
| 4-Cl | 5-F | $CH_2$ | H | O | H,H |
| 4-Br | 5-F | $CH_2$ | H | O | H,H |
| 4-$CF_3$ | 5-Me | $CH_2$ | H | O | H,H |
| 4-Cl | 5-Me | $CH_2$ | H | O | H,H |
| 4-Br | 5-Me | $CH_2$ | H | O | H,H |
| 4-$CF_3$ | H | $CH_2$ | Me | O | H,H |
| 4-Cl | H | $CH_2$ | Me | O | H,H |
| 4-Br | H | $CH_2$ | Me | O | H,H |
| 4-$CF_3$ | 5-Cl | $CH_2$ | Me | O | H,H |
| 4-Cl | 5-Cl | $CH_2$ | Me | O | H,H |
| 4-Br | 5-Cl | $CH_2$ | Me | O | H,H |
| 4-$CF_3$ | 5-F | $CH_2$ | Me | O | H,H |
| 4-Cl | 5-F | $CH_2$ | Me | O | H,H |
| 4-Br | 5-F | $CH_2$ | Me | O | H,H |
| 4-$CF_3$ | 5-Me | $CH_2$ | Me | O | H,H |
| 4-Cl | 5-Me | $CH_2$ | Me | O | H,H |
| 4-Br | 5-Me | $CH_2$ | Me | O | H,H |
| 4-$CF_3$ | H | $CH_2$ | Et | O | H,H |
| 4-Cl | H | $CH_2$ | Et | O | H,H |
| 4-Br | H | $CH_2$ | Et | O | H,H |
| 4-$CF_3$ | H | $CH_2$ | $CO_2Me$ | O | H,H |
| 4-Cl | H | $CH_2$ | $CO_2Me$ | O | H,H |
| 4-Br | H | $CH_2$ | $CO_2Me$ | O | H,H |
| 4-$CF_3$ | 5-F | $CH_2$ | $CO_2Me$ | O | H,H |
| 4-Cl | 5-F | $CH_2$ | $CO_2Me$ | O | H,H |
| 4-Br | 5-F | $CH_2$ | $CO_2Me$ | O |  |
| 4-$CF_3$ | 5-Cl | $CH_2$ | $CO_2Me$ | O | H,H |
| 4-Cl | 5-Cl | $CH_2$ | $CO_2Me$ | O | H,H |
| 4-Br | 5-Cl | $CH_2$ | $CO_2Me$ | O | H,H |
| 4-$CF_3$ | 5-Me | $CH_2$ | $CO_2Me$ | O | H,H |
| 4-Cl | 5-Me | $CH_2$ | $CO_2Me$ | O | H,H |
| 4-Br | 5-Me | $CH_2$ | $CO_2Me$ | O | H,H |
| 4-$CF_3$ | 5-Cl | $CH_2$ | $CO_2Et$ | O | H,H |
| 4-Cl | 5-Cl | $CH_2$ | $CO_2Et$ | O | H,H |
| 4-Br | 5-Cl | $CH_2$ | $CO_2Et$ | O | H,H |
| 4-$CF_3$ | H | $CH_2$ | Ph | O | H,H |

TABLE 5-continued

| R₁ | R₂ | A | B | X | Rₐ¹, Rₐ² |
|---|---|---|---|---|---|
| 4-Cl | H | CH₂ | Ph | O | H,H |
| 4-Br | H | CH₂ | Ph | O | H,H |
| 4-CF₃ | 5-Cl | CH₂ | Ph | O | H,H |
| 4-Cl | 5-Cl | CH₂ | Ph | O | H,H |
| 4-Br | 5-Cl | CH₂ | Ph | O | H,H |
| 4-CF₃ | H | CH₂ | 4-Cl—Ph | O | H,H |
| 4-Cl | H | CH₂ | 4-Cl—Ph | O | H,H |
| 4-Br | H | CH₂ | 4-Cl—Ph | O | H,H |
| 4-CF₃ | 5-Cl | CH₂ | 4-Cl—Ph | O | H,H |
| 4-Cl | 5-Cl | CH₂ | 4-Cl—Ph | O | H,H |
| 4-Br | 5-Cl | CH₂ | 4-Cl—Ph | O | H,H |
| 4-CF₃ | 5-CO₂Me | CH₂ | H | O | H,H |
| 4-CF₃ | H | O | H | O | H,H |
| 4-CF₃ | H | O | Me | O | H,H |
| 4-CF₃ | H | O | i-Pr | O | H,H |
| 4-CF₃ | H | O | CO₂Me | O | H,H |
| 4-CF₃ | H | O | Ph | O | H,H |
| 4-CF₃ | H | O | 4-F—Ph | O | H,H |
| 4-CF₃ | H | O | 4-Cl—Ph | O | H,H |
| 4-CF₃ | 5-F | O | H | O | H,H |
| 4-CF₃ | 5-F | O | Me | O | H,H |
| 4-CF₃ | 5-F | O | i-Pr | O | H,H |
| 4-CF₃ | 5-F | O | CO₂Me | O | H,H |
| 4-CF₃ | 5-F | O | Ph | O | H,H |
| 4-CF₃ | 5-F | O | 4-F—Ph | O | H,H |
| 4-CF₃ | 5-F | O | 4-Cl—Ph | O | H,H |
| 4-CF₃ | 5-Cl | O | H | O | H,H |
| 4-CF₃ | 5-Cl | O | Me | O | H,H |
| 4-CF₃ | 5-Cl | O | i-Pr | O | H,H |
| 4-CF₃ | 5-Cl | O | CO₂Me | O | H,H |
| 4-CF₃ | 5-Cl | O | Ph | O | H,H |
| 4-CF₃ | 5-Cl | O | 4-F—Ph | O | H,H |
| 4-CF₃ | 5-Cl | O | 4-Cl—Ph | O | H,H |
| 4-OCF₃ | H | O | H | O | H,H |
| 4-OCF₃ | H | O | Me | O | H,H |
| 4-OCF₃ | H | O | i-Pr | O | H,H |
| 4-OCF₃ | H | O | CO₂Me | O | H,H |
| 4-OCF₃ | H | O | Ph | O | H,H |
| 4-OCF₃ | H | O | 4-F—Ph | O | H,H |
| 4-OCF₃ | H | O | 4-Cl—Ph | O | H,H |
| 4-OCF₃ | 5-F | O | H | O | H,H |
| 4-OCF₃ | 5-F | O | Me | O | H,H |
| 4-OCF₃ | 5-F | O | i-Pr | O | H,H |
| 4-OCF₃ | 5-F | O | CO₂Me | O | H,H |
| 4-OCF₃ | 5-F | O | Ph | O | H,H |
| 4-OCF₃ | 5-F | O | 4-F—Ph | O | H,H |
| 4-OCF₃ | 5-F | O | 4-Cl—Ph | O | H,H |
| 4-OCF₃ | 5-Cl | O | H | O | H,H |
| 4-OCF₃ | 5-Cl | O | Me | O | H,H |
| 4-OCF₃ | 5-Cl | O | i-Pr | O | H,H |
| 4-OCF₃ | 5-Cl | O | CO₂Me | O | H,H |
| 4-OCF₃ | 5-Cl | O | Ph | O | H,H |
| 4-OCF₃ | 5-Cl | O | 4-F—Ph | O | H,H |
| 4-OCF₃ | 5-Cl | O | 4-Cl—Ph | O | H,H |
| 4-Br | H | O | H | O | H,H |
| 4-Br | H | O | Me | O | H,H |
| 4-Br | H | O | i-Pr | O | H,H |
| 4-Br | H | O | CO₂Me | O | H,H |
| 4-Br | H | O | Ph | O | H,H |
| 4-Br | H | O | 4-F—Ph | O | H,H |
| 4-Br | H | O | 4-Cl—Ph | O | H,H |
| 4-Br | 5-F | O | H | O | H,H |
| 4-Br | 5-F | O | Me | O | H,H |
| 4-Br | 5-F | O | i-Pr | O | H,H |
| 4-Br | 5-F | O | CO₂Me | O | H,H |
| 4-Br | 5-F | O | Ph | O | H,H |
| 4-Br | 5-F | O | 4-F—Ph | O | H,H |
| 4-Br | 5-F | O | 4-Cl—Ph | O | H,H |
| 4-Br | 5-Cl | O | H | O | H,H |
| 4-Br | 5-Cl | O | Me | O | H,H |
| 4-Br | 5-Cl | O | i-Pr | O | H,H |
| 4-Br | 5-Cl | O | CO₂Me | O | H,H |
| 4-Br | 5-Cl | O | Ph | O | H,H |
| 4-Br | 5-Cl | O | 4-F—Ph | O | H,H |
| 4-Br | 5-Cl | O | 4-Cl—Ph | O | H,H |
| 4-Cl | H | O | H | O | H,H |
| 4-Cl | H | O | Me | O | H,H |
| 4-Cl | H | O | i-Pr | O | H,H |
| 4-Cl | H | O | CO₂Me | O | H,H |
| 4-Cl | H | O | Ph | O | H,H |
| 4-Cl | H | O | 4-F—Ph | O | H,H |
| 4-Cl | H | O | 4-Cl—Ph | O | H,H |
| 4-Cl | 5-F | O | H | O | H,H |
| 4-Cl | 5-F | O | Me | O | H,H |
| 4-Cl | 5-F | O | i-Pr | O | H,H |
| 4-Cl | 5-F | O | CO₂Me | O | H,H |
| 4-Cl | 5-F | O | Ph | O | H,H |
| 4-Cl | 5-F | O | 4-F—Ph | O | H,H |
| 4-Cl | 5-F | O | 4-Cl—Ph | O | H,H |
| 4-Cl | 5-Cl | O | H | O | H,H |
| 4-Cl | 5-Cl | O | Me | O | H,H |
| 4-Cl | 5-Cl | O | i-Pr | O | H,H |
| 4-Cl | 5-Cl | O | CO₂Me | O | H,H |
| 4-Cl | 5-Cl | O | Ph | O | H,H |
| 4-Cl | 5-Cl | O | 4-F—Ph | O | H,H |
| 4-Cl | 5-Cl | O | 4-Cl—Ph | O | H,H |

TABLE 6

| R₁ | R₂ | A | B | X | Rₐ¹, Rₐ² |
|---|---|---|---|---|---|
| 4-CF₃ | H | CH₂ | H | O | H,H |
| 4-Cl | H | CH₂ | H | O | H,H |
| 4-Br | H | CH₂ | H | O | H,H |
| 4-CF₃ | 4-F | CH₂ | H | O | H,H |
| 4-Cl | 4-F | CH₂ | H | O | H,H |
| 4-Br | 4-F | CH₂ | H | O | H,H |
| 4-CF₃ | 4-Cl | CH₂ | H | O | H,H |
| 4-Cl | 4-Cl | CH₂ | H | O | H,H |
| 4-Br | 4-Cl | CH₂ | H | O | H,H |
| 4-CF₃ | 4-Me | CH₂ | H | O | H,H |
| 4-Cl | 4-Me | CH₂ | H | O | H,H |
| 4-Br | 4-Me | CH₂ | H | O | H,H |
| 4-CF₃ | H | CH₂ | Me | O | H,H |
| 4-Cl | H | CH₂ | Me | O | H,H |
| 4-Br | H | CH₂ | Me | O | H,H |
| 4-CF₃ | 4-F | CH₂ | Me | O | H,H |
| 4-Cl | 4-F | CH₂ | Me | O | H,H |
| 4-Br | 4-F | CH₂ | Me | O | H,H |
| 4-CF₃ | 4-Cl | CH₂ | Me | O | H,H |
| 4-Cl | 4-Cl | CH₂ | Me | O | H,H |
| 4-Br | 4-Cl | CH₂ | Me | O | H,H |
| 4-CF₃ | H | CH₂ | Et | O | H,H |
| 4-Cl | H | CH₂ | Et | O | H,H |
| 4-Br | H | CH₂ | Et | O | H,H |
| 4-CF₃ | 4-F | CH₂ | Et | O | H,H |
| 4-Cl | 4-F | CH₂ | Et | O | H,H |
| 4-Br | 4-F | CH₂ | Et | O | H,H |
| 4-CF₃ | H | CH₂ | CO₂Me | O | H,H |
| 4-Cl | H | CH₂ | CO₂Me | O | H,H |
| 4-Br | H | CH₂ | CO₂Me | O | H,H |
| 4-CF₃ | 4-F | CH₂ | CO₂Me |  | H,H |
| 4-Cl | 4-F | CH₂ | CO₂Me | O | H,H |
| 4-Br | 4-F | CH₂ | CO₂Me | O | H,H |
| 4-CF₃ | 4-Cl | CH₂ | CO₂Me |  | H,H |
| 4-Cl | 4-Cl | CH₂ | CO₂Me | O | H,H |
| 4-Br | 4-Cl | CH₂ | CO₂Me | O | H,H |
| 4-CF₃ | 4-Me | CH₂ | CO₂Me | O | H,H |
| 4-Cl | 4-Me | CH₂ | CO₂Me | O | H,H |
| 4-Br | 4-Me | CH₂ | CO₂Me | O | H,H |
| 4-CF₃ | H | CH₂ | CO₂Et | O | H,H |
| 4-Cl | H | CH₂ | CO₂Et | O | H,H |
| 4-Br | H | CH₂ | CO₂Et | O | H,H |
| 4-CF₃ | 4-Cl | CH₂ | Ph | O | H,H |
| 4-Cl | 4-Cl | CH₂ | Ph | O | H,H |
| 4-Br | 4-Cl | CH₂ | Ph | O | H,H |
| 4-CF₃ | H | CH₂ | Ph | O | H,H |
| 4-Cl | H | CH₂ | Ph | O | H,H |
| 4-Br | H | CH₂ | Ph | O | H,H |
| 4-CF₃ | 4-Cl | CH₂ | 4-F—Ph | O | H,H |
| 4-Cl | 4-Cl | CH₂ | 4-F—Ph | O | H,H |
| 4-Br | 4-Cl | CH₂ | 4-F—Ph | O | H,H |
| 4-CF₃ | H | CH₂ | 4-F—Ph | O | H,H |
| 4-Cl | H | CH₂ | 4-F—Ph | O | H,H |
| 4-Br | H | CH₂ | 4-F—Ph | O | H,H |

TABLE 7

| R₁ | R₂ | A | B | X | Rₐ¹, Rₐ² |
|---|---|---|---|---|---|
| 4-CF₃ | H | CH₂ | H | O | H,H |
| 4-Cl | H | CH₂ | H | O | H,H |
| 4-Br | H | CH₂ | H | O | H,H |

TABLE 7-continued

| R₁ | R₂ | A | B | X | Rₐ¹, Rₐ² |
|---|---|---|---|---|---|
| 4-CF₃ | 4-F | CH₂ | H | O | H,H |
| 4-Cl | 4-F | CH₂ | H | O | H,H |
| 4-Br | 4-F | CH₂ | H | O | H,H |
| 4-CF₃ | 5-Cl | CH₂ | H | O | H,H |
| 4-Cl | 5-Cl | CH₂ | H | O | H,H |
| 4-Br | 5-Cl | CH₂ | H | O | H,H |
| 4-CF₃ | 5-F | CH₂ | H | O | H,H |
| 4-Cl | 5-F | CH₂ | H | O | H,H |
| 4-Br | 5-F | CH₂ | H | O | H,H |
| 4-CF₃ | H | CH₂ | Me | O | H,H |
| 4-Cl | H | CH₂ | Me | O | H,H |
| 4-Br | H | CH₂ | Me | O | H,H |
| 4-CF₃ | 4-F | CH₂ | Me | O | H,H |
| 4-Cl | 4-F | CH₂ | Me | O | H,H |
| 4-Br | 4-F | CH₂ | Me | O | H,H |
| 4-CF₃ | 4-Cl | CH₂ | Me | O | H,H |
| 4-Cl | 4-Cl | CH₂ | Me | O | H,H |
| 4-Br | 4-Cl | CH₂ | Me | O | H,H |
| 4-CF₃ | 5-F | CH₂ | Me | O | H,H |
| 4-Cl | 5-F | CH₂ | Me | O | H,H |
| 4-Br | 5-F | CH₂ | Me | O | H,H |
| 4-CF₃ | 5-Cl | CH₂ | Me | O | H,H |
| 4-Cl | 5-Cl | CH₂ | Me | O | H,H |
| 4-Br | 5-Cl | CH₂ | Me | O | H,H |
| 4-CF₃ | H | CH₂ | CO₂Me | O | H,H |
| 4-Cl | H | CH₂ | CO₂Me | O | H,H |
| 4-Br | H | CH₂ | CO₂Me | O | H,H |
| 4-CF₃ | 4-F | CH₂ | CO₂Me | O | H,H |
| 4-Cl | 4-F | CH₂ | CO₂Me | O | H,H |
| 4-Br | 4-F | CH₂ | CO₂Me | O | H,H |
| 4-CF₃ | 4-Cl | CH₂ | CO₂Me | O | H,H |
| 4-Cl | 4-Cl | CH₂ | CO₂Me | O | H,H |
| 4-Br | 4-Cl | CH₂ | CO₂Me | O | H,H |
| 4-CF₃ | 5-F | CH₂ | CO₂Me | O | H,H |
| 4-Cl | 5-F | CH₂ | CO₂Me | O | H,H |
| 4-Br | 5-F | CH₂ | CO₂Me | O | H,H |
| 4-CF₃ | 5-Cl | CH₂ | CO₂Me | O | H,H |
| 4-Cl | 5-Cl | CH₂ | CO₂Me | O | H,H |
| 4-Br | 5-Cl | CH₂ | CO₂Me | O | H,H |
| 4-CF₃ | H | CH₂ | Ph | O | H,H |
| 4-Cl | H | CH₂ | Ph | O | H,H |
| 4-Br | H | CH₂ | Ph | O | H,H |
| 4-CF₃ | 4-F | CH₂ | 4-F—Ph | O | H,H |
| 4-Cl | 4-F | CH₂ | 4-F—Ph | O | H,H |
| 4-Br | 4-F | CH₂ | 4-F—Ph | O | H,H |
| 4-CF₃ | 5-Cl | CH₂ | 4-Cl—Ph | O | H,H |
| 4-Cl | 5-Cl | CH₂ | 4-Cl—Ph | O | H,H |
| 4-Br | 5-Cl | CH₂ | 4-Cl—Ph | O | H,H |
| 4-CF₃ | 5-F | CH₂ | 4-Cl—Ph | O | H,H |
| 4-Cl | 5-F | CH₂ | 4-Cl—Ph | O | H,H |
| 4-Br | 5-F | CH₂ | 4-Cl—Ph | O | H,H |
| 4-CF₃ | H | O | H | O | H,H |
| 4-CF₃ | H | O | Me | O | H,H |
| 4-CF₃ | H | O | i-Pr | O | H,H |
| 4-CF₃ | H | O | CO₂Me | O | H,H |
| 4-CF₃ | H | O | Ph | O | H,H |
| 4-CF₃ | H | O | 4-F—Ph | O | H,H |
| 4-CF₃ | H | O | 4-Cl—Ph | O | H,H |
| 4-CF₃ | 5-F | O | H | O | H,H |
| 4-CF₃ | 5-F | O | Me | O | H,H |
| 4-CF₃ | 5-F | O | i-Pr | O | H,H |
| 4-CF₃ | 5-F | O | CO₂Me | O | H,H |
| 4-CF₃ | 5-F | O | Ph | O | H,H |
| 4-CF₃ | 5-F | O | 4-F—Ph | O | H,H |
| 4-CF₃ | 5-F | O | 4-Cl—Ph | O | H,H |
| 4-CF₃ | 5-Cl | O | H | O | H,H |
| 4-CF₃ | 5-Cl | O | Me | O | H,H |
| 4-CF₃ | 5-Cl | O | i-Pr | O | H,H |
| 4-CF₃ | 5-Cl | O | CO₂Me | O | H,H |
| 4-CF₃ | 5-Cl | O | Ph | O | H,H |
| 4-CF₃ | 5-Cl | O | 4-F—Ph | O | H,H |
| 4-CF₃ | 5-Cl | O | 4-Cl—Ph | O | H,H |
| 4-OCF₃ | H | O | H | O | H,H |
| 4-OCF₃ | H | O | Me | O | H,H |
| 4-OCF₃ | H | O | i-Pr | O | H,H |
| 4-OCF₃ | H | O | CO₂Me | O | H,H |
| 4-OCF₃ | H | O | Ph | O | H,H |
| 4-OCF₃ | H | O | 4-F—Ph | O | H,H |
| 4-OCF₃ | H | O | 4-Cl—Ph | O | H,H |
| 4-OCF₃ | 5-F | O | H | O | H,H |
| 4-OCF₃ | 5-F | O | Me | O | H,H |
| 4-OCF₃ | 5-F | O | i-Pr | O | H,H |
| 4-OCF₃ | 5-F | O | CO₂Me | O | H,H |
| 4-OCF₃ | 5-F | O | Ph | O | H,H |
| 4-OCF₃ | 5-F | O | 4-F—Ph | O | H,H |
| 4-OCF₃ | 5-F | O | 4-Cl—Ph | O | H,H |
| 4-OCF₃ | 5-Cl | O | H | O | H,H |
| 4-OCF₃ | 5-Cl | O | Me | O | H,H |
| 4-OCF₃ | 5-Cl | O | i-Pr | O | H,H |
| 4-OCF₃ | 5-Cl | O | CO₂Me | O | H,H |
| 4-OCF₃ | 5-Cl | O | Ph | O | H,H |
| 4-OCF₃ | 5-Cl | O | 4-F—Ph | O | H,H |
| 4-OCF₃ | 5-Cl | O | 4-Cl—Ph | O | H,H |
| 4-Br | H | O | H | O | H,H |
| 4-Br | H | O | Me | O | H,H |
| 4-Br | H | O | i-Pr | O | H,H |
| 4-Br | H | O | CO₂Me | O | H,H |
| 4-Br | H | O | Ph | O | H,H |
| 4-Br | H | O | 4-F—Ph | O | H,H |
| 4-Br | H | O | 4-Cl—Ph | O | H,H |
| 4-Br | 5-F | O | H | O | H,H |
| 4-Br | 5-F | O | Me | O | H,H |
| 4-Br | 5-F | O | i-Pr | O | H,H |
| 4-Br | 5-F | O | CO₂Me | O | H,H |
| 4-Br | 5-F | O | Ph | O | H,H |
| 4-Br | 5-F | O | 4-F—Ph | O | H,H |
| 4-Br | 5-F | O | 4-Cl—Ph | O | H,H |
| 4-Br | 5-Cl | O | H | O | H,H |
| 4-Br | 5-Cl | O | Me | O | H,H |
| 4-Br | 5-Cl | O | i-Pr | O | H,H |
| 4-Br | 5-Cl | O | CO₂Me | O | H,H |
| 4-Br | 5-Cl | O | Ph | O | H,H |
| 4-Br | 5-Cl | O | 4-F—Ph | O | H,H |
| 4-Br | 5-Cl | O | 4-Cl—Ph | O | H,H |
| 4-Cl | H | O | H | O | H,H |
| 4-Cl | H | O | Me | O | H,H |
| 4-Cl | H | O | i-Pr | O | H,H |
| 4-Cl | H | O | CO₂Me | O | H,H |
| 4-Cl | H | O | Ph | O | H,H |
| 4-Cl | H | O | 4-F—Ph | O | H,H |
| 4-Cl | H | O | 4-Cl—Ph | O | H,H |
| 4-Cl | 5-F | O | H | O | H,H |
| 4-Cl | 5-F | O | Me | O | H,H |
| 4-Cl | 5-F | O | i-Pr | O | H,H |
| 4-Cl | 5-F | O | CO₂Me | O | H,H |
| 4-Cl | 5-F | O | Ph | O | H,H |
| 4-Cl | 5-F | O | 4-F—Ph | O | H,H |
| 4-Cl | 5-F | O | 4-Cl—Ph | O | H,H |
| 4-Cl | 5-Cl | O | H | O | H,H |
| 4-Cl | 5-Cl | O | Me | O | H,H |
| 4-Cl | 5-Cl | O | i-Pr | O | H,H |
| 4-Cl | 5-Cl | O | CO₂Me | O | H,H |
| 4-Cl | 5-Cl | O | Ph | O | H,H |
| 4-Cl | 5-Cl | O | 4-F—Ph | O | H,H |
| 4-Cl | 5-Cl | O | 4-Cl—Ph | O | H,H |

TABLE 8

| R₁ | R₂ | A | B | X | rₐ¹, rₐ² |
|---|---|---|---|---|---|
| 4-CF₃ | H | CH₂ | H | O | H,H |
| 4-Cl | H | CH₂ | H | O | H,H |
| 4-Br | H | CH₂ | H | O | H,H |
| 4-CF₃ | 5-Cl | CH₂ | H | O | H,H |
| 4-Cl | 5-Cl | CH₂ | H | O | H,H |
| 4-Br | 5-Cl | CH₂ | H | O | H,H |
| 4-CF₃ | 5-F | CH₂ | H | O | H,H |
| 4-Cl | 5-F | CH₂ | H | O | H,H |
| 4-Br | 5-F | CH₂ | H | O | H,H |
| 4-CF₃ | 5-Me | CH₂ | H | O | H,H |
| 4-Cl | 5-Me | CH₂ | H | O | H,H |
| 4-Br | 5-Me | CH₂ | H | O | H,H |
| 4-CF₃ | H | CH₂ | Me | O | H,H |
| 4-Cl | H | CH₂ | Me | O | H,H |
| 4-Br | H | CH₂ | Me | O | H,H |
| 4-CF₃ | 5-Cl | CH₂ | Me | O | H,H |
| 4-Cl | 5-Cl | CH₂ | Me | O | H,H |
| 4-Br | 5-Cl | CH₂ | Me | O | H,H |
| 4-CF₃ | 5-F | CH₂ | Me | O | H,H |
| 4-Cl | 5-F | CH₂ | Me | O | H,H |
| 4-Br | 5-F | CH₂ | Me | O | H,H |

TABLE 8-continued

| R₁ | R₂ | A | B | X | $R_a^1, R_a^2$ |
|---|---|---|---|---|---|
| 4-CF₃ | 5-Me | CH₂ | Me | O | H,H |
| 4-Cl | 5-Me | CH₂ | Me | O | H,H |
| 4-Br | 5-Me | CH₂ | Me | O | H,H |
| 4-CF₃ | H | CH₂ | Et | O | H,H |
| 4-Cl | H | CH₂ | Et | O | H,H |
| 4-Br | H | CH₂ | Et | O | H,H |
| 4-CF₃ | H | CH₂ | CO₂Me | O | H,H |
| 4-Cl | H | CH₂ | CO₂Me | O | H,H |
| 4-Br | H | CH₂ | CO₂Me | O | H,H |
| 4-CF₃ | 5-F | CH₂ | CO₂Me | O | H,H |
| 4-Cl | 5-F | CH₂ | CO₂Me | O | H,H |
| 4-Br | 5-F | CH₂ | CO₂Me | O | H,H |
| 4-CF₃ | 5-Cl | CH₂ | CO₂Me | O | H,H |
| 4-Cl | 5-Cl | CH₂ | CO₂Me | O | H,H |
| 4-Br | 5-Cl | CH₂ | CO₂Me | O | H,H |
| 4-CF₃ | 5-Me | CH₂ | CO₂Me | O | H,H |
| 4-Cl | 5-Me | CH₂ | CO₂Me | O | H,H |
| 4-Br | 5-Me | CH₂ | CO₂Me | O | H,H |
| 4-CF₃ | 5-Cl | CH₂ | CO₂Et | O | H,H |
| 4-Cl | 5-Cl | CH₂ | CO₂Et | O | H,H |
| 4-Br | 5-Cl | CH₂ | CO₂Et | O | H,H |
| 4-CF₃ | H | CH₂ | Ph | O | H,H |
| 4-Cl | H | CH₂ | Ph | O | H,H |
| 4-Br | H | CH₂ | Ph | O | H,H |
| 4-CF₃ | 5-Cl | CH₂ | Ph | O | H,H |
| 4-Cl | 5-Cl | CH₂ | Ph | O | H,H |
| 4-Br | 5-Cl | CH₂ | Ph | O | H,H |
| 4-CF₃ | H | CH₂ | 4-Cl—Ph | O | H,H |
| 4-Cl | H | CH₂ | 4-Cl—Ph | O | H,H |
| 4-Br | H | CH₂ | 4-Cl—Ph | O | H,H |
| 4-CF₃ | 5-Cl | CH₂ | 4-Cl—Ph | O | H,H |
| 4-Cl | 5-Cl | CH₂ | 4-Cl—Ph | O | H,H |
| 4-Br | 5-Cl | CH₂ | 4-Cl—Ph | O | H,H |

TABLE 9

| R₁ | R₂ | A | B | X | $R_a^1, R_a^2$ |
|---|---|---|---|---|---|
| 4-CF₃ | H | CH₂ | H | O | H,H |
| 4-Cl | H | CH₂ | H | O | H,H |
| 4-Br | H | CH₂ | H | O | H,H |
| 4-CF₃ | 4-F | CH₂ | H | O | H,H |
| 4-Cl | 4-F | CH₂ | H | O | H,H |
| 4-Br | 4-F | CH₂ | H | O | H,H |
| 4-CF₃ | 4-Cl | CH₂ | H | O | H,H |
| 4-Cl | 4-Cl | CH₂ | H | O | H,H |
| 4-Br | 4-Cl | CH₂ | H | O | H,H |
| 4-CF₃ | 4-Me | CH₂ | H | O | H,H |
| 4-Cl | 4-Me | CH₂ | H | O | H,H |
| 4-Br | 4-Me | CH₂ | H | O | H,H |
| 4-CF₃ | H | CH₂ | Me | O | H,H |
| 4-Cl | H | CH₂ | Me | O | H,H |
| 4-Br | H | CH₂ | Me | O | H,H |
| 4-CF₃ | 4-F | CH₂ | Me | O | H,H |
| 4-Cl | 4-F | CH₂ | Me | O | H,H |
| 4-Br | 4-F | CH₂ | Me | O | H,H |
| 4-CF₃ | 4-Cl | CH₂ | Me | O | H,H |
| 4-Cl | 4-Cl | CH₂ | Me | O | H,H |
| 4-Br | 4-Cl | CH₂ | Me | O | H,H |
| 4-CF₃ | H | CH₂ | Et | O | H,H |
| 4-Cl | H | CH₂ | Et | O | H,H |
| 4-Br | H | CH₂ | Et | O | H,H |
| 4-CF₃ | 4-F | CH₂ | Et | O | H,H |
| 4-Cl | 4-F | CH₂ | Et | O | H,H |
| 4-Br | 4-F | CH₂ | Et | O | H,H |
| 4-CF₃ | H | CH₂ | CO₂Me | O | H,H |
| 4-Cl | H | CH₂ | CO₂Me | O | H,H |
| 4-Br | H | CH₂ | CO₂Me | O | H,H |
| 4-CF₃ | 4-F | CH₂ | CO₂Me | O | H,H |
| 4-Cl | 4-F | CH₂ | CO₂Me | O | H,H |
| 4-Br | 4-F | CH₂ | CO₂Me | O | H,H |
| 4-CF₃ | 4-Cl | CH₂ | CO₂Me | O | H,H |
| 4-Cl | 4-Cl | CH₂ | CO₂Me | O | H,H |
| 4-Br | 4-Cl | CH₂ | CO₂Me | O | H,H |
| 4-CF₃ | 4-Me | CH₂ | CO₂Me | O | H,H |
| 4-Cl | 4-Me | CH₂ | CO₂Me | O | H,H |
| 4-Br | 4-Me | CH₂ | CO₂Me | O | H,H |
| 4-CF₃ | H | CH₂ | CO₂Et | O | H,H |
| 5-Cl | H | CH₂ | CO₂Et | O | H,H |
| 4-Br | H | CH₂ | CO₂Et | O | H,H |

TABLE 9-continued

| R₁ | R₂ | A | B | X | $R_a^1, R_a^2$ |
|---|---|---|---|---|---|
| 4-CF₃ | 4-Cl | CH₂ | Ph | O | H,H |
| 4-Cl | 4-Cl | CH₂ | Ph | O | H,H |
| 4-Br | 4-Cl | CH₂ | Ph | O | H,H |
| 4-CF₃ | H | CH₂ | Ph | O | H,H |
| 4-Cl | H | CH₂ | Ph | O | H,H |
| 4-Br | H | CH₂ | Ph | O | H,H |
| 4-CF₃ | 4-Cl | CH₂ | 4-F—Ph | O | H,H |
| 4-Cl | 4-Cl | CH₂ | 4-F—Ph | O | H,H |
| 4-Br | 4-Cl | CH₂ | 4-F—Ph | O | H,H |
| 4-CF₃ | H | CH₂ | 4-F—Ph | O | H,H |
| 4-Cl | H | CH₂ | 4-F—Ph | O | H,H |
| 4-Br | H | CH₂ | 4-F—Ph | O | H,H, |

TABLE 10

| R₁ | R₂ | A | B | X | $R_a^1, R_a^2$ |
|---|---|---|---|---|---|
| 4-CF₃ | H | CH₂ | H | O | H,H |
| 4-Cl | H | CH₂ | H | O | H,H |
| 4-Br | H | CH₂ | H | O | H,H |
| 4-CF₃ | 4-F | CH₂ | H | O | H,H |
| 4-Cl | 4-F | CH₂ | H | O | H,H |
| 4-Br | 4-F | CH₂ | H | O | H,H |
| 4-CF₃ | 5-Cl | CH₂ | H | O | H,H |
| 4-Cl | 5-Cl | CH₂ | H | O | H,H |
| 4-Br | 5-Cl | CH₂ | H | O | H,H |
| 4-CF₃ | 5F | CH₂ | H | O | H,H |
| 4-Cl | 5-F | CH₂ | H | O | H,H |
| 4-Br | 5-F | CH₂ | H | O | H,H |
| 4-CF₃ | H | CH₂ | Me | O | H,H |
| 4-Cl | H | CH₂ | Me | O | H,H |
| 4-Br | H | CH₂ | Me | O | H,H |
| 4-CF₃ | 4-F | CH₂ | Me | O | H,H |
| 4-Cl | 4-F | CH₂ | Me | O | H,H |
| 4-Br | 4-F | CH₂ | Me | O | H,H |
| 4-CF₃ | 4-Cl | CH₂ | Me | O | H,H |
| 4-Cl | 4-Cl | CH₂ | Me | O | H,H |
| 4-Br | 4-Cl | CH₂ | Me | O | H,H |
| 4-CF₃ | 5-F | CH₂ | Me | O | H,H |
| 4-Cl | 5-F | CH₂ | Me | O | H,H |
| 4-Br | 5-F | CH₂ | Me | O | H,H |
| 4-CF₃ | 5-Cl | CH₂ | Me | O | H,H |
| 4-Cl | 5-Cl | CH₂ | Me | O | H,H |
| 4-Br | 5-Cl | CH₂ | Me | O | H,H |
| 4-CF₃ | H | CH₂ | CO₂Me | O | H,H |
| 4-Cl | H | CH₂ | CO₂Me | O | H,H |
| 4-Br | H | CH₂ | CO₂Me | O | H,H |
| 4-CF₃ | 4-F | CH₂ | CO₂Me | O | H,H |
| 4-Cl | 4-F | CH₂ | CO₂Me | O | H,H |
| 4-Br | 4-F | CH₂ | CO₂Me | O | H,H |
| 4-CF₃ | 4-Cl | CH₂ | CO₂Me | O | H,H |
| 4-Cl | 4-Cl | CH₂ | CO₂Me | O | H,H |
| 4-Br | 4-Cl | CH₂ | CO₂Me | O | H,H |
| 4-CF₃ | 5-F | CH₂ | CO₂Me | O | H,H |
| 4-Cl | 5-F | CH₂ | CO₂Me | O | H,H |
| 4-Br | 5-F | CH₂ | CO₂Me | O | H,H |
| 4-CF₃ | 5-Cl | CH₂ | CO₂Me | O | H,H |
| 4-Cl | 5-Cl | CH₂ | CO₂Me | O | H,H |
| 4-Br | 5-Cl | CH₂ | CO₂Me | O | H,H |
| 4-CF₃ | H | CH₂ | Ph | O | H,H |
| 4-Cl | H | CH₂ | Ph | O | H,H |
| 4-Br | H | CH₂ | Ph | O | H,H |
| 4-CF₃ | 4-F | CH₂ | 4-F—Ph | O | H,H |
| 4-Cl | 4-F | CH₂ | 4-F—Ph | O | H,H |
| 4-Br | 4-F | CH₂ | 4-F—Ph | O | H,H |
| 4-CF₃ | 5-Cl | CH₂ | 4-Cl—Ph | O | H,H |
| 4-Cl | 5-Cl | CH₂ | 4-Cl—Ph | O | H,H |
| 4-Br | 5-Cl | CH₂ | 4-Cl—Ph | O | H,H |
| 4-CF₃ | 5-F | CH₂ | 4-Cl-Ph | O | H,H |
| 4-Cl | 5-F | CH₂ | 4-Cl-Ph | O | H,H |
| 4-Br | 5-F | CH₂ | 4-Cl-Ph | O | H,H |

TABLE 11

| R₁ | R₂ | A | B | Q | Y |
|---|---|---|---|---|---|
| 4-CF₃ | H | CH₂ | H | Q-1 | Me |
| 4-Cl | H | CH₂ | H | Q-1 | Me |
| 4-Br | H | CH₂ | H | Q-1 | Me |
| 4-CF₃ | 5-Cl | CH₂ | Me | Q-1 | Me |

TABLE 11-continued

| R₁ | R₂ | A | B | Q | Y |
|---|---|---|---|---|---|
| 4-Cl | 5-Cl | CH₂ | Me | Q-1 | Me |
| 4-Br | 5-Cl | CH₂ | Me | Q-1 | Me |
| 4-CF₃ | H | CH₂ | Me | Q-1 | Me |
| 4-Cl | H | CH₂ | Me | Q-1 | Me |
| 4-Br | H | CH₂ | Me | Q-1 | Me |
| 4-CF₃ | H | CH₂ | Me | Q-1 | C(O)Me |
| 4-Cl | H | CH₂ | Me | Q-1 | C(O)Me |
| 4-Br | H | CH₂ | Me | Q-1 | C(O)Me |
| 4-CF₃ | H | CH₂ | Me | Q-1 | CO₂Me |
| 4-Cl | H | CH₂ | Me | Q-1 | CO₂Me |
| 4-Br | H | CH₂ | Me | Q-1 | CO₂Me |
| 4-CF₃ | 5-Cl | CH₂ | Me | Q-1 | Me |
| 4-Cl | 5-Cl | CH₂ | Me | Q-1 | Me |
| 4-Br | 5-Cl | CH₂ | Me | Q-1 | Me |
| 4-CF₃ | 5-Cl | CH₂ | Me | Q-1 | C(O)Me |
| 4-Cl | 5-Cl | CH₂ | Me | Q-1 | C(O)Me |
| 4-Br | 5-Cl | CH₂ | Me | Q-1 | C(O)Me |
| 4-CF₃ | 5-Cl | CH₂ | Me | Q-1 | CO₂Me |
| 4-Cl | 5-Cl | CH₂ | Me | Q-1 | CO₂Me |
| 4-Br | 5-Cl | CH₂ | Me | Q-1 | CO₂Me |
| 4-CF₃ | 5-F | CH₂ | Me | Q-1 | CO₂Me |
| 4-Cl | 5-F | CH₂ | Me | Q-1 | CO₂Me |
| 4-Br | 5-F | CH₂ | Me | Q-1 | CO₂Me |
| 4-CF₃ | H | CH₂ | CO₂Me | Q-1 | C(O)Me |
| 4-Cl | H | CH₂ | CO₂Me | Q-1 | C(O)Me |
| 4-Br | H | CH₂ | CO₂Me | Q-1 | C(O)Me |
| 4-CF₃ | H | CH₂ | CO₂Me | Q-1 | Me |
| 4-Cl | H | CH₂ | CO₂Me | Q-1 | Me |
| 4-Br | H | CH₂ | CO₂Me | Q-1 | Me |
| 4-CF₃ | H | CH₂ | CO₂Me | Q-1 | CO₂Me |
| 4-Cl | H | CH₂ | CO₂Me | Q-1 | CO₂Me |
| 4-Br | H | CH₂ | CO₂Me | Q-1 | CO₂Me |
| 4-CF₃ | 5-Cl | CH₂ | CO₂Me | Q-1 | C(O)Me |
| 4-Cl | 5-Cl | CH₂ | CO₂Me | Q-1 | C(O)Me |
| 4-Br | 5-Cl | CH₂ | CO₂Me | Q-1 | C(O)Me |
| 4-CF₃ | 5-Cl | CH₂ | CO₂Me | Q-1 | CO₂Me |
| 4-Cl | 5-Cl | CH₂ | CO₂Me | Q-1 | CO₂Me |
| 4-Br | 5-Cl | CH₂ | CO₂Me | Q-1 | CO₂Me |
| 4-CF₃ | H | CH₂ | Ph | Q-1 | C(O)Me |
| 4-Cl | H | CH₂ | Ph | Q-1 | C(O)Me |
| 4-Br | H | CH₂ | Ph | Q-1 | C(O)Me |
| 4-CF₃ | 5-Cl | CH₂ | Ph | Q-1 | C(O)Me |
| 4-Cl | 5-Cl | CH₂ | Ph | Q-1 | C(O)Me |
| 4-Br | 5-Cl | CH₂ | Ph | Q-1 | C(O)Me |
| 4-CF₃ | H | CH₂ | 4-Cl—Ph | Q-1 | C(O)Me |
| 4-Cl | H | CH₂ | 4-Cl—Ph | Q-1 | C(O)Me |
| 4-Br | H | CH₂ | 4-Cl—Ph | Q-1 | C(O)Me |
| 4-CF₃ | 5-Cl | CH₂ | 4-Cl—Ph | Q-1 | C(O)Me |
| 4-Cl | 5-Cl | CH₂ | 4-Cl—Ph | Q-1 | C(O)Me |
| 4-Br | 5-Cl | CH₂ | 4-Cl—Ph | Q-1 | C(O)Me |
| 4-CF₃ | H | CH₂ | H | Q-2 | Me |
| 4-Cl | H | CH₂ | H | Q-2 | Me |
| 4-Br | H | CH₂ | H | Q-2 | Me |
| 4-CF₃ | H | CH₂ | H | Q-2 | C(O)Me |
| 4-Cl | H | CH₂ | H | Q-2 | C(O)Me |
| 4-Br | H | CH₂ | H | Q-2 | C(O)Me |
| 4-CF₃ | H | CH₂ | CO₂Me | Q-2 | Me |
| 4-Cl | H | CH₂ | CO₂Me | Q-2 | Me |
| 4-Br | H | CH₂ | CO₂Me | Q-2 | Me |
| 4-CF₃ | H | CH₂ | CO₂Me | Q-2 | C(O)Me |
| 4-Cl | H | CH₂ | CO₂Me | Q-2 | C(O)Me |
| 4-Br | H | CH₂ | CO₂Me | Q-2 | C(O)Me |
| 4-CF₃ | H | CH₂ | CO₂Me | Q-2 | CO₂Me |
| 4-Cl | H | CH₂ | CO₂Me | Q-2 | CO₂Me |
| 4-Br | H | CH₂ | CO₂Me | Q-2 | CO₂Me |
| 4-CF₃ | 4-F | CH₂ | H | Q-2 | Me |
| 4-Cl | 4-F | CH₂ | H | Q-2 | Me |
| 4-Br | 4-F | CH₂ | H | Q-2 | Me |
| 4-CF₃ | 4-F | CH₂ | H | Q-2 | C(O)Me |
| 4-Cl | 4-F | CH₂ | H | Q-2 | C(O)Me |
| 4-Br | 4-F | CH₂ | H | Q-2 | C(O)Me |
| 4-CF₃ | 4-F | CH₂ | CO₂Me | Q-2 | CO₂Me |
| 4-Cl | 4-F | CH₂ | CO₂Me | Q-2 | CO₂Me |
| 4-Br | 4-F | CH₂ | CO₂Me | Q-2 | CO₂Me |
| 4-CF₃ | 4-F | CH₂ | CO₂Me | Q-2 | C(O)Me |
| 4-Cl | 4-F | CH₂ | CO₂Me | Q-2 | Ac |
| 4-Br | 4-F | CH₂ | CO₂Me | Q-2 | Ac |
| 4-CF₃ | H | CH₂ | H | Q-3 | Me |
| 4-Cl | H | CH₂ | H | Q-3 | Me |
| 4-Br | H | CH₂ | H | Q-3 | Ac |
| 4-CF₃ | H | CH₂ | H | Q-3 | C(O)Me |
| 4-Cl | H | CH₂ | H | Q-3 | CO₂Me |
| 4-Br | H | CH₂ | H | Q-3 | CO₂Me |
| 4-CF₃ | 5-Cl | CH₂ | H | Q-3 | Me |
| 4-Cl | 5-Cl | CH₂ | H | Q-3 | Me |
| 4-Br | 5-Cl | CH₂ | H | Q-3 | C(O)Me |
| 4-CF₃ | 5-Cl | CH₂ | H | Q-3 | CO₂Me |
| 4-Cl | 5-Cl | CH₂ | H | Q-3 | CO₂Me |
| 4-CF₃ | H | CH₂ | CO₂Me | Q-3 | Me |
| 4-Cl | H | CH₂ | CO₂Me | Q-3 | Me |
| 4-Br | H | CH₂ | CO₂Me | Q-3 | C(O)Me |
| 4-CF₃ | H | CH₂ | CO₂Me | Q-3 | C(O)Me |
| 4-Cl | H | CH₂ | CO₂Me | Q-3 | C(O)Me |
| 4-Br | H | CH₂ | CO₂Me | Q-3 | C(O)Me |
| 4-CF₃ | H | CH₂ | CO₂Me | Q-3 | CO₂Me |
| 4-Cl | H | CH₂ | CO₂Me | Q-3 | CO₂Me |
| 4-Br | H | CH₂ | CO₂Me | Q-3 | CO₂Me |
| 4-CF₃ | 5-Cl | CH₂ | CO₂Me | Q-3 | Me |
| 4-Cl | 5-Cl | CH₂ | CO₂Me | Q-3 | Me |
| 4-Br | 5-Cl | CH₂ | CO₂Me | Q-3 | Me |
| 4-CF₃ | 5-Cl | CH₂ | CO₂Me | Q-3 | C(O)Me |
| 4-Cl | 5-Cl | CH₂ | CO₂Me | Q-3 | C(O)Me |
| 4-Br | 5-Cl | CH₂ | CO₂Me | Q-3 | C(O)Me |
| 4-CF₃ | H | CH₂ | H | Q-5 | C(O)Me |
| 4-Cl | H | CH₂ | H | Q-5 | C(O)Me |
| 4-Br | H | CH₂ | H | Q-5 | C(O)Me |
| 4-CF₃ | H | CH₂ | H | Q-5 | CO₂Me |
| 4-Cl | H | CH₂ | H | Q-5 | CO₂Me |
| 4-Br | H | CH₂ | H | Q-5 | CO₂Me |
| 4-CF₃ | 5-Cl | CH₂ | CO₂Me | Q-5 | C(O)Me |
| 4-Cl | 5-Cl | CH₂ | CO₂Me | Q-5 | C(O)Me |
| 4-Br | 5-Cl | CH₂ | CO₂Me | Q-5 | C(O)Me |
| 4-CF₃ | 5-Cl | CH₂ | CO₂Me | Q-5 | CO₂Me |
| 4-Cl | 5-Cl | CH₂ | CO₂Me | Q-5 | CO₂Me |
| 4-Br | 5-Cl | CH₂ | CO₂Me | Q-5 | CO₂Me |
| 4-CF₃ | 5-Cl | CH₂ | Me | Q-5 | C(O)Me |
| 4-Cl | 5-Cl | CH₂ | Me | Q-5 | C(O)Me |
| 4-Br | 5-Cl | CH₂ | Me | Q-5 | C(O)Me |
| 4-CF₃ | H | CH₂ | H | Q-5 | CO₂Me |
| 4-Cl | H | CH₂ | H | Q-7 | CO₂Me |
| 4-Br | H | CH₂ | H | Q-7 | CO₂Me |
| 4-CF₃ | 5-Cl | CH₂ | H | Q-7 | C(O)Me |
| 4-Cl | 5-Cl | CH₂ | H | Q-7 | C(O)Me |
| 4-Br | 5-Cl | CH₂ | H | Q-7 | C(O)Me |
| 4-CF₃ | 5-Cl | CH₂ | CO₂Me | Q-7 | CO₂Me |
| 4-Cl | 5-Cl | CH₂ | CO₂Me | Q-7 | CO₂Me |
| 4-Br | 5-Cl | CH₂ | CO₂Me | Q-7 | CO₂Me |
| 4-CF₃ | 5-Cl | CH₂ | CO₂Me | Q-7 | C(O)Me |
| 4-Cl | 5-Cl | CH₂ | CO₂Me | Q-7 | C(O)Me |
| 4-Br | 5-Cl | CH₂ | CO₂Me | Q-7 | C(O)Me |
| 4-CF₃ | H | O | H | Q-1 | Me |
| 4-Cl | H | O | H | Q-1 | C(O)Me |
| 4-Br | H | O | H | Q-1 | CO₂Me |
| 4-CF₃ | H | O | Me | Q-1 | Me |
| 4-Cl | H | O | Me | Q-1 | C(O)Me |
| 4-Br | H | O | Me | Q-1 | CO₂Me |
| 4-CF₃ | 5-Cl | O | H | Q-1 | Me |
| 4-Cl | 5-Cl | O | H | Q-1 | C(O)Me |
| 4-Br | 5-Cl | O | H | Q-1 | CO₂Me |
| 4-CF₃ | H | O | H | Q-2 | Me |
| 4-Cl | H | O | H | Q-2 | C(O)Me |
| 4-Br | H | O | H | Q-2 | CO₂Me |
| 4-CF₃ | H | O | H | Q-2 | Me |
| 4-Cl | H | O | H | Q-2 | C(O)Me |
| 4-Br | H | O | H | Q-2 | CO₂Me |
| 4-CF₃ | H | O | H | Q-3 | Me |
| 4-Cl | H | O | H | Q-3 | C(O)Me |
| 4-Br | H | O | H | Q-3 | CO₂Me |
| 4-CF₃ | H | O | H | Q-3 | Me |
| 4-Cl | H | O | H | Q-3 | C(O)Me |
| 4-Br | H | O | H | Q-3 | CO₂Me |
| 4-CF₃ | H | O | H | Q-5 | Me |
| 4-Cl | H | O | H | Q-5 | C(O)Me |
| 4-Br | H | O | H | Q-5 | CO₂Me |
| 4-CF₃ | H | O | H | Q-5 | Me |
| 4-Cl | H | O | H | Q-5 | C(O)Me |
| 4-Br | H | O | H | Q-5 | CO₂Me |
| 4-CF₃ | H | S | H | Q-1 | Me |
| 4-Cl | H | S | H | Q-1 | C(O)Me |
| 4-Br | H | S | H | Q-1 | CO₂Me |
| 4-CF₃ | H | S | CO₂Me | Q-1 | Me |

TABLE 11-continued

| R₁ | R₂ | A | B | Q | Y |
|---|---|---|---|---|---|
| 4-Cl | H | S | CO₂Me | Q-1 | C(O)Me |
| 4-Br | H | S | CO₂Me | Q-1 | CO₂Me |
| 4-CF₃ | H | S | H | Q-2 | Me |
| 4-Cl | H | S | H | Q-2 | C(O)Me |
| 4-Br | H | S | H | Q-2 | CO₂Me |
| 4-CF₃ | H | S | CO₂Me | Q-2 | Me |
| 4-Cl | H | S | CO₂Me | Q-2 | C(O)Me |
| 4-Br | H | S | CO₂Me | Q-2 | CO₂Me |
| 4-CF₃ | H | S | H | Q-3 | Me |
| 4-Cl | H | S | H | Q-3 | C(O)Me |
| 4-Br | H | S | H | Q-3 | CO₂Me |
| 4-CF₃ | H | S | CO₂Me | Q-3 | Me |
| 4-Cl | H | S | CO₂Me | Q-3 | C(O)Me |
| 4-Br | H | S | CO₂Me | Q-3 | CO₂Me |
| 4-CF₃ | H | S | H | Q-5 | Me |
| 4-Cl | H | S | H | Q-5 | C(O)Me |
| 4-Br | H | S | H | Q-5 | CO₂Me |
| 4-CF₃ | H | S | CO₂Me | Q-5 | Me |
| 4-Cl | H | S | CO₂Me | Q-5 | C(O)Me |
| 4-Br | H | S | CO₂Me | Q-5 | CO₂Me |
| 4-CF₃ | H | S | H | Q-7 | Me |
| 4-Cl | H | S | H | Q-7 | C(O)Me |
| 4-Br | H | S | H | Q-7 | CO₂Me |
| 4-CF₃ | H | CH₂ | H | Q-1 | N(Me)CO₂Et |
| 4-Cl | H | CH₂ | H | Q-1 | N(Me)CO₂Et |
| 4-Br | H | CH₂ | H | Q-1 | N(Me)CO₂Et |
| 4-CF₃ | H | CH₂ | H | Q-1 | N(Me)CO₂nBu |
| 4-Cl | H | CH₂ | H | Q-1 | N(Me)CO₂nBu |
| 4-Br | H | CH₂ | H | Q-1 | N(Me)CO₂nBu |

TABLE 12

| R₁ | R₂ | A | B | Q | J |
|---|---|---|---|---|---|
| 4-CF₃ | 5-Cl | CH₂ | H | Q-1 | N(iPr)CO₂Et |
| 4-Cl | 5-Cl | CH₂ | H | Q-1 | N(iPr)CO₂Et |
| 4-Br | 5-Cl | CH₂ | H | Q-1 | N(iPr)CO₂Et |
| 4-CF₃ | 5-Cl | CH₂ | H | Q-1 | N(Et)CO₂Et |
| 4-Cl | 5-Cl | CH₂ | H | Q-1 | N(Et)CO₂Et |
| 4-Br | 5-Cl | CH₂ | H | Q-1 | N(Et)CO₂Et |
| 4-CF₃ | H | CH₂ | CO₂Me | Q-1 | N(Et)CO₂Et |
| 4-Cl | H | CH₂ | CO₂Me | Q-1 | N(Et)CO₂Et |
| 4-Br | H | CH₂ | CO₂Me | Q-1 | N(Et)CO₂Et |
| 4-CF₃ | H | CH₂ | CO₂Me | Q-1 | N(iPr)CO₂Et |
| 4-Cl | H | CH₂ | CO₂Me | Q-1 | N(iPr)CO₂Et |
| 4-Br | H | CH₂ | CO₂Me | Q-1 | N(iPr)CO₂Et |
| 4-CF₃ | 5-Cl | CH₂ | CO₂Me | Q-1 | N(iPr)CO₂Et |
| 4-Cl | 5-Cl | CH₂ | CO₂Me | Q-1 | N(iPr)CO₂Et |
| 4-Br | 5-Cl | CH₂ | CO₂Me | Q-1 | N(iPr)CO₂Et |
| 4-CF₃ | 5-Cl | CH₂ | CO₂Me | Q-1 | N(Me)CO₂nHex |
| 4-Cl | 5-Cl | CH₂ | CO₂Me | Q-1 | N(Me)CO₂nHex |
| 4-Br | 5-Cl | CH₂ | CO₂Me | Q-1 | N(Me)CO₂nHex |
| 4-CF₃ | 5-Cl | CH₂ | Ph | Q-1 | N(Me)CO₂Et |
| 4-Cl | 5-Cl | CH₂ | Ph | Q-1 | N(Me)CO₂Et |
| 4-Br | 5-Cl | CH₂ | Ph | Q-1 | N(Me)CO₂Et |
| 4-CF₃ | H | CH₂ | H | Q-3 | N(Me)CO₂Et |
| 4-Cl | H | CH₂ | H | Q-3 | N(Me)CO₂Et |
| 4-Br | H | CH₂ | H | Q-3 | N(Me)CO₂Et |
| 4-CF₃ | H | CH₂ | H | Q-3 | N(Me)CO₂nBu |
| 4-Cl | H | CH₂ | H | Q-3 | N(Me)CO₂nBu |
| 4-Br | H | CH₂ | H | Q-3 | N(Me)CO₂nBu |
| 4-CF₃ | 5-Cl | CH₂ | H | Q-3 | N(iPr)CO₂Et |
| 4-Cl | 5-Cl | CH₂ | H | Q-3 | N(iPr)CO₂Et |
| 4-Br | 5-Cl | CH₂ | H | Q-3 | N(iPr)CO₂Et |
| 4-CF₃ | 5-Cl | CH₂ | H | Q-3 | N(Et)CO₂Et |
| 4-Cl | 5-Cl | CH₂ | H | Q-3 | N(Et)CO₂Et |
| 4-Br | 5-Cl | CH₂ | H | Q-3 | N(Et)CO₂Et |
| 4-CF₃ | H | CH₂ | CO₂Me | Q-3 | N(Et)CO₂Et |
| 4-Cl | H | CH₂ | CO₂Me | Q-3 | N(Et)CO₂Et |
| 4-Br | H | CH₂ | CO₂Me | Q-3 | N(Et)CO₂Et |
| 4-CF₃ | H | CH₂ | CO₂Me | Q-3 | N(iPr)CO₂Et |
| 4-Cl | H | CH₂ | CO₂Me | Q-3 | N(iPr)CO₂Et |
| 4-Br | H | CH₂ | CO₂Me | Q-3 | N(iPr)CO₂Et |
| 4-CF₃ | 5-Cl | CH₂ | CO₂Me | Q-3 | N(iPr)CO₂Et |
| 4-Cl | 5-Cl | CH₂ | CO₂Me | Q-3 | N(iPr)CO₂Et |
| 4-Br | 5-Cl | CH₂ | CO₂Me | Q-3 | N(iPr)CO₂Et |
| 4-CF₃ | 5-Cl | CH₂ | CO₂Me | Q-3 | N(Me)CO₂nHex |
| 4-Cl | 5-Cl | CH₂ | CO₂Me | Q-3 | N(Me)CO₂nHex |
| 4-Br | 5-Cl | CH₂ | CO₂Me | Q-3 | N(Me)CO₂nHex |
| 4-CF₃ | 5-Cl | CH₂ | Ph | Q-3 | N(Me)CO₂Et |

TABLE 12-continued

| R₁ | R₂ | A | B | Q | J |
|---|---|---|---|---|---|
| 4-Cl | 5-Cl | CH₂ | Ph | Q-3 | N(Me)CO₂Et |
| 4-Br | 5-Cl | CH₂ | Ph | Q-3 | N(Me)CO₂Et |
| 4-CF₃ | H | CH₂ | H | Q-4 | N(Me)CO₂Et |
| 4-Cl | H | CH₂ | H | Q-4 | N(Me)CO₂Et |
| 4-Br | H | CH₂ | H | Q-4 | N(Me)CO₂Et |
| 4-CF₃ | H | CH₂ | H | Q-4 | N(Me)CO₂nBu |
| 4-Cl | H | CH₂ | H | Q-4 | N(Me)CO₂nBu |
| 4-Br | H | CH₂ | H | Q-4 | N(Me)CO₂nBu |
| 4-CF₃ | 5-Cl | CH₂ | H | Q-4 | N(iPr)CO₂Et |
| 4-Cl | 5-Cl | CH₂ | H | Q-4 | N(iPr)CO₂Et |
| 4-Br | 5-Cl | CH₂ | H | Q-4 | N(iPr)CO₂Et |
| 4-CF₃ | 5-Cl | CH₂ | H | Q-4 | N(Et)CO₂Et |
| 4-Cl | 5-Cl | CH₂ | H | Q-4 | N(Et)CO₂Et |
| 4-Br | 5-Cl | CH₂ | H | Q-4 | N(Et)CO₂Et |
| 4-CF₃ | H | CH₂ | CO₂Me | Q-4 | N(Et)CO₂Et |
| 4-Cl | H | CH₂ | CO₂Me | Q-4 | N(Et)CO₂Et |
| 4-Br | H | CH₂ | CO₂Me | Q-4 | N(Et)CO₂Et |
| 4-CF₃ | H | CH₂ | CO₂Me | Q-4 | N(iPr)CO₂Et |
| 4-Cl | H | CH₂ | CO₂Me | Q-4 | N(iPr)CO₂Et |
| 4-Br | H | CH₂ | CO₂Me | Q-4 | N(iPr)CO₂Et |
| 4-CF₃ | 5-Cl | CH₂ | CO₂Me | Q-4 | N(iPr)CO₂Et |
| 4-Cl | 5-Cl | CH₂ | CO₂Me | Q-4 | N(iPr)CO₂Et |
| 4-Br | 5-Cl | CH₂ | CO₂Me | Q-4 | N(iPr)CO₂Et |
| 4-CF₃ | 5-Cl | CH₂ | CO₂Me | Q-4 | N(Me)CO₂nHex |
| 4-Cl | 5-Cl | CH₂ | CO₂Me | Q-4 | N(Me)CO₂nHex |
| 4-Br | 5-Cl | CH₂ | CO₂Me | Q-4 | N(Me)CO₂nHex |
| 4-CF₃ | 5-Cl | CH₂ | Ph | Q-4 | N(Me)CO₂Et |
| 4-Cl | 5-Cl | CH₂ | Ph | Q-4 | N(Me)CO₂Et |
| 4-Br | 5-Cl | CH₂ | Ph | Q-4 | N(Me)CO₂Et |
| 4-CF₃ | H | CH₂ | H | Q-5 | N(Me)CO₂Et |
| 4-Cl | H | CH₂ | H | Q-5 | N(Me)CO₂Et |
| 4-Br | H | CH₂ | H | Q-5 | N(Me)CO₂Et |
| 4-CF₃ | H | CH₂ | H | Q-5 | N(Me)CO₂nBu |
| 4-Cl | H | CH₂ | H | Q-5 | N(Me)CO₂nBu |
| 4-Br | H | CH₂ | H | Q-5 | N(Me)CO₂nBu |
| 4-CF₃ | 5-Cl | CH₂ | H | Q-5 | N(iPr)CO₂Et |
| 4-Cl | 5-Cl | CH₂ | H | Q-5 | N(iPr)CO₂Et |
| 4-Br | 5-Cl | CH₂ | H | Q-5 | N(iPr)CO₂Et |
| 4-CF₃ | 5-Cl | CH₂ | H | Q-5 | N(Et)CO₂Et |
| 4-Cl | 5-Cl | CH₂ | H | Q-5 | N(Et)CO₂Et |
| 4-Br | 5-Cl | CH₂ | H | Q-5 | N(Et)CO₂Et |
| 4-CF₃ | H | CH₂ | CO₂Me | Q-5 | N(Et)CO₂Et |
| 4-Cl | H | CH₂ | CO₂Me | Q-5 | N(Et)CO₂Et |
| 4-Br | H | CH₂ | CO₂Me | Q-5 | N(Et)CO₂Et |
| 4-CF₃ | H | CH₂ | CO₂Me | Q-5 | N(iPr)CO₂Et |
| 4-Cl | H | CH₂ | CO₂Me | Q-5 | N(iPr)CO₂Et |
| 4-Br | H | CH₂ | CO₂Me | Q-5 | N(iPr)CO₂Et |
| 4-CF₃ | 5-Cl | CH₂ | CO₂Me | Q-5 | N(iPr)CO₂Et |
| 4-Cl | 5-Cl | CH₂ | CO₂Me | Q-5 | N(iPr)CO₂Et |
| 4-Br | 5-Cl | CH₂ | CO₂Me | Q-5 | N(iPr)CO₂Et |
| 4-CF₃ | 5-Cl | CH₂ | CO₂Me | Q-5 | N(Me)CO₂nHex |
| 4-Cl | 5-Cl | CH₂ | CO₂Me | Q-5 | N(Me)CO₂nHex |
| 4-Br | 5-Cl | CH₂ | CO₂Me | Q-5 | N(Me)CO₂nHex |
| 4-CF₃ | 5-Cl | CH₂ | Ph | Q-5 | N(Me)CO₂Et |
| 4-Cl | 5-Cl | CH₂ | Ph | Q-5 | N(Me)CO₂Et |
| 4-Br | 5-Cl | CH₂ | Ph | Q-5 | N(Me)CO₂Et |
| 4-CF₃ | H | CH₂ | H | Q-1 | N(Me)SO₂Ph |
| 4-Cl | H | CH₂ | H | Q-1 | N(Me)SO₂Ph |
| 4-Br | H | CH₂ | H | Q-1 | N(Me)SO₂Ph |
| 4-CF₃ | H | CH₂ | CO₂Me | Q-1 | N(Me)SO₂Ph |
| 4-Cl | H | CH₂ | CO₂Me | Q-1 | N(Me)SO₂Ph |
| 4-Br | H | CH₂ | CO₂Me | Q-1 | N(Me)SO₂Ph |
| 4-CF₃ | H | CH₂ | Ph | Q-1 | N(Me)SO₂Ph |
| 4-Cl | H | CH₂ | Ph | Q-1 | N(Me)SO₂Ph |
| 4-Br | H | CH₂ | Ph | Q-1 | N(Me)SO₂Ph |
| 4-CF₃ | H | CH₂ | Me | Q-1 | N(Me)SO₂Ph |
| 4-Cl | H | CH₂ | Me | Q-1 | N(Me)SO₂Ph |
| 4-Br | H | CH₂ | Me | Q-1 | N(Me)SO₂Ph |
| 4-CF₃ | 5-Cl | CH₂ | H | Q-1 | N(Me)SO₂Me |
| 4-Cl | 5-Cl | CH₂ | H | Q-1 | N(Me)SO₂Me |
| 4-Br | 5-Cl | CH₂ | H | Q-1 | N(Me)SO₂Me |
| 4-CF₃ | 5-Cl | CH₂ | CO₂Me | Q-1 | N(Me)SO₂Me |
| 4-Cl | 5-Cl | CH₂ | CO₂Me | Q-1 | N(Me)SO₂Me |
| 4-Br | 5-Cl | CH₂ | CO₂Me | Q-1 | N(Me)SO₂Me |
| 4-CF₃ | 5-Cl | CH₂ | Ph | Q-1 | N(Me)SO₂Me |
| 4-Cl | 5-Cl | CH₂ | Ph | Q-1 | N(Me)SO₂Me |
| 4-Br | 5-Cl | CH₂ | Ph | Q-1 | N(Me)SO₂Me |
| 4-CF₃ | 5-Me | CH₂ | H | Q-1 | N(Me)SO₂Me |
| 4-Cl | 5-Me | CH₂ | H | Q-1 | N(Me)SO₂Me |
| 4-Br | 5-Me | CH₂ | H | Q-1 | N(Me)SO₂Me |
| 4-CF₃ | 5-Me | CH₂ | CO₂Me | Q-1 | N(Me)SO₂Ph-4-Me |

TABLE 12-continued

| R₁ | R₂ | A | B | Q | J |
|---|---|---|---|---|---|
| 4-Cl | 5-Me | CH₂ | CO₂Me | Q-1 | N(Me)SO₂Ph-4-Me |
| 4-Br | 5-Me | CH₂ | CO₂Me | Q-1 | N(Me)SO₂Ph-4-Me |
| 4-CF₃ | H | CH₂ | H | Q-2 | N(Me)SO₂Ph |
| 4-Cl | H | CH₂ | H | Q-2 | N(Me)SO₂Ph |
| 4-Br | H | CH₂ | H | Q-2 | N(Me)SO₂Ph |
| 4-CF₃ | H | CH₂ | CO₂Me | Q-2 | N(Me)SO₂Ph |
| 4-Cl | H | CH₂ | CO₂Me | Q-2 | N(Me)SO₂Ph |
| 4-Br | H | CH₂ | CO₂Me | Q-2 | N(Me)SO₂Ph |
| 4-CF₃ | H | CH₂ | Ph | Q-2 | N(Me)SO₂Ph |
| 4-Cl | H | CH₂ | Ph | Q-2 | N(Me)SO₂Ph |
| 4-Br | H | CH₂ | Ph | Q-2 | N(Me)SO₂Ph |
| 4-CF₃ | H | CH₂ | Me | Q-2 | N(Me)SO₂Ph |
| 4-Cl | H | CH₂ | Me | Q-2 | N(Me)SO₂Ph |
| 4-Br | H | CH₂ | Me | Q-2 | N(Me)SO₂Ph |
| 4-CF₃ | H | CH₂ | H | Q-3 | N(Me)SO₂Ph |
| 4-Cl | H | CH₂ | H | Q-3 | N(Me)SO₂Ph |
| 4-Br | H | CH₂ | H | Q-3 | N(Me)SO₂Ph |
| 4-CF₃ | H | CH₂ | CO₂Me | Q-3 | N(Me)SO₂Ph |
| 4-Cl | H | CH₂ | CO₂Me | Q-3 | N(Me)SO₂Ph |
| 4-Br | H | CH₂ | CO₂Me | Q-3 | N(Me)SO₂Ph |
| 4-CF₃ | H | CH₂ | Ph | Q-3 | N(Me)SO₂Ph |
| 4-Cl | H | CH₂ | Ph | Q-3 | N(Me)SO₂Ph |
| 4-Br | H | CH₂ | Ph | Q-3 | N(Me)SO₂Ph |
| 4-CF₃ | H | CH₂ | Me | Q-3 | N(Me)SO₂Ph |
| 4-Cl | H | CH₂ | Me | Q-3 | N(Me)SO₂Ph |
| 4-Br | H | CH₂ | Me | Q-3 | N(Me)SO₂Ph |
| 4-CF₃ | 5-Cl | CH₂ | H | Q-3 | N(Me)SO₂Me |
| 4-Cl | 5-Cl | CH₂ | H | Q-3 | N(Me)SO₂Me |
| 4-Br | 5-Cl | CH₂ | H | Q-3 | N(Me)SO₂Me |
| 4-CF₃ | 5-Cl | CH₂ | CO₂Me | Q-3 | N(Me)SO₂Me |
| 4-Cl | 5-Cl | CH₂ | CO₂Me | Q-3 | N(Me)SO₂Me |
| 4-Br | 5-Cl | CH₂ | CO₂Me | Q-3 | N(Me)SO₂Me |
| 4-CF₃ | 5-Cl | CH₂ | Ph | Q-3 | N(Me)SO₂Me |
| 4-Cl | 5-Cl | CH₂ | Ph | Q-3 | N(Me)SO₂Me |
| 4-Br | 5-Cl | CH₂ | Ph | Q-3 | N(Me)SO₂Me |
| 4-CF₃ | 5-Me | CH₂ | H | Q-3 | N(Me)SO₂Me |
| 4-Cl | 5-Me | CH₂ | H | Q-3 | N(Me)SO₂Me |
| 4-Br | 5-Me | CH₂ | H | Q-3 | N(Me)SO₂Me |
| 4-CF₃ | 5-Me | CH₂ | CO₂Me | Q-3 | N(Me)SO₂Ph-4-Me |
| 4-Cl | 5-Me | CH₂ | CO₂Me | Q-3 | N(Me)SO₂Ph-4-Me |
| 4-Br | 5-Me | CH₂ | CO₂Me | Q-3 | N(Me)SO₂Ph-4-Me |
| 4-CF₃ | H | CH₂ | H | Q-4 | N(Me)SO₂Ph |
| 4-Cl | H | CH₂ | H | Q-4 | N(Me)SO₂Ph |
| 4-Br | H | CH₂ | H | Q-4 | N(Me)SO₂Ph |
| 4-CF₃ | H | CH₂ | CO₂Me | Q-4 | N(Me)SO₂Ph |
| 4-Cl | H | CH₂ | CO₂Me | Q-4 | N(Me)SO₂Ph |
| 4-Br | H | CH₂ | CO₂Me | Q-4 | N(Me)SO₂Ph |
| 4-CF₃ | H | CH₂ | Ph | Q-4 | N(Me)SO₂Ph |
| 4-Cl | H | CH₂ | Ph | Q-4 | N(Me)SO₂Ph |
| 4-Br | H | CH₂ | Ph | Q-4 | N(Me)SO₂Ph |
| 4-CF₃ | H | CH₂ | Me | Q-4 | N(Me)SO₂Ph |
| 4-Cl | H | CH₂ | Me | Q-4 | N(Me)SO₂Ph |
| 4-Br | H | CH₂ | Me | Q-4 | N(Me)SO₂Ph |
| 4-CF₃ | 5-Cl | CH₂ | H | Q-4 | N(Me)SO₂Me |
| 4-Cl | 5-Cl | CH₂ | H | Q-4 | N(Me)SO₂Me |
| 4-Br | 5-Cl | CH₂ | H | Q-4 | N(Me)SO₂Me |
| 4-CF₃ | 5-Cl | CH₂ | CO₂Me | Q-4 | N(Me)SO₂Me |
| 4-Cl | 5-Cl | CH₂ | CO₂Me | Q-4 | N(Me)SO₂Me |
| 4-Br | 5-Cl | CH₂ | CO₂Me | Q-4 | N(Me)SO₂Me |
| 4-CF₃ | 5-Cl | CH₂ | Ph | Q-4 | N(Me)SO₂Me |
| 4-Cl | 5-Cl | CH₂ | Ph | Q-4 | N(Me)SO₂Me |
| 4-Br | 5-Cl | CH₂ | Ph | Q-4 | N(Me)SO₂Me |
| 4-CF₃ | 5-Me | CH₂ | H | Q-4 | N(Me)SO₂Me |
| 4-Cl | 5-Me | CH₂ | H | Q-4 | N(Me)SO₂Me |
| 4-Br | 5-Me | CH₂ | H | Q-4 | N(Me)SO₂Me |
| 4-CF₃ | 5-Me | CH₂ | CO₂Me | Q-4 | N(Me)SO₂Ph-4-Me |
| 4-Cl | 5-Me | CH₂ | CO₂Me | Q-4 | N(Me)SO₂Ph-4-Me |
| 4-Br | 5-Me | CH₂ | CO₂Me | Q-4 | N(Me)SO₂Ph-4-Me |
| 4-CF₃ | H | CH₂ | H | Q-5 | N(Me)SO₂Ph |
| 4-Cl | H | CH₂ | H | Q-5 | N(Me)SO₂Ph |
| 4-Br | H | CH₂ | H | Q-5 | N(Me)SO₂Ph |
| 4-CF₃ | H | CH₂ | CO₂Me | Q-5 | N(Me)SO₂Ph |
| 4-Cl | H | CH₂ | CO₂Me | Q-5 | N(Me)SO₂Ph |
| 4-Br | H | CH₂ | CO₂Me | Q-5 | N(Me)SO₂Ph |
| 4-CF₃ | H | CH₂ | Ph | Q-5 | N(Me)SO₂Ph |
| 4-Cl | H | CH₂ | Ph | Q-5 | N(Me)SO₂Ph |
| 4-Br | H | CH₂ | Ph | Q-5 | N(Me)SO₂Ph |
| 4-CF₃ | H | CH₂ | Me | Q-5 | N(Me)SO₂Ph |
| 4-Cl | H | CH₂ | Me | Q-5 | N(Me)SO₂Ph |
| 4-Br | H | CH₂ | Me | Q-5 | N(Me)SO₂Ph |
| 4-CF₃ | 5-Cl | CH₂ | H | Q-5 | N(Me)SO₂Me |
| 4-Cl | 5-Cl | CH₂ | H | Q-5 | N(Me)SO₂Me |
| 4-Br | 5-Cl | CH₂ | H | Q-5 | N(Me)SO₂Me |
| 4-CF₃ | 5-Cl | CH₂ | CO₂Me | Q-5 | N(Me)SO₂Me |
| 4-Cl | 5-Cl | CH₂ | CO₂Me | Q-5 | N(Me)SO₂Me |
| 4-Br | 5-Cl | CH₂ | CO₂Me | Q-5 | N(Me)SO₂Me |
| 4-CF₃ | 5-Cl | CH₂ | Ph | Q-5 | N(Me)SO₂Me |
| 4-Cl | 5-Cl | CH₂ | Ph | Q-5 | N(Me)SO₂Me |
| 4-Br | 5-Cl | CH₂ | Ph | Q-5 | N(Me)SO₂Me |
| 4-CF₃ | 5-Me | CH₂ | H | Q-5 | N(Me)SO₂Me |
| 4-Cl | 5-Me | CH₂ | H | Q-5 | N(Me)SO₂Me |
| 4-Br | 5-Me | CH₂ | H | Q-5 | N(Me)SO₂Me |
| 4-CF₃ | 5-Me | CH₂ | CO₂Me | Q-5 | N(Me)SO₂Ph-4-Me |
| 4-Cl | 5-Me | CH₂ | CO₂Me | Q-5 | N(Me)SO₂Ph-4-Me |
| 4-Br | 5-Me | CH₂ | CO₂Me | Q-5 | N(Me)SO₂Ph-4-Me |
| 4-CF₃ | H | CH₂ | H | Q-7 | N(Me)SO₂Ph |
| 4-Cl | H | CH₂ | H | Q-7 | N(Me)SO₂Ph |
| 4-Br | H | CH₂ | H | Q-7 | N(Me)SO₂Ph |
| 4-CF₃ | H | CH₂ | CO₂Me | Q-7 | N(Me)SO₂Ph |
| 4-Cl | H | CH₂ | CO₂Me | Q-7 | N(Me)SO₂Ph |
| 4-Br | H | CH₂ | CO₂Me | Q-7 | N(Me)SO₂Ph |
| 4-CF₃ | H | CH₂ | Ph | Q-7 | N(Me)SO₂Ph |
| 4-Cl | H | CH₂ | Ph | Q-7 | N(Me)SO₂Ph |
| 4-Br | H | CH₂ | Ph | Q-7 | N(Me)SO₂Ph |
| 4-CF₃ | H | CH₂ | Me | Q-7 | N(Me)SO₂Ph |
| 4-Cl | H | CH₂ | Me | Q-7 | N(Me)SO₂Ph |
| 4-Br | H | CH₂ | Me | Q-7 | N(Me)SO₂Ph |
| 4-CF₃ | 5-Cl | CH₂ | H | Q-7 | N(Me)SO₂Me |
| 4-Cl | 5-Cl | CH₂ | H | Q-7 | N(Me)SO₂Me |
| 4-Br | 5-Cl | CH₂ | H | Q-7 | N(Me)SO₂Me |
| 4-CF₃ | 5-Cl | CH₂ | CO₂Me | Q-7 | N(Me)SO₂Me |
| 4-Cl | 5-Cl | CH₂ | CO₂Me | Q-7 | N(Me)SO₂Me |
| 4-Br | 5-Cl | CH₂ | CO₂Me | Q-7 | N(Me)SO₂Me |
| 4-CF₃ | 5-Cl | CH₂ | Ph | Q-7 | N(Me)SO₂Me |
| 4-Cl | 5-Cl | CH₂ | Ph | Q-7 | N(Me)SO₂Me |
| 4-Br | 5-Cl | CH₂ | Ph | Q-7 | N(Me)SO₂Me |
| 4-CF₃ | 5-Me | CH₂ | H | Q-7 | N(Me)SO₂Me |
| 4-Cl | 5-Me | CH₂ | H | Q-7 | N(Me)SO₂Me |
| 4-Br | 5-Me | CH₂ | H | Q-7 | N(Me)SO₂Me |
| 4-CF₃ | 5-Me | CH₂ | CO₂Me | Q-7 | N(Me)SO₂Ph-4-Me |
| 4-Cl | 5-Me | CH₂ | CO₂Me | Q-7 | N(Me)SO₂Ph-4-Me |
| 4-Br | 5-Me | CH₂ | CO₂Me | Q-7 | N(Me)SO₂Ph-4-Me |
| 4-CF₃ | H | CH₂ | H | Q-1 | CO₂Me |
| 4-Cl | H | CH₂ | H | Q-1 | CO₂Me |
| 4-Br | H | CH₂ | H | Q-1 | CO₂Me |
| 4-CF₃ | H | CH₂ | CO₂Me | Q-1 | CO₂Me |
| 4-Cl | H | CH₂ | CO₂Me | Q-1 | CO₂Me |
| 4-Br | H | CH₂ | CO₂Me | Q-1 | CO₂Me |
| 4-CF₃ | H | CH₂ | Ph | Q-1 | CO₂Me |
| 4-Cl | H | CH₂ | Ph | Q-1 | CO₂Me |
| 4-Br | H | CH₂ | Ph | Q-1 | CO₂Me |
| 4-CF₃ | H | CH₂ | Me | Q-1 | CO₂Et |
| 4-Cl | H | CH₂ | Me | Q-1 | CO₂Et |
| 4-Br | H | CH₂ | Me | Q-1 | CO₂Et |
| 4-CF₃ | 5-Cl | CH₂ | H | Q-1 | CO₂nPr |
| 4-Cl | 5-Cl | CH₂ | H | Q-1 | CO₂nPr |
| 4-Br | 5-Cl | CH₂ | H | Q-1 | CO₂nPr |
| 4-CF₃ | 5-Cl | CH₂ | CO₂Me | Q-1 | CO₂nPr |
| 4-Cl | 5-Cl | CH₂ | CO₂Me | Q-1 | CO₂nPr |
| 4-Br | 5-Cl | CH₂ | CO₂Me | Q-1 | CO₂nPr |
| 4-CF₃ | 5-Cl | CH₂ | Ph | Q-1 | CO₂CH₂CH₂OEt |
| 4-Cl | 5-Cl | CH₂ | Ph | Q-1 | CO₂CH₂CH₂OEt |
| 4-Br | 5-Cl | CH₂ | Ph | Q-1 | CO₂CH₂CH₂OEt |
| 4-CF₃ | 5-Me | CH₂ | H | Q-1 | CO₂CH₂Ph |
| 4-Cl | 5-Me | CH₂ | H | Q-1 | CO₂CH₂Ph |
| 4-Br | 5-Me | CH₂ | H | Q-1 | CO₂CH₂Ph |
| 4-CF₃ | 5-Me | CH₂ | CO₂Me | Q-1 | CO₂CH₂Ph |
| 4-Cl | 5-Me | CH₂ | CO₂Me | Q-1 | CO₂CH₂Ph |
| 4-Br | 5-Me | CH₂ | CO₂Me | Q-1 | CO₂CH₂Ph |
| 4-CF₃ | H | CH₂ | H | Q-1 | CO₂nBu |
| 4-Cl | H | CH₂ | H | Q-1 | CO₂nBu |
| 4-Br | H | CH₂ | H | Q-1 | CO₂nBu |
| 4-CF₃ | H | CH₂ | CO₂Me | Q-1 | CO₂nBu |
| 4-Cl | H | CH₂ | CO₂Me | Q-1 | CO₂nBu |
| 4-Br | H | CH₂ | CO₂Me | Q-1 | CO₂nBu |
| 4-CF₃ | H | CH₂ | Ph | Q-1 | CO₂nBu |
| 4-Cl | H | CH₂ | Ph | Q-1 | CO₂nBu |
| 4-Br | H | CH₂ | Ph | Q-1 | CO₂nBu |
| 4-CF₃ | H | CH₂ | Me | Q-1 | CO₂nBu |
| 4-Cl | H | CH₂ | Me | Q-1 | CO₂nBu |
| 4-Br | H | CH₂ | Me | Q-1 | CO₂nBu |
| 4-CF₃ | 5-Cl | CH₂ | H | Q-1 | CO₂nBu |

TABLE 12-continued

| R₁ | R₂ | A | B | Q | J |
|---|---|---|---|---|---|
| 4-Cl | 5-Cl | CH₂ | H | Q-1 | CO₂nBu |
| 4-Br | 5-Cl | CH₂ | H | Q-1 | CO₂nBu |
| 4-CF₃ | 5-Cl | CH₂ | CO₂Me | Q-1 | CO₂nBu |
| 4-Cl | 5-Cl | CH₂ | CO₂Me | Q-1 | CO₂nBu |
| 4-Br | 5-Cl | CH₂ | CO₂Me | Q-1 | CO₂nBu |
| 4-CF₃ | 5-Cl | CH₂ | Ph | Q-1 | CO₂nBu |
| 4-Cl | 5-Cl | CH₂ | Ph | Q-1 | CO₂nBu |
| 4-Br | 5-Cl | CH₂ | Ph | Q-1 | CO₂nBu |
| 4-CF₃ | 5-Me | CH₂ | H | Q-1 | CO₂nBu |
| 4-Cl | 5-Me | CH₂ | H | Q-1 | CO₂nBu |
| 4-Br | 5-Me | CH₂ | H | Q-1 | CO₂nBu |
| 4-CF₃ | 5-Me | CH₂ | CO₂Me | Q-1 | CO₂nBu |
| 4-Cl | 5-Me | CH₂ | CO₂Me | Q-1 | CO₂nBu |
| 4-Br | 5-Me | CH₂ | CO₂Me | Q-1 | CO₂nBu |
| 4-CF₃ | H | CH₂ | H | Q-3 | CO₂Me |
| 4-Cl | H | CH₂ | H | Q-3 | CO₂Me |
| 4-Br | H | CH₂ | H | Q-3 | CO₂Me |
| 4-CF₃ | H | CH₂ | CO₂Me | Q-3 | CO₂Me |
| 4-Cl | H | CH₂ | CO₂Me | Q-3 | CO₂Me |
| 4-Br | H | CH₂ | CO₂Me | Q-3 | CO₂Me |
| 4-CF₃ | H | CH₂ | Ph | Q-3 | CO₂Me |
| 4-Cl | H | CH₂ | Ph | Q-3 | CO₂Me |
| 4-Br | H | CH₂ | Ph | Q-3 | CO₂Me |
| 4-CF₃ | H | CH₂ | Me | Q-3 | CO₂Et |
| 4-Cl | H | CH₂ | Me | Q-3 | CO₂Et |
| 4-Br | H | CH₂ | Me | Q-3 | CO₂Et |
| 4-CF₃ | 5-Cl | CH₂ | H | Q-3 | CO₂nPr |
| 4-Cl | 5-Cl | CH₂ | H | Q-3 | CO₂nPr |
| 4-Br | 5-Cl | CH₂ | H | Q-3 | CO₂nPr |
| 4-CF₃ | 5-Cl | CH₂ | CO₂Me | Q-3 | CO₂nPr |
| 4-Cl | 5-Cl | CH₂ | CO₂Me | Q-3 | CO₂nPr |
| 4-Br | 5-Cl | CH₂ | CO₂Me | Q-3 | CO₂nPr |
| 4-CF₃ | 5-Cl | CH₂ | Ph | Q-3 | CO₂CH₂CH₂OEt |
| 4-Cl | 5-Cl | CH₂ | Ph | Q-3 | CO₂CH₂CH₂OEt |
| 4-Br | 5-Cl | CH₂ | Ph | Q-3 | CO₂CH₂CH₂OEt |
| 4-CF₃ | 5-Me | CH₂ | H | Q-3 | CO₂CH₂Ph |
| 4-Cl | 5-Me | CH₂ | H | Q-3 | CO₂CH₂Ph |
| 4-Br | 5-Me | CH₂ | H | Q-3 | CO₂CH₂Ph |
| 4-CF₃ | 5-Me | CH₂ | CO₂Me | Q-3 | CO₂CH₂Ph |
| 4-Cl | 5-Me | CH₂ | CO₂Me | Q-3 | CO₂CH₂Ph |
| 4-Br | 5-Me | CH₂ | CO₂Me | Q-3 | CO₂CH₂Ph |
| 4-CF₃ | H | CH₂ | H | Q-3 | CO₂nBu |
| 4-Cl | H | CH₂ | H | Q-3 | CO₂nBu |
| 4-Br | H | CH₂ | H | Q-3 | CO₂nBu |
| 4-CF₃ | H | CH₂ | CO₂Me | Q-3 | CO₂nBu |
| 4-Cl | H | CH₂ | CO₂Me | Q-3 | CO₂nBu |
| 4-Br | H | CH₂ | CO₂Me | Q-3 | CO₂nBu |
| 4-CF₃ | H | CH₂ | Ph | Q-3 | CO₂nBu |
| 4-Cl | H | CH₂ | Ph | Q-3 | CO₂nBu |
| 4-Br | H | CH₂ | Ph | Q-3 | CO₂nBu |
| 4-CF₃ | H | CH₂ | Me | Q-3 | CO₂nBu |
| 4-Cl | H | CH₂ | Me | Q-3 | CO₂nBu |
| 4-Br | H | CH₂ | Me | Q-3 | CO₂nBu |
| 4-CF₃ | 5-Cl | CH₂ | H | Q-3 | CO₂nBu |
| 4-Cl | 5-Cl | CH₂ | H | Q-3 | CO₂nBu |
| 4-Br | 5-Cl | CH₂ | H | Q-3 | CO₂nBu |
| 4-CF₃ | 5-Cl | CH₂ | CO₂Me | Q-3 | CO₂nBu |
| 4-Cl | 5-Cl | CH₂ | CO₂Me | Q-3 | CO₂nBu |
| 4-Br | 5-Cl | CH₂ | CO₂Me | Q-3 | CO₂nBu |
| 4-CF₃ | 5-Cl | CH₂ | Ph | Q-3 | CO₂nBu |
| 4-Cl | 5-Cl | CH₂ | Ph | Q-3 | CO₂nBu |
| 4-Br | 5-Cl | CH₂ | Ph | Q-3 | CO₂nBu |
| 4-CF₃ | 5-Me | CH₂ | H | Q-3 | CO₂nBu |
| 4-Cl | 5-Me | CH₂ | H | Q-3 | CO₂nBu |
| 4-Br | 5-Me | CH₂ | H | Q-3 | CO₂nBu |
| 4-CF₃ | 5-Me | CH₂ | CO₂Me | Q-3 | CO₂nBu |
| 4-Cl | 5-Me | CH₂ | CO₂Me | Q-3 | CO₂nBu |
| 4-Br | 5-Me | CH₂ | CO₂Me | Q-3 | CO₂nBu |
| 4-CF₃ | H | CH₂ | H | Q-4 | CO₂Me |
| 4-Cl | H | CH₂ | H | Q-4 | CO₂Me |
| 4-Br | H | CH₂ | H | Q-4 | CO₂Me |
| 4-CF₃ | H | CH₂ | CO₂Me | Q-4 | CO₂Me |
| 4-Cl | H | CH₂ | CO₂Me | Q-4 | CO₂Me |
| 4-Br | H | CH₂ | CO₂Me | Q-4 | CO₂Me |
| 4-CF₃ | H | CH₂ | Ph | Q-4 | CO₂Me |
| 4-Cl | H | CH₂ | Ph | Q-4 | CO₂Me |
| 4-Br | H | CH₂ | Ph | Q-4 | CO₂Me |
| 4-CF₃ | H | CH₂ | Me | Q-4 | CO₂Et |
| 4-Cl | H | CH₂ | Me | Q-4 | CO₂Et |
| 4-Br | H | CH₂ | Me | Q-4 | CO₂Et |
| 4-CF₃ | 5-Cl | CH₂ | H | Q-4 | CO₂nPr |
| 4-Cl | 5-Cl | CH₂ | H | Q-4 | CO₂nPr |
| 4-Br | 5-Cl | CH₂ | H | Q-4 | CO₂nPr |
| 4-CF₃ | 5-Cl | CH₂ | CO₂Me | Q-4 | CO₂nPr |
| 4-Cl | 5-Cl | CH₂ | CO₂Me | Q-4 | CO₂nPr |
| 4-Br | 5-Cl | CH₂ | CO₂Me | Q-4 | CO₂nPr |
| 4-CF₃ | 5-Cl | CH₂ | Ph | Q-4 | CO₂CH₂CH₂OEt |
| 4-Cl | 5-Cl | CH₂ | Ph | Q-4 | CO₂CH₂CH₂OEt |
| 4-Br | 5-Cl | CH₂ | Ph | Q-4 | CO₂CH₂CH₂OEt |
| 4-CF₃ | 5-Me | CH₂ | H | Q-4 | CO₂CH₂Ph |
| 4-Cl | 5-Me | CH₂ | H | Q-4 | CO₂CH₂Ph |
| 4-Br | 5-Me | CH₂ | H | Q-4 | CO₂CH₂Ph |
| 4-CF₃ | 5-Me | CH₂ | CO₂Me | Q-4 | CO₂CH₂Ph |
| 4-Cl | 5-Me | CH₂ | CO₂Me | Q-4 | CO₂CH₂Ph |
| 4-Br | 5-Me | CH₂ | CO₂Me | Q-4 | CO₂CH₂Ph |
| 4-CF₃ | H | CH₂ | H | Q-4 | CO₂nBu |
| 4-Cl | H | CH₂ | H | Q-4 | CO₂nBu |
| 4-Br | H | CH₂ | H | Q-4 | CO₂nBu |
| 4-CF₃ | H | CH₂ | CO₂Me | Q-4 | CO₂nBu |
| 4-Cl | H | CH₂ | CO₂Me | Q-4 | CO₂nBu |
| 4-Br | H | CH₂ | CO₂Me | Q-4 | CO₂nBu |
| 4-CF₃ | H | CH₂ | Ph | Q-4 | CO₂nBu |
| 4-Cl | H | CH₂ | Ph | Q-4 | CO₂nBu |
| 4-Br | H | CH₂ | Ph | Q-4 | CO₂nBu |
| 4-CF₃ | H | CH₂ | Me | Q-4 | CO₂nBu |
| 4-Cl | H | CH₂ | Me | Q-4 | CO₂nBu |
| 4-Br | H | CH₂ | Me | Q-4 | CO₂nBu |
| 4-CF₃ | 5-Cl | CH₂ | H | Q-4 | CO₂nBu |
| 4-Cl | 5-Cl | CH₂ | H | Q-4 | CO₂nBu |
| 4-Br | 5-Cl | CH₂ | H | Q-4 | CO₂nBu |
| 4-CF₃ | 5-Cl | CH₂ | CO₂Me | Q-4 | CO₂nBu |
| 4-Cl | 5-Cl | CH₂ | CO₂Me | Q-4 | CO₂nBu |
| 4-Br | 5-Cl | CH₂ | CO₂Me | Q-4 | CO₂nBu |
| 4-CF₃ | 5-Cl | CH₂ | Ph | Q-4 | CO₂nBu |
| 4-Cl | 5-Cl | CH₂ | Ph | Q-4 | CO₂nBu |
| 4-Br | 5-Cl | CH₂ | Ph | Q-4 | CO₂nBu |
| 4-CF₃ | 5-Me | CH₂ | H | Q-4 | CO₂nBu |
| 4-Cl | 5-Me | CH₂ | H | Q-4 | CO₂nBu |
| 4-Br | 5-Me | CH₂ | H | Q-4 | CO₂nBu |
| 4-CF₃ | 5-Me | CH₂ | CO₂Me | Q-4 | CO₂nBu |
| 4-Cl | 5-Me | CH₂ | CO₂Me | Q-4 | CO₂nBu |
| 4-Br | 5-Me | CH₂ | CO₂Me | Q-4 | CO₂nBu |
| 4-CF₃ | H | CH₂ | H | Q-5 | CO₂Me |
| 4-Cl | H | CH₂ | H | Q-5 | CO₂Me |
| 4-Br | H | CH₂ | H | Q-5 | CO₂Me |
| 4-CF₃ | H | CH₂ | CO₂Me | Q-5 | CO₂Me |
| 4-Cl | H | CH₂ | CO₂Me | Q-5 | CO₂Me |
| 4-Br | H | CH₂ | CO₂Me | Q-5 | CO₂Me |
| 4-CF₃ | H | CH₂ | Ph | Q-5 | CO₂Me |
| 4-Cl | H | CH₂ | Ph | Q-5 | CO₂Me |
| 4-Br | H | CH₂ | Ph | Q-5 | CO₂Me |
| 4-CF₃ | H | CH₂ | Me | Q-5 | CO₂Me |
| 4-Cl | H | CH₂ | Me | Q-5 | CO₂Et |
| 4-Br | H | CH₂ | Me | Q-5 | CO₂Et |
| 4-CF₃ | 5-Cl | CH₂ | H | Q-5 | CO₂nPr |
| 4-Cl | 5-Cl | CH₂ | H | Q-5 | CO₂nPr |
| 4-Br | 5-Cl | CH₂ | H | Q-5 | CO₂nPr |
| 4-CF₃ | 5-Cl | CH₂ | CO₂Me | Q-5 | CO₂nPr |
| 4-Cl | 5-Cl | CH₂ | CO₂Me | Q-5 | CO₂nPr |
| 4-Br | 5-Cl | CH₂ | CO₂Me | Q-5 | CO₂nPr |
| 4-CF₃ | 5-Cl | CH₂ | Ph | Q-5 | CO₂CH₂CH₂OEt |
| 4-Cl | 5-Cl | CH₂ | Ph | Q-5 | CO₂CH₂CH₂OEt |
| 4-Br | 5-Cl | CH₂ | Ph | Q-5 | CO₂CH₂CH₂OEt |
| 4-CF₃ | 5-Me | CH₂ | H | Q-5 | CO₂CH₂Ph |
| 4-Cl | 5-Me | CH₂ | H | Q-5 | CO₂CH₂Ph |
| 4-Br | 5-Me | CH₂ | H | Q-5 | CO₂CH₂Ph |
| 4-CF₃ | 5-Me | CH₂ | CO₂Me | Q-5 | CO₂CH₂Ph |
| 4-Cl | 5-Me | CH₂ | CO₂Me | Q-5 | CO₂CH₂Ph |
| 4-Br | 5-Me | CH₂ | CO₂Me | Q-5 | CO₂CH₂Ph |
| 4-CF₃ | H | CH₂ | H | Q-5 | CO₂nBu |
| 4-Cl | H | CH₂ | H | Q-5 | CO₂nBu |
| 4-Br | H | CH₂ | H | Q-5 | CO₂nBu |
| 4-CF₃ | H | CH₂ | CO₂Me | Q-5 | CO₂nBu |
| 4-Cl | H | CH₂ | CO₂Me | Q-5 | CO₂nBu |
| 4-Br | H | CH₂ | CO₂Me | Q-5 | CO₂nBu |
| 4-CF₃ | H | CH₂ | Ph | Q-5 | CO₂nBu |
| 4-Cl | H | CH₂ | Ph | Q-5 | CO₂nBu |
| 4-Br | H | CH₂ | Ph | Q-5 | CO₂nBu |
| 4-CF₃ | H | CH₂ | Me | Q-5 | CO₂nBu |
| 4-Cl | H | CH₂ | Me | Q-5 | CO₂nBu |
| 4-Br | H | CH₂ | Me | Q-5 | CO₂nBu |
| 4-CF₃ | 5-Cl | CH₂ | H | Q-5 | CO₂nBu |

TABLE 12-continued

| R₁ | R₂ | A | B | Q | J |
|---|---|---|---|---|---|
| 4-Cl | 5-Cl | CH₂ | H | Q-5 | CO₂nBu |
| 4-Br | 5-Cl | CH₂ | H | Q-5 | CO₂nBu |
| 4-CF₃ | 5-Cl | CH₂ | CO₂Me | Q-5 | CO₂nBu |
| 4-Cl | 5-Cl | CH₂ | CO₂Me | Q-5 | CO₂nBu |
| 4-Br | 5-Cl | CH₂ | CO₂Me | Q-5 | CO₂nBu |
| 4-CF₃ | 5-Cl | CH₂ | Ph | Q-5 | CO₂nBu |
| 4-Cl | 5-Cl | CH₂ | Ph | Q-5 | CO₂nBu |
| 4-Br | 5-Cl | CH₂ | Ph | Q-5 | CO₂nBu |
| 4-CF₃ | 5-Me | CH₂ | H | Q-5 | CO₂nBu |
| 4-Cl | 5-Me | CH₂ | H | Q-5 | CO₂nBu |
| 4-Br | 5-Me | CH₂ | H | Q-5 | CO₂nBu |
| 4-CF₃ | 5-Me | CH₂ | CO₂Me | Q-5 | CO₂nBu |
| 4-Cl | 5-Me | CH₂ | CO₂Me | Q-5 | CO₂nBu |
| 4-Br | 5-Me | CH₂ | CO₂Me | Q-5 | CO₂nBu |

TABLE 13

| R₁ | R₂ | B | X |
|---|---|---|---|
| H | H | H | O |
| 4-Cl | H | H | O |
| 4-F | H | H | O |
| 4-Br | H | H | O |
| 4-CF₃ | H | H | O |
| 4-OCF₂H | H | H | O |
| 4-CF₃Cl | H | H | O |
| 4-CO₂Me | H | H | O |
| 4-CO₂-i-Pr | H | H | O |
| 4-NO₂ | H | H | O |
| 4-SMe | H | H | O |
| 4-SO₂Me | H | H | O |
| 4-CF₂Cl | H | H | O |
| 4-OCF₃ | H | H | O |
| 4-I | H | H | O |
| 4-OCF₂CF₂H | H | H | O |
| 4-CN | H | H | O |
| 4-Me | H | H | O |
| 3,4-CF₂CF₂O | H | H | O |
| 3,4-OCF₂CF₂ | H | H | O |
| 3,4-(Me)₂CCH₂O | H | O | O |
| 4-Cl | H | Me | O |
| 4-Br | H | Me | O |
| 4-CF₃ | H | Me | O |
| 4-SMe | H | Me | O |
| 4-OCF₂H | H | Me | O |
| 4-CF₃ | H | Et | O |
| 4-CO₂i-Pr | H | Me | O |
| 4-Cl | H | allyl | O |
| 4-Br | H | allyl | O |
| 4-CF₃ | H | allyl | O |
| 4-Cl | H | CH₂Ph | O |
| 4-Br | H | CH₂Ph | O |
| 4-CF₃ | H | CH₂Ph | O |
| 4-CF₃ | H | 4-F-CH₂Ph | O |
| 4-SMe | H | 4-F-CH₂Ph | O |
| 4-CF₃ | H | 4-F-CH₂Ph | O |
| 4-Cl | H | 4-Cl-CH₂Ph | O |
| 4-NO₂ | H | 4-Cl-CH₂Ph | O |
| 4-OCF₂H | H | Ph | O |
| 4-OCF₃ | H | Ph | O |
| 4-CF₃ | H | Ph | O |
| 4-Cl | H | 4-Cl-Ph | O |
| 4-Br | H | 4-Cl-Ph | O |
| 4-OMe | H | 4-Cl-Ph | O |
| 4-CF₃ | H | n-Bu | O |
| 4-Cl | H | n-Bu | O |
| 4-CF₃ | H | (CH₂)₃Cl | O |
| 4-Cl | H | (CH₂)₃Cl | O |
| 4-Br | H | CH₂CF₃ | O |
| 4-OCF₃ | H | CH₂CF₃ | O |
| 4-SCF₂H | H | CH₂OMe | O |
| 4-CF₃ | H | CH₂OEt | O |
| 4-Cl | H | CH₂CO₂Me | O |
| 4-Br | H | CH₂CO₂Me | O |
| 4-OCF₂H | H | CH₂CN | O |
| 4-OCF₂CF₂H | H | (CH₂)₂CN | O |
| 4-CF₃ | H | (CH₂)₂CN | O |
| 4-CF₃ | H | (CH₂)₃CN | O |
| 4-CF₃ | H | CO₂Me | O |
| 4-Cl | H | CO₂Me | O |

TABLE 13-continued

| R₁ | R₂ | B | X |
|---|---|---|---|
| 4-Br | H | CO₂Me | O |
| 4-F | H | CO₂Me | O |
| 4-CF₂Cl | H | CO₂Me | O |
| 4-OCF₃ | H | CO₂Me | O |
| 3,4-CF₂CF₂O | H | CO₂Me | O |
| 3,4-OCF₂CF₂O | H | CO₂Me | O |
| 3,4-(Me)₂CCH₂O | H | CO₂Me | O |
| 4-CF₃ | H | CO₂Et | O |
| 4-Br | H | CO₂Et | O |
| 4-Cl | H | CO₂Et | O |
| 4-CF₃ | H | CO₂H | O |
| 4-CF₃ | H | CO₂Na | O |
| 4-CF₃ | H | CO₂Ph | O |
| 4-F | H | CO₂PH | O |
| 4-CF₃ | H | CO₂CH₂CCl₃ | O |
| 4-CF₃ | H | CO₂CH₂CF₃ | O |
| 4-CF₃ | H | CO₂(CH₂)Cl | O |
| 4-CF₃ | H | CO₂(CH₂)₂Br | O |
| 4-CF₃ | H | CO₂CH₂CN | O |
| 4-CF₃ | H | CO₂allyl | O |
| 4-CF₃ | H | CO₂CH₂Ph | O |
| 4-CF₃ | H | CO₂CH₂SMe | O |
| 4-CF₃ | H | C(O)NH₂ | O |
| 4-Cl | H | C(O)NH₂ | O |
| 4-Br | H | C(O)NHMe | O |
| 4-OCF₃ | H | C(O)NHMe | O |
| 4-CF₃ | H | C(O)NMe₂ | O |
| 4-Cl | H | C(O)NMe₂ | O |
| 4-Br | H | C(O)NHEt | O |
| 4-CF₃ | H | C(O)NHMe | O |
| 4-CF₃ | H | C(O)NHallyl | O |
| 4-CF₃ | H | C(O)N(Me)allyl | O |
| 4-CF₃ | H | C(O)NHPh-4-Cl | O |
| 4-OCF₃ | H | C(S)NH₂ | O |
| 4-CF₃ | H | C(S)NHMe | O |
| 4-Cl | H | C(S)NMe₂ | O |
| 4-Br | H | C(S)Me | O |
| 4-OCF₃ | H | C(S)Et | O |
| 4-CF₃ | H | C(S)NMe₂ | O |
| 4-Cl | H | C(S)NHMe | O |
| 4-Br | 5-Cl | H | O |
| 4-CF₃ | 5-Cl | Me | O |
| 4-OCF₃ | 5-Cl | Et | O |
| 4-Cl | 5-Cl | H | O |
| 4-SMe | 5-Cl | H | O |
| 4-CO₂Et | 5-Cl | H | O |
| 4-Br | 5-Cl | CO₂Me | O |
| 3-SMe | 5-Cl | CO₂Me | O |
| 4-CO₂Et | 5-Cl | CO₂Me | O |
| 4-CF₂ | 5-Cl | Co₂Me | O |
| 4-CF₃ | 5-Cl | H | O |
| 4-CF₃ | H | CO₂Me | O |
| 4-OCF₂H | 5-Cl | CO₂Me | O |
| 4-Cl | 5-Cl | CO₂Me | O |
| 4-Br | 5-Cl | C(O)Me | O |
| 4-CF₃ | 5-Cl | C(O)Et | O |
| 4-OCF₃ | 5-Cl | C(O)NMe₂ | O |
| 4-CF₃ | 5-F | H | O |
| 4-Cl | 5-F | H | O |
| 4-Br | 5-F | H | O |
| 4-OCF₂H | 5-F | H | O |
| 4-Cl | 5-F | CO₂Me | O |
| 4-Br | 5-F | CO₂Me | O |
| 4-CF₃ | 5-F | CO₂Me | O |
| 4-OCF₂H | 5-F | CO₂Me | O |
| 4-Cl | 5-F | CO₂Me | O |
| 4-Br | 5-OCF₂H | CO₂Me | O |
| 4-Cl | 5-OCF₂H | CO₂Me | O |
| 4-Br | 5-OCF₂H | CO₂Me | O |
| 4-CF₃ | 5-OCF₂H | CO₂Me | O |
| 4-OCF₃ | 5-OCF₂H | CO₂Me | O |
| 4-OCF₂H | 5-OCF₂H | CO₂Me | O |
| 4-Cl | 5-Br | CO₂Me | O |
| 4-Br | 5-NO₂ | CO₂Me | O |
| 4-CF₃ | 5-CF₃ | CO₂Me | O |
| 4-OCF₃ | 5-OCH₃ | CO₂Me | O |
| 4-CF₃ | 5-OCH₂Ph | Me | O |
| 4-CF₃ | 5-C(O)Me | Et | O |
| 4-CF₃ | 5-OCF₂CF₂H | CO₂Me | O |
| 4-CF₃ | 5-I | Me | O |
| 4-CF₃ | 5-OCF₃ | Et | O |

TABLE 13-continued

| R₁ | R₂ | B | X |
|---|---|---|---|
| 4-CF₃ | 5-Et | C(O)Me | O |
| 4-CF₃ | 5-Me | C(O)CF₃ | O |
| 4-CF₃ | 5-CN | Me | O |
| 4-CF₃ | 5-OMe | CO₂Me | O |
| 4-CF₃ | 5-OMe | CO₂Et | O |
| 4-CF₃ | 5-OMe | H | O |
| 4-Cl | 5-OMe | H | O |
| 4-CF₃ | 5-CO₂Me | n-C₆H₁₃ | O |
| 4-CF₃ | 5-SCF₂H | C(O)H | O |
| 4-CF₃ | 5-SO₂Me | (CH₂)₄Cl | O |
| 4-CF₃ | 5,6-di-Cl | H | O |
| 4-CF₃ | 5,6-di-Cl | CO₂Me | O |
| 4-CF₃ | 4-F | H | O |
| 4-Cl | 4-F | CO₂Me | O |
| 4-Br | 4-F | CO₂Me | O |
| 4-CF₃ | 4-Cl | H | O |
| 4-OCF₂H | 4-Cl | H | O |
| 4-OCF₂H | 4-Cl | CO₂Me | O |
| 4-CF₃ | 4-Br | H | O |
| 4-CF₃ | 4-Br | CO₂Me | O |
| 4-CF₃ | 6-Cl | CO₂Me | O |
| 4-CF₃ | 6-F | CO₂Me | O |
| 4-CF₃ | 6-CF₃ | CO₂Me | O |
| 4-CF₃ | 4-Cl | CO₂Me | O |
| 4-CF₃ | 4-F | CO₂Me | O |
| 4-CF₃ | 6-Br | CO₂Me | O |
| 4-CF₃ | 6-NO₂ | CO₂Me | O |
| 4-CF₃ | 6-Me | CO₂Me | O |
| 4-CF₃ | 4-Cl | CO₂Me | O |
| 4-CF₃ | 4-F | CO₂Me | O |
| 4-CF₃ | 4-Br | CO₂Me | O |
| 4-Cl | H | H | S |
| 4-CF₃ | H | Me | S |
| 4-Cl | H | CO₂Me | S |
| 4-CF₃ | H | H | S |
| 4-Cl | H | Me | S |
| 4-CF₃ | H | CO₂Me | S |
| 4-Cl | 5-Cl | H | S |
| 4-Cl | 5-F | Me | S |
| 4-CF₃ | 5-F | CO₂Me | S |
| 4-CF₃ | H | Ph | O |
| 4-OCF₃ | H | Ph | O |
| 4-Cl | H | Ph | O |
| 4-Br | H | Ph | O |
| 4-CF₃ | H | 4-F-Ph | O |
| 4-OCF₃ | H | 4-F-Ph | O |
| 4-Cl | H | 4-F-Ph | O |
| 4-Br | H | 4-F-Ph | O |
| 4-CF₃ | 5-F | Ph | O |
| 4-OCF₃ | 5-F | Ph | O |
| 4-Cl | 5-F | Ph | O |
| 4-Br | 5-F | Ph | O |
| 4-CF₃ | 5-F | 4-Cl-Ph | O |
| 4-OCF₃ | 5-F | 4-Cl-Ph | O |
| 4-Cl | 5-F | 4-Cl-Ph | O |
| 4-Br | 5-F | 4-Cl-Ph | O |
| 4-CF₃ | 5-F | 4-F-Ph | O |
| 4-OCF₃ | 5-F | 4-F-Ph | O |
| 4-Cl | 5-F | 4-F-Ph | O |
| 4-Br | 5-F | 4-F-Ph | O |
| 4-CF₃ | 5-F | Ph | O |
| 4-OCF₃ | 5-Cl | Ph | O |
| 4-Cl | 5-Cl | Ph | O |
| 4-Br | 5-Cl | Ph | O |
| 4-CF₃ | 5-Cl | 4-F-Ph | O |
| 4-OCF₃ | 5-Cl | 4-F-Ph | O |
| 4-Cl | 5-Cl | 4-F-Ph | O |
| 4-Br | 5-Cl | 4-F-Ph | O |
| 4-CF₃ | 5-Cl | 4-Cl-Ph | O |
| 4-OCF₃ | 5-Cl | 4-Cl-Ph | O |
| 4-Cl | 5-Cl | 4-Cl-Ph | O |
| 4-Br | 5-Cl | 4-Cl-Ph | O |
| 4-CF₃ | 5-Br | 4-F-Ph | O |
| 4-OCF₃ | 5-Br | 4-F-Ph | O |
| 4-Cl | 5-Br | 4-F-Ph | O |
| 4-Br | 5-Br | 4-F-Ph | O |
| 4-CF₃ | 5-Br | 4-Cl-Ph | O |
| 4-OCF₃ | 5-Br | 4-Cl-Ph | O |
| 4-Cl | 5-Br | 4-Cl-Ph | O |
| 4-Br | 5-Br | 4-F-Ph | O |

TABLE 14

| R₁ | R₂ | B | X | A |
|---|---|---|---|---|
| 4-CF₂Cl | H | H | O | O |
| 4-CF₃ | H | H | O | O |
| 4-Br | H | H | O | O |
| 3-CF₃ | H | H | O | O |
| 4-Cl | H | H | O | O |
| 3-Cl | H | H | O | O |
| 4-CF₃ | 5-Br | H | O | O |
| 4-Cl | 5-Br | H | O | O |
| 4-Br | 5-Br | H | O | O |
| 4-Cl | 7-Br | H | O | O |
| 4-CF₃ | 7-Br | H | O | O |
| 4-Br | 7-Br | H | O | O |
| 4-Cl | 5-F | H | O | O |
| 4-CF₃ | H | Me | O | O |
| 4-OCF₂H | 5-F | Me | O | O |
| 4-Br | H | Me | O | O |
| 4-OCF₃ | H | CO₂Me | O | O |
| 4-CO₂Me | 5-Cl | CO₂Me | O | O |
| 4-Cl | H | CO₂CH₂CF₃ | O | O |
| 4-Cl | 5-Cl | C(O)Me | O | O |
| 4-CF₃ | 5-OCF₂H | Me | O | O |
| 4-CF₃ | 5-F | CONHPh | O | O |
| 4-Cl | 5-Cl | n-Pr | O | O |
| 4-CF₃ | 5-OCF₂H | CO₂Me | O | O |
| 4-Cl | H | 4-Cl-Ph | O | O |
| 4-CF₃ | 5-Cl | CO₂Me | S | O |
| 4-CF₂Cl | H | H | O | S |
| 4-Cl | 5-F | H | O | S |
| 4-CF₃ | H | H | O | S |
| 4-Cl | H | H | O | S |
| 4-Br | H | H | O | S |
| 3-CF₃ | H | H | O | S |
| 4-Cl | H | H | O | S |
| 3-CF₃ | 5-Cl | H | O | S |
| 4-Cl | 5-Cl | H | O | S |
| 3-Cl | 5-Cl | H | O | S |
| 4-Br | 5-Cl | H | O | S |
| 4-Cl | 5-Cl | H | O | S |
| 4-CF₃ | 6-Cl | H | O | S |
| 3-CF₃ | 6-Cl | H | O | S |
| 4-Cl | 6-Cl | H | O | S |
| 3-Cl | 6-Cl | H | O | S |
| 4-Br | 6-Cl | H | O | S |
| 4-Cl | 6-Cl | H | O | S |
| 4-CF₃ | 5-Br | H | O | S |
| 3-CF₃ | 5-Br | H | O | S |
| 4-Cl | 5-Br | H | O | S |
| 3-Cl | 5-Br | H | O | S |
| 4-Br | 5-Br | H | O | S |
| 4-Cl | 5-Br | H | O | S |
| 4-CF₃ | 4-Cl | H | O | S |
| 4-Cl | 4-Cl | H | O | S |
| 4-Br | 4-Cl | H | O | S |
| 4-CF₃ | H | Me | O | S |
| 4-OCF₂H | 5-F | Me | O | S |
| 4-Br | H | Me | O | S |
| 4-OCF₃ | H | CO₂Me | O | S |
| 4-CO₂Me | 5-Cl | CO₂Me | O | S |
| 4-Cl | H | CO₂CH₂CF₃ | O | S |
| 4-CF₃ | 5-OCF₂H | Me | O | S |
| 4-CF₃ | 5-F | CONHPh | O | S |
| 4-Cl | 5-Cl | n-Pr | O | S |
| 4-CF₃ | 5-OCF₂H | CO₂Me | O | S |
| 4-Cl | H | 4-Cl-Ph | O | S |
| 4-CF₃ | 5-Cl | CO₂Me | S | S |
| 4-CF₂Cl | H | H | O | NMe |
| 4-Cl | 5-F | H | O | NMe |
| 4-CF₃ | H | Me | O | NMe |
| 4-OCF₂H | 5-F | Me | O | NMe |
| 4-Br | H | Me | O | NMe |
| 4-OCF₃ | H | CO₂Me | O | NMe |
| 4-CO₂Me | 5-Cl | CO₂Me | O | NMe |
| 4-Cl | H | CO₂CH₂CF₃ | O | NMe |
| 4-CF₃ | 5-OCF₂H | Me | O | NMe |

TABLE 14-continued

| $R_1$ | $R_2$ | B | X | A |
|---|---|---|---|---|
| 4-CF$_3$ | 5-F | CONHPh | O | NMe |
| 4-Cl | 5-Cl | n-Pr | O | NMe |
| 4-Cl | H | 4-Cl-Ph | O | NMe |
| 4-CF$_3$ | 5-Cl | CO$_2$Me | S | NMe |
| 4-CF$_3$ | H | H | O | SO$_2$ |
| 4-Cl | H | H | O | SO$_2$ |
| 4-Br | H | H | O | SO$_2$ |
| 3-CF$_3$ | H | H | O | SO$_2$ |
| 4-Cl | H | H | O | SO$_2$ |
| 3-Cl | H | H | O | SO$_2$ |
| 4-CF$_3$ | 5-Cl | H | O | SO$_2$ |
| 3-CF$_3$ | 5-Cl | H | O | SO$_2$ |
| 4-Cl | 5-Cl | H | O | SO$_2$ |
| 3-Cl | 5-Cl | H | O | SO$_2$ |
| 4-Cl | 5-Cl | H | O | SO$_2$ |
| 4-CF$_3$ | 6-Cl | H | O | SO$_2$ |
| 3-CF$_3$ | 6-Cl | H | O | SO$_2$ |
| 4-Cl | 6-Cl | H | O | SO$_2$ |
| 3-Cl | 6-Cl | H | O | SO$_2$ |
| 4-Br | 6-Cl | H | O | SO$_2$ |
| 4-Cl | 6-Cl | H | O | SO$_2$ |
| 4-Cl | 5-Cl | Me | O | SO$_2$ |
| 4-OCF$_3$ | H | Et | O | SO$_2$ |
| 4-Cl | H | CO$_2$Me | O | SO$_2$ |
| 4-OCF$_3$ | 5-Cl | CO$_2$Et | O | SO$_2$ |
| 3-CF$_3$ | H | H | O | SO($\alpha$)$^1$ |
| 4-CF$_3$ | H | H | O | SO($\alpha$) |
| 4-Br | H | H | O | SO($\beta$)$^1$ |
| 4-Cl | H | H | O | SO($\alpha$) |
| 4-Cl | H | H | O | SO($\beta$) |
| 4-Cl | H | H | O | SO($\alpha$) |
| 4-Cl | H | ·H | O | SO($\beta$) |
| 3-Cl | H | H | O | SO($\alpha$) |
| 3-Cl | H | H | O | SO($\beta$) |
| 4-CF$_3$ | 5-Cl | H | O | SO($\alpha$) |
| 4-CF$_3$ | 5-Cl | H | O | SO($\beta$) |
| 3-CF$_3$ | 5-Cl | H | O | SO($\alpha$) |
| 3-CF$_3$ | 5-Cl | H | O | SO($\beta$) |
| 4-Cl | 5-Cl | H | O | SO($\alpha$) |
| 4-Cl | 5-Cl | H | O | SO($\beta$) |
| 3-Cl | 5-Cl | H | O | SO($\alpha$) |
| 3-Cl | 5-Cl | H | O | SO($\beta$) |
| 4-Br | 5-Cl | H | O | SO($\alpha$) |
| 4-Br | 5-Cl | H | O | SO($\beta$) |
| 4-Cl | 5-Cl | H | O | SO($\alpha$) |
| 4-Cl | 5-Cl | H | O | SO($\beta$) |
| 4-CF$_3$ | 6-Cl | H | O | SO($\alpha$) |
| 4-CF$_3$ | 6-Cl | H | O | SO($\beta$) |
| 3-CF$_3$ | 6-Cl | H | O | SO($\alpha$) |
| 3-CF$_3$ | 6-Cl | H | O | SO($\beta$) |
| 4-Cl | 6-Cl | H | O | SO($\alpha$) |
| 4-Cl | 6-Cl | H | O | SO($\beta$) |
| 3-Cl | 6-Cl | H | O | SO($\alpha$) |
| 3-Cl | 6-Cl | H | O | SO($\beta$) |
| 4-Br | 6-Cl | H | O | SO($\alpha$) |
| 4-Br | 6-Cl | H | O | SO($\beta$) |
| 4-Cl | 6-Cl | H | O | SO($\alpha$) |
| 4-Cl | 6-Cl | H | O | SO($\beta$) |
| 3-CF$_3$ | H | H | O | SO($\beta$) |
| 4-CF$_3$ | H | H | O | SO($\beta$) |
| 4-CF$_3$ | 5-Cl | CO$_2$Me | O | N-allyl |
| 4-OCF$_3$ | 5-Cl | CO$_2$Me | O | N—CH$_2$Ph |
| 4-CF$_3$ | H | H | O | NH |
| 4-CF$_3$ | H | CO$_2$Me | O | NH |
| 4-CF$_3$ | 5-Cl | H | O | NMe |
| 4-CF$_3$ | 5-Cl | CO$_2$Me | O | NMe |
| 4-CF$_3$ | 5-Cl | CO$_2$Me | O | NC(O)CH$_3$ |
| 4-CF$_3$ | 5-Cl | CO$_2$Me | O | NCO$_2$CH$_3$ |
| 4-CF$_3$ | 5-Cl | CO$_2$Me | O | NSO$_2$CH$_3$ |
| 4-CF$_3$ | 5-Cl | CO$_2$Me | O | NCH$_2$Ph |
| 4-CF$_3$ | 5-Cl | CO$_2$Me | O | N-allyl |
| 4-CF$_3$ | 5-Cl | CO$_2$Me | O | NCO$_2$C(CH$_3$)$_3$ |
| 4-CF$_3$ | H | Ph | O | S |
| 4-OCF$_3$ | H | Ph | O | S |
| 4-Cl | H | Ph | O | S |
| 4-Br | H | Ph | O | S |
| 4-CF$_3$ | H | 4-F-Ph | O | S |
| 4-OCF$_3$ | H | 4-F-Ph | O | S |
| 4-Cl | H | 4-F-Ph | O | S |
| 4-Br | H | 4-F-Ph | O | S |
| 4-CF$_3$ | 5-F | Ph | O | S |
| 4-OCF$_3$ | 5-F | Ph | O | S |
| 4-Cl | 5-F | Ph | O | S |
| 4-Br | 5-F | Ph | O | S |
| 4-CF$_3$ | 5-F | 4-Cl-Ph | O | S |
| 4-Cl | 5-F | 4-Cl-Ph | O | S |
| 4-Br | 5-F | 4-Cl-Ph | O | S |
| 4-CF$_3$ | 5-F | 4-F-Ph | O | S |
| 4-OCF$_3$ | 5-F | 4-F-Ph | O | S |
| 4-Cl | 5-F | 4-F-Ph | O | S |
| 4-Br | 5-F | 4-F-Ph | O | S |
| 4-CF$_3$ | 5-Cl | Ph | O | S |
| 4-OCF$_3$ | 5-Cl | Ph | O | S |
| 4-Cl | 5-Cl | Ph | O | S |
| 4-Br | 5-Cl | Ph | O | S |
| 4-CF$_3$ | 5-Cl | 4-F-Ph | O | S |
| 4-OCF$_3$ | 5-Cl | 4-F-Ph | O | S |
| 4-Cl | 5-Cl | 4-F-Ph | O | S |
| 4-Br | 5-Cl | 4-F-Ph | O | S |
| 4-CF$_3$ | 5-Cl | 4-Cl-Ph | O | S |
| 4-OCF$_3$ | 5-Cl | 4-Cl-Ph | O | S |
| 4-Cl | 5-Cl | 4-Cl-Ph | O | S |
| 4-CF$_3$ | 5-Br | 4-F-PH | O | S |
| 4-OCF$_3$ | 5-Br | 4-F-Ph | O | S |
| 4-Cl | 5-Br | 4-F-Ph | O | S |
| 4-Br | 5-Br | 4-F-Ph | O | S |
| 4-OCF$_3$ | 5-Br | 4-Cl-Ph | O | S |
| 4-Cl | 5-Br | 4-Cl-Ph | O | S |
| 4-Br | 5-Br | 4-Cl-Ph | O | S |
| 4-CF$_3$ | 5-Br | 4-Cl-Ph | O | S |
| 4-CF$_3$ | H | Ph | O | O |
| 4-OCF$_3$ | H | Ph | O | O |
| 4-Cl | H | Ph | O | O |
| 4-Br | H | Ph | O | O |
| 4-CF$_3$ | H | 4-F-Ph | O | O |
| 4-OCF$_3$ | H | 4-F-Ph | O | O |
| 4-Cl | H | 4-F-Ph | O | O |
| 4-Br | H | 4-F-Ph | O | O |
| 4-CF$_3$ | 5-F | Ph | O | O |
| 4-OCF$_3$ | 5-F | Ph | O | O |
| 4-Cl | 5-F | Ph | O | O |
| 4-Br | 5-F | Ph | O | O |
| 4-CF$_3$ | 5-F | 4-Cl-Ph | O | O |
| 4-OCF$_3$ | 5-F | 4-Cl-Ph | O | O |
| 4-Cl | 5-F | 4-Cl-Ph | O | O |
| 4-Br | 5-F | 4-Cl-Ph | O | O |
| 4-CF$_3$ | 5-F | 4-F-Ph | O | O |
| 4-OCF$_3$ | 5-F | 4-F-Ph | O | O |
| 4-Cl | 5-F | 4-F-Ph | O | O |
| 4-Br | 5-F | 4-F-Ph | O | O |
| 4-CF$_3$ | 5-Cl | Ph | O | O |
| 4-OCF$_3$ | 5-Cl | Ph | O | O |
| 4-Cl | 5-Cl | Ph | O | O |
| 4-Br | 5-Cl | Ph | O | O |
| 4-CF$_3$ | 5-Cl | 4-F-Ph | O | O |
| 4-OCF$_3$ | 5-Cl | 4-F-Ph | O | O |
| 4-Cl | 5-Cl | 4-F-Ph | O | O |
| 4-Br | 5-Cl | 4-F-Ph | O | O |
| 4-CF$_3$ | 5-Cl | 4-Cl-Ph | O | O |
| 4-OCF$_3$ | 5-Cl | 4-Cl-Ph | O | O |
| 4-Cl | 5-Cl | 4-Cl-Ph | O | O |
| 4-Br | 5-Cl | 4-Cl-Ph | O | O |
| 4-CF$_3$ | 5-Br | 4-F-PH | O | O |
| 4-OCF$_3$ | 5-Br | 4-F-Ph | O | O |
| 4-Cl | 5-Br | 4-F-Ph | O | O |
| 4-Br | 5-Br | 4-F-Ph | O | O |
| 4-CF$_3$ | 5-Br | 4-F-Ph | O | O |
| 4-OCF$_3$ | 5-Br | 4-Cl-Ph | ·O | O |
| 4-Cl | 5-Br | 4-Cl-Ph | O | O |
| 4-Br | 5-Br | 4-Cl-Ph | O | O |
| 4-CF$_3$ | 5-Br | 4-Cl-Ph | O | O |
| 4-CF$_3$ | 5-F | 4-Cl-Ph | O | SO$_2$ |
| 4-Cl | 5-F | 4-Cl-Ph | O | SO$_2$ |
| 4-Br | 5-F | 4-Cl-Ph | O | SO$_2$ |
| 4-CF$_3$ | 5-Cl | 4-Cl-Ph | O | SO$_2$ |
| 4-OCF$_3$ | 5-Cl | 4-Cl-Ph | O | SO$_2$ |
| 4-Cl | 5-Cl | 4-Cl-Ph | O | SO$_2$ |
| 4-Br | 5-Cl | 4-Cl-Ph | O | SO$_2$ |
| 4-CF$_3$ | H | 4-Cl-Ph | O | SO$_2$ |
| 4-OCF$_3$ | H | 4-Cl-Ph | O | SO$_2$ |
| 4-Cl | H | 4-Cl-Ph | O | SO$_2$ |
| 4-Br | H | 4-Cl-Ph | O | SO$_2$ |

TABLE 14-continued

| R₁ | R₂ | B | X | A |
|---|---|---|---|---|
| 4-CF₃ | 5-F | 4-Cl-Ph | O | SO |
| 4-OCF₃ | 5-F | 4-Cl-Ph | O | SO |
| 4-Cl | 5-F | 4-Cl-Ph | O | SO |
| 4-Br | 5-F | 4-Cl-Ph | O | SO |
| 4-CF₃ | 5-Cl | 4-Cl-Ph | O | SO |
| 4-OCF₃ | 5-Cl | 4-Cl-Ph | O | SO |
| 4-Cl | 5-Cl | 4-Cl-Ph | O | SO |
| 4-Br | 5-Cl | 4-Cl-Ph | O | SO |
| 4-CF₃ | H | 4-Cl-Ph | O | SO |
| 4-OCF₃ | H | 4-Cl-Ph | O | SO |
| 4-Cl | H | 4-Cl-Ph | O | SO |
| 4-Br | H | 4-Cl-Ph | O | SO |
| 4-CF₃ | 5-F | 4-Cl-Ph | O | NMe |
| 4-OCF₃ | 5-F | 4-Cl-Ph | O | NMe |
| 4-Cl | 5-F | 4-Cl-Ph | O | NMe |
| 4-Br | 5-F | 4-Cl-Ph | O | NMe |
| 4-CF₃ | 5-Cl | 4-Cl-Ph | O | NMe |
| 4-OCF₃ | 5-Cl | 4-Cl-Ph | O | NMe |
| 4-Cl | 5-Cl | 4-Cl-Ph | O | NMe |
| 4-Br | 5-Cl | 4-Cl-Ph | O | NMe |
| 4-CF₃ | H | 4-Cl-Ph | O | NMe |
| 4-OCF₃ | H | 4-Cl-Ph | O | NMe |
| 4-Cl | H | 4-Cl-Ph | O | NMe |
| 4-Br | H | 4-Cl-Ph | O | NMe |
| 4-CF₃ | 5-Cl | 4-Cl-Ph | O | O |
| 4-OCF₃ | 5-Cl | 4-Cl-Ph | O | O |
| 4-Cl | 5-Cl | 4-Cl-Ph | O | O |
| 4-Br | 5-Cl | 4-Cl-Ph | O | O |
| 4-OCF₂CF₂H | H | Ph | O | O |
| 4-I | H | CH₃ | O | O |
| 4-COCH₃ | H | CH₃ | O | O |
| 4-OCF₂CF₂H | H | CH₃ | O | O |
| 4-CF₃ | H | CO₂CH₃ | O | O |
| 4-CF₃ | 5-F | H | O | O |
| 4-Br | 5-F | H | O | O |
| 4-OCF₃ | 5-F | H | O | O |
| 4-CF₃ | 5-Cl | H | O | O |
| 4-Br | 5-Cl | H | O | O |
| 4-OCF₃ | 5-Cl | H | O | O |
| 4-CF₃ | 5-F | Me | O | O |
| 4-Br | 5-F | Me | O | O |
| 4-OCF₃ | 5-F | Me | O | O |
| 4-CF₃ | H | CO₂Me | O | O |
| 4-OCF₃ | H | CO₂Me | O | O |
| 4-Cl | H | CO₂Me | O | O |
| 4-Br | H | CO₂Me | O | O |
| 4-CF₃ | 5-F | CO₂Me | O | O |
| 4-OCF₃ | 5-F | CO₂Me | O | O |
| 4-Cl | 5-F | CO₂Me | O | O |
| 4-Br | 5-F | CO₂Me | O | O |
| 4-CF₃ | 5-Cl | CO₂Me | O | O |
| 4-OCF₃ | 5-Cl | CO₂Me | O | O |
| 4-Cl | 5-Cl | CO₂Me | O | O |
| 4-Br | 5-Cl | CO₂Me | O | O |
| 4-CF₃ | 5-Br | CO₂Me | O | O |
| 4-OCF₃ | 5-Br | CO₂Me | O | O |
| 4-Cl | 5-Br | CO₂Me | O | O |
| 4-Br | 5-Br | CO₂Me | O | O |
| 4-CF₃ | 5-F | CO₂Me | O | S |
| 4-OCF₃ | 5-F | CO₂Me | O | S |
| 4-Cl | 5-F | CO₂Me | O | S |
| 4-Br | 5-F | CO₂Me | O | S |
| 4-CF₃ | 5-Cl | CO₂Me | O | S |
| 4-OCF₃ | 5-Cl | CO₂Me | O | S |
| 4-Cl | 5-Cl | CO₂Me | O | S |
| 4-Br | 5-Cl | CO₂Me | O | S |
| 4-CF₃ | 5-F | CO₂Me | O | N—CH₃ |
| 4-OCF₃ | 5-F | CO₂Me | O | N—CH₃ |
| 4-Cl | 5-F | CO₂Me | O | N—CH₃ |
| 4-Br | 5-F | CO₂Me | O | N—CH₃ |
| 4-CF₃ | 5-Cl | CO₂Me | O | N—CH₃ |
| 4-OCF₃ | 5-Cl | CO₂Me | O | N—CH₃ |
| 4-Cl | 5-Cl | CO₂Me | O | N—CH₃ |
| 4-Br | 5-Cl | CO₂Me | O | N—CH₃ |

[1]α denotes cis relationship to substituent B; β denotes trans relationship to substituent B.

TABLE 15

| R₁ | R₂ | B | Y | A |
|---|---|---|---|---|
| 4-OCF₃ | H | H | Me | CH₂ |
| 4-CF₃ | H | H | C(O)Me | CH₂ |
| 4-F | H | CO₂Me | Me | CH₂ |
| 4-OCF₂H | H | CO₂Me | C(O)Me | CH₂ |
| 4-CF₃ | H | Me | C(O)CF₃ | CH₂ |
| 4-Cl | H | Me | CO₂Et | CH₂ |
| 4-CF₃ | H | CO₂CH₂CF₃ | Me | CH₂ |
| 4-OCF₂H | H | CO₂Et | Me | CH₂ |
| 4-OCF₃ | H | CO₂CH₂CH₂Cl | Me | CH₂ |
| 4-Br | H | CONHMe | Me | CH₂ |
| 4-CF₃ | H | CO₂Me | C(O)Me | CH₂ |
| 4-CF₃ | H | CO₂Me | Me | CH₂ |
| 4-CF₃ | H | CO₂Me | CO₂Me | CH₂ |
| 4-CF₃ | 5-Cl | CO₂Me | C(O)Me | CH₂ |
| 4-CF₃ | 5-Cl | CO₂Me | Me | CH₂ |
| 4-CF₃ | 5-Cl | CO₂Me | CO₂Me | CH₂ |
| 4-CF₃ | 4-F | CO₂Me | C(O)Me | CH₂ |
| 4-CF₃ | 5-F | CO₂Me | C(O)Me | CH₂ |
| 4-CF₃ | 4-F | CO₂Me | CO₂Me | CH₂ |
| 4-CF₃ | 5-F | CO₂Me | CO₂Me | CH₂ |
| 4-CF₃ | H | H | CO₂-t-Bu | CH₂ |
| 4-CF₃ | 5-Cl | CO₂Me | SN(iPr)P(O)(OCH₃)(CH₃) | CH₂ |
| 4-CF₃ | 5-Cl | CO₂Me | SP(O)(OC₂H₅)₂ | CH₂ |
| 4-CF₃ | 5-Cl | CO₂Me | SN(iPr)₂ | CH₂ |
| 4-CF₃ | H | CO₂Me | SN(iPr)P(O)(OC₂H₅)(Ph) | CH₂ |
| 4-CF₃ | H | CO₂Me | SP(O)(OiPr)₂ | CH₂ |
| 4-CF₃ | H | CO₂Me | SN(sec Bu)₂ | CH₂ |
| 4-CF₃ | H | CO₂Me | $\overset{O}{\underset{\parallel}{SNP(OEt)_2}}$ | CH₂ |
| 4-Cl | H | CO₂Me | $\overset{O}{\underset{\parallel}{SNP(OEt)_2}}$ | CH₂ |

TABLE 15-continued

| R₁ | R₂ | B | Y | A |
|---|---|---|---|---|
| 4-OCF₂H | H | CO₂Me | SNP(OEt)₂ (S=O) | CH₂ |
| 4-CF₃ | 5-Cl | CO₂Me | SN(iPr)COC₂H₅ (S=O) | CH₂ |
| 4-CF₃ | 4-F | CO₂Me | SN(iPr)COC₂H₅ (S=O) | CH₂ |
| 4-CF₃ | 5-F | CO₂Me | SN(iPr)COC₂H₅ (S=O) | CH₂ |
| 4-CF₃ | 5-Cl | 4-Cl Phenyl | SN(iPr)COC₂H₅ (S=O) | CH₂ |
| 4-CF₃ | 4-F | CO₂Me | SN(iPr)COC₂H₅ (S=O) | CH₂ |
| 4-CF₃ | 5-F | CO₂Me | SN(iPr)COC₂H₅ (S=O) | CH₂ |
| 4-CF₃ | H | CO₂Me | SN(iPr)COC₂H₅ (S=O) | CH₂ |
| 4-CF₃ | H | CO₂Me | SN(CH₃)CO(CH₂)₃CH₃ (S=O) | CH₂ |
| 4-Cl | H | CO₂Me | SN(CH₃)CO(CH₂)₃CH₃ (S=O) | CH₂ |
| 4-CF₃ | 5-Cl | CO₂Me | SN(CH₃)CO(CH₂)₃CH₃ (S=O) | CH₂ |
| 4-CF₃ | 4-F | CO₂Me | SN(CH₃)CO(CH₂)₃CH₃ (S=O) | CH₂ |
| 4-CF₃ | 5-F | CO₂Me | SN(CH₃)CO(CH₂)₃CH₃ (S=O) | CH₂ |
| 4-CF₃ | 5-Cl | 4-Cl-Phenyl | SN(CH₃)CO(CH₂)₃CH₃ (S=O) | CH₂ |
| 4-CF₃ | 4-F | CO₂Me | SN(CH₃)CO(CH₂)₃CH₃ (S=O) | CH₂ |
| 4-CF₃ | 5-F | CO₂Me | SN(CH₃)CO(CH₂)₃CH₃ (S=O) | CH₂ |
| 4-CF₃ | H | CO₂Me | SN(CH₃)CO(CH₂)₃CH₃ (S=O) | CH₂ |
| 4-CF₃ | H | CO₂Me | SN(iPr)SO₂Ph | CH₂ |
| 4-Cl | H | CO₂Me | SN(iPr)SO₂Ph | CH₂ |
| 4-OCF₂H | H | CO₂Me | SN(iPr)SO₂Ph | CH₂ |
| 4-F | H | CO₂Me | SN(iPr)SO₂Ph | CH₂ |
| 4-CF₃ | 5-Cl | CO₂Me | SN(iPr)SO₂Ph | CH₂ |
| 4-CF₃ | 4-F | CO₂Me | SN(iPr)SO₂Ph | CH₂ |
| 4-CF₃ | 5-F | CO₂Me | SN(iPr)SO₂Ph | CH₂ |
| 4-CF₃ | 5-Cl | 4-Cl-Phenyl | SN(iPr)SO₂Ph | CH₂ |
| 4-CF₃ | 4-F | CO₂Me | SN(iPr)SO₂Ph | CH₂ |
| 4-CF₃ | 5-F | CO₂Me | SN(iPr)SO₂Ph | CH₂ |
| 4-CF₃ | H | CO₂Me | SN(iPr)SO₂Ph | CH₂ |
| 4-CF₃ | 5-Cl | CO₂Me | SN(CH₃)SO₂Ph | CH₂ |
| 4-CF₃ | 4-F | CO₂Me | SN(CH₃)SO₂Ph | CH₂ |
| 4-CF₃ | 5-F | CO₂Me | SN(CH₃)SO₂Ph | CH₂ |

TABLE 15-continued

| R₁ | R₂ | B | Y | A |
|---|---|---|---|---|
| 4-CF₃ | 5-Cl | 4-Cl-Phenyl | SN(CH₃)SO₂Ph | CH₂ |
| 4-CF₃ | 4-F | CO₂Me | SN(CH₃)SO₂Ph | CH₂ |
| 4-CF₃ | 5-F | CO₂Me | SN(CH₃)SO₂Ph | CH₂ |
| 4-CF₃ | H | CO₂Me | SN(CH₃)SO₂Ph | CH₂ |
| 4-CF₃ | H | CO₂Me | $\overset{\overset{O}{\parallel}}{S}COCH_2CH_2CH_2CH_3$ | CH₂ |
| 4-Cl | H | CO₂Me | $\overset{\overset{O}{\parallel}}{S}COCH_2CH_2CH_2CH_3$ | CH₂ |
| 4-OCF₂H | H | CO₂Me | $\overset{\overset{O}{\parallel}}{S}COCH_2CH_2CH_2CH_3$ | CH₂ |
| 4-OCF₂ | H | CO₂Me | $\overset{\overset{O}{\parallel}}{S}COCH_2CH_2CH_2CH_3$ | CH₂ |
| 4-F | H | CO₂Me | $\overset{\overset{O}{\parallel}}{S}COCH_2CH_2CH_2CH_3$ | CH₂ |
| 4-CF₃ | 5-Cl | CO₂Me | $\overset{\overset{O}{\parallel}}{S}COCH_2CH_2CH_2CH_3$ | CH₂ |
| 4-CF₃ | 4-F | CO₂Me | $\overset{\overset{O}{\parallel}}{S}COCH_2CH_2CH_2CH_3$ | CH₂ |
| 4-CF₃ | 5-F | CO₂Me | $\overset{\overset{O}{\parallel}}{S}COCH_2CH_2CH_2CH_3$ | CH₂ |
| 4-CF₃ | 5-Cl | 4-Cl-Phenyl | $\overset{\overset{O}{\parallel}}{S}COCH_2CH_2CH_2CH_3$ | CH₂ |
| 4-CF₃ | 4-F | CO₂Me | $\overset{\overset{O}{\parallel}}{S}COCH_2CH_2CH_2CH_3$ | CH₂ |
| 4-CF₃ | 5-F | CO₂Me | $\overset{\overset{O}{\parallel}}{S}COCH_2CH_2CH_2CH_3$ | CH₂ |
| 4-CF₃ | H | CO₂Me | $\overset{\overset{O}{\parallel}}{S}COCH_2CH_2CH_2CH_3$ | CH₂ |
| 4-CF₃ | 5-Cl | CO₂Me | Me | CH₂ |
| 4-OCF₃ | 5-Cl | CO₂Me | Me | CH₂ |
| 4-Br | 5-Cl | CO₂Me | Me | CH₂ |
| 4-CF₃ | 5-F | CO₂Me | COCH₃ | CH₂ |
| 4-OCF₃ | 5-F | CO₂Me | COCH₃ | CH₂ |
| 4-Br | 5-F | CO₂Me | COCH₃ | CH₂ |
| 4-CF₃ | 5-Cl | CO₂Me | CO₂CH₃ | CH₂ |
| 4-OCF₃ | 5-Cl | CO₂Me | CO₂CH₃ | CH₂ |
| 4-Br | 5-Cl | CO₂Me | CO₂CH₃ | CH₂ |
| 4-CF₃ | 5-F | CO₂Me | COCF₃ | CH₂ |
| 4-OCF₃ | 5-F | CO₂Me | COCF₃ | CH₂ |
| 4-Br | 5-F | CO₂Me | COCF₃ | CH₂ |
| 4-CF₃ | 4-Cl | 4-Cl—Ph | Me | CH₂ |
| 4-OCF₃ | 4-Cl | 4-Cl—Ph | Me | CH₂ |
| 4-Br | 4-Cl | 4-Cl—Ph | Me | CH₂ |
| 4-CF₃ | 4-Cl | 4-Cl—Ph | COCH₃ | CH₂ |
| 4-OCF₃ | 4-CL | 4-Cl—Ph | COCH₃ | CH₂ |
| 4-Br | 4-Cl | 4-Cl—Ph | COCH₃ | CH₂ |
| 4-CF₃ | 4-Cl | 4-Cl—Ph | CO₂CH₃ | CH₂ |
| 4-OCF₃ | 4-Cl | 4-Cl—Ph | CO₂CH₃ | CH₂ |
| 4-Br | 4-Cl | 4-Cl—Ph | CO₂CH₃ | CH₂ |
| 4-CF₃ | 4-Cl | 4-Cl—Ph | COCF₃ | CH₂ |
| 4-OCF₃ | 4-Cl | 4-Cl—Ph | COCF₃ | CH₂ |
| 4-Br | 4-Cl | 4-Cl—Ph | COCF₃ | CH₂ |
| 4-CF₃ | 4-Cl | 4-Cl—Ph | CO₂CH₂CH₃ | CH₂ |
| 4-OCF₃ | 4-Cl | 4-Cl—Ph | CO₂CH₂CH₃ | CH₂ |
| 4-Br | 4-Cl | 4-Cl—Ph | CO₂CH₂CH₃ | CH₂ |
| 4-CF₃ | 4-Cl | 4-F—Ph | Me | CH₂ |
| 4-OCF₃ | 4-Cl | 4-F—Ph | Me | CH₂ |

TABLE 15-continued

| R₁ | R₂ | B | Y | A |
|---|---|---|---|---|
| 4-Br | 4-Cl | 4-F—Ph | Me | CH₂ |
| 4-CF₃ | 4-Cl | 4-F—Ph | COCH₃ | CH₂ |
| 4-OCF₃ | 4-Cl | 4-F—Ph | COCH₃ | CH₂ |
| 4-Br | 4-Cl | 4-F—Ph | COCH₃ | CH₂ |
| 4-CF₃ | 4-Cl | 4-F—Ph | CO₂CH₃ | CH₂ |
| 4-OCF₃ | 4-Cl | 4-F—Ph | CO₂CH₃ | CH₂ |
| 4-Br | 4-Cl | 4-F—Ph | CO₂CH₃ | CH₂ |
| 4-CF₃ | 4-Cl | 4-F—Ph | COCH₂CH₃ | CH₂ |
| 4-OCF₃ | 4-Cl | 4-F—Ph | COCH₂CH₃ | CH₂ |
| 4-Br | 4-Cl | 4-F—Ph | COCH₂CH₃ | CH₂ |
| 4-CF₃ | H | Me | Me | NMe |
| 4-CF₃ | 5-Cl | CO₂Me | Me | S |
| 4-CF₃ | 5-Cl | Me | Me | NMe |
| 4-CF₃ | 5-Cl | Me | C(O)Me | S |
| 4-CF₃ | 5-F | CO₂Me | C(O)Me | NMe |
| 4-CF₃ | 5-F | Me | C(O)Me | SO |
| 4-CF₃ | H | CO₂Me | SCCl₃ | O |
| 4-CF₃ | H | CO₂Me | SCCl₃ | NMe |
| 4-CF₃ | H | Me | CO₂Me | O |
| 4-CF₃ | 5-OCF₂H | CO₂Me | n-Pr | NMe |
| 4-CF₃ | 5-CF₃ | Me | C(O)CF₃ | O |
| 4-CF₃ | 5-CF₃ | Me | C(O)CF₃ | NMe |
| 4-CF₃ | 5-Cl | CO₂Me | SMe | O |
| 4-CF₃ | H | H | Me | S |
| 4-CF₃ | H | H | CO₂Me | S |
| 4-CF₃ | H | H | C(O)Me | S |
| 4-CF₃ | 5-Cl | H | C(O)Me | S |
| 4-CF₃ | 5-Cl | H | CO₂Me | S |
| 4-CF₃ | 5-Cl | H | Me | S |
| 4-Cl | H | H | C(O)Me | S |
| 4-Cl | H | H | Me | S |
| 4-Cl | 5-Cl | H | C(O)Me | S |
| 4-Cl | 5-Cl | H | Me | S |
| 4-CF₃ | 5-Cl | CO₂Me | $\underset{\underset{SN(iPr)COC_2H_5}{\|}}{O}$ | O |
| 4-CF₃ | 4-F | CO₂Me | $\underset{\underset{SN(iPr)COC_2H_5}{\|}}{O}$ | O |
| 4-CF₃ | 5-F | CO₂Me | $\underset{\underset{SN(iPr)COC_2H_5}{\|}}{O}$ | O |
| 4-CF₃ | 5-Cl | 4-Cl-Phenyl | $\underset{\underset{SN(iPr)COC_2H_5}{\|}}{O}$ | O |
| 4-CF₃ | 4-F | 4-Cl-Phenyl | $\underset{\underset{SN(iPr)COC_2H_5}{\|}}{O}$ | O |
| 4-CF₃ | 5-F | 4-Cl-Phenyl | $\underset{\underset{SN(iPr)COC_2H_5}{\|}}{O}$ | O |
| 4-CF₃ | H | 4-Cl-Phenyl | $\underset{\underset{SN(iPr)COC_2H_5}{\|}}{O}$ | O |
| 4-CF₃ | H | CO₂Me | $\underset{\underset{SN(CH_3)CO(CH_2)_3CH_3}{\|}}{O}$ | O |
| 4-Cl | H | CO₂Me | $\underset{\underset{SN(CH_3)CO(CH_2)_3CH_3}{\|}}{O}$ | O |
| 4-CF₃ | 5-Cl | CO₂Me | $\underset{\underset{SN(CH_3)CO(CH_2)_3CH_3}{\|}}{O}$ | O |
| 4-CF₃ | 4-F | CO₂Me | $\underset{\underset{SN(CH_3)CO(CH_2)_3CH_3}{\|}}{O}$ | O |
| 4-CF₃ | 5-F | CO₂Me | $\underset{\underset{SN(CH_3)CO(CH_2)_3CH_3}{\|}}{O}$ | O |

TABLE 15-continued

| $R_1$ | $R_2$ | B | Y | A |
|---|---|---|---|---|
| 4-$CF_3$ | 5-Cl | 4-Cl-Phenyl | $SN(CH_3)\overset{\overset{O}{\|}}{C}O(CH_2)_3CH_3$ | O |
| 4-$CF_3$ | 4-F | 4-Cl-Phenyl | $SN(CH_3)\overset{\overset{O}{\|}}{C}O(CH_2)_3CH_3$ | O |
| 4-$CF_3$ | 5-F | 4-Cl-Phenyl | $SN(CH_3)\overset{\overset{O}{\|}}{C}O(CH_2)_3CH_3$ | O |
| 4-$CF_3$ | H | 4-Cl-Phenyl | $SN(CH_3)\overset{\overset{O}{\|}}{C}O(CH_2)_3CH_3$ | O |
| 4-$CF_3$ | H | $CO_2Me$ | $SN(iPr)SO_2CH_3$ | O |
| 4-Cl | H | $CO_2Me$ | $SN(iPr)SO_2CH_3$ | O |
| 4-$OCF_3$ | H | $CO_2Me$ | $SN(iPr)SO_2CH_3$ | O |
| 4-$CF_3$ | 5-Cl | $CO_2Me$ | $SN(iPr)SO_2CH_3$ | O |
| 4-$CF_3$ | 4-F | $CO_2Me$ | $SN(iPr)SO_2CH_3$ | O |
| 4-$CF_3$ | 5-F | $CO_2Me$ | $SN(iPr)SO_2CH_3$ | O |
| 4-$CF_3$ | 5-Cl | 4-Cl-Phenyl | $SN(iPr)SO_2CH_3$ | O |
| 4-$CF_3$ | 4-F | 4-Cl-Phenyl | $SN(iPr)SO_2CH_3$ | O |
| 4-$CF_3$ | 5-F | 4-Cl-Phenyl | $SN(iPr)SO_2CH_3$ | O |
| 4-$CF_3$ | H | 4-Cl-Phenyl | $SN(iPr)SO_2CH_3$ | O |
| 4-$CF_3$ | H | $CO_2Me$ | $SN(CH_3)SO_2Ph$ | O |
| 4-Cl | H | $CO_2Me$ | $SN(CH_3)SO_2Ph$ | O |
| 4-$OCF_2H$ | H | $CO_2Me$ | $SN(CH_3)SO_2Ph$ | O |
| 4-$OCF_3$ | H | $CO_2Me$ | $SN(CH_3)SO_2Ph$ | O |
| 4-F | H | $CO_2Me$ | $SN(CH_3)SO_2Ph$ | O |
| 4-$CF_3$ | 5-Cl | $CO_2Me$ | $SN(CH_3)SO_2Ph$ | O |
| 4-$CF_3$ | 4-F | $CO_2Me$ | $SN(CH_3)SO_2Ph$ | O |
| 4-$CF_3$ | 5-F | $CO_2Me$ | $SN(CH_3)SO_2Ph$ | O |
| 4-$CF_3$ | 5-Cl | 4-Cl-Phenyl | $SN(CH_3)SO_2Ph$ | O |
| 4-$CF_3$ | 4-F | 4-Cl-Phenyl | $SN(CH_3)SO_2Ph$ | O |
| 4-$CF_3$ | 5-F | 4-Cl-Phenyl | $SN(CH_3)SO_2Ph$ | O |
| 4-$CF_3$ | H | 4-Cl-Phenyl | $SN(CH_3)SO_2Ph$ | O |
| 4-$CF_3$ | H | $CO_2Me$ | $S\overset{\overset{O}{\|}}{C}OCH_2CH_2CH_2CH_3$ | O |
| 4-$CF_3$ | 5-Cl | $CO_2Me$ | $S\overset{\overset{O}{\|}}{C}OCH_2CH_2CH_2CH_3$ | O |
| 4-$CF_3$ | 4-F | $CO_2Me$ | $S\overset{\overset{O}{\|}}{C}OCH_2CH_2CH_2CH_3$ | O |
| 4-$CF_3$ | 5-F | $CO_2Me$ | $S\overset{\overset{O}{\|}}{C}OCH_2CH_2CH_2CH_3$ | O |
| 4-$CF_3$ | 5-Cl | 4-Cl-Phenyl | $S\overset{\overset{O}{\|}}{C}OCH_2CH_2CH_2CH_3$ | O |
| 4-$CF_3$ | 4-F | 4-Cl-Phenyl | $S\overset{\overset{O}{\|}}{C}OCH_2CH_2CH_2CH_3$ | O |
| 4-$CF_3$ | 5-F | 4-Cl-Phenyl | $S\overset{\overset{O}{\|}}{C}OCH_2CH_2CH_2CH_3$ | O |
| 4-$CF_3$ | H | 4-Cl-Phenyl | $S\overset{\overset{O}{\|}}{C}OCH_2CH_2CH_2CH_3$ | O |
| 4-$CF_3$ | 5-Cl | $CO_2Me$ | $SN(iPr)\overset{\overset{O}{\|}}{P}(OCH_3)CH_3$ | S |
| 4-$CF_3$ | 5-Cl | $CO_2Me$ | $-S\overset{\overset{O}{\|}}{P}(OC_2H_5)_2$ | S |
| 4-$CF_3$ | 5-Cl | $CO_2Me$ | $-S-N(iPr)_2$ | S |

TABLE 15-continued

| R$_1$ | R$_2$ | B | Y | A |
|---|---|---|---|---|
| 4-CF$_3$ | H | CO$_2$Me | SN(iPr)P(OC$_2$H$_5$)Ph, double bond O | S |
| 4-CF$_3$ | H | CO$_2$Me | —SP(OiPr)$_2$, double bond O | S |
| 4-CF$_3$ | H | CO$_2$Me | —S—N(s-Bu)$_2$ | S |
| 4-CF$_3$ | H | CO$_2$Me | SNP(OEt)$_2$, double bond O | S |
| 4-Cl | H | CO$_2$Me | SNP(OEt)$_2$, double bond O | S |
| 4-OCF$_2$H | H | CO$_2$Me | SNP(OEt)$_2$, double bond O | S |
| 4-CF$_3$ | H | CO$_2$Me | SN(iPr)COC$_2$H$_5$, double bond O | O |
| 4-Cl | H | CO$_2$Me | SN(iPr)COC$_2$H$_5$, double bond O | O |
| 4-OCF$_2$H | H | CO$_2$Me | SN(iPr)COC$_2$H$_5$, double bond O | O |
| 4-OCF$_3$ | H | CO$_2$Me | SN(iPr)COC$_2$H$_5$, double bond O | O |
| 4-F | H | CO$_2$Me | SN(iPr)COC$_2$H$_5$, double bond O | O |
| 4-CF$_3$ | 5-Cl | CO$_2$Me | SN(iPr)COC$_2$H$_5$, double bond O | O |
| 4-CF$_3$ | 4-F | CO$_2$Me | SN(iPr)COC$_2$H$_5$, double bond O | O |
| 4-CF$_3$ | 5-F | CO$_2$Me | SN(iPr)COC$_2$H$_5$, double bond O | O |
| 4-CF$_3$ | 5-Cl | 4-Cl-Phenyl | SN(iPr)COC$_2$H$_5$, double bond O | O |
| 4-CF$_3$ | 4-F | 4-Cl-Phenyl | SN(iPr)COC$_2$H$_5$, double bond O | O |
| 4-CF$_3$ | 5-F | 4-Cl-Phenyl | SN(iPr)COC$_2$H$_5$, double bond O | O |
| 4-CF$_3$ | H | 4-Cl-Phenyl | SN(iPr)COC$_2$H$_5$, double bond O | O |
| 4-CF$_3$ | H | CO$_2$Me | SN(CH$_3$)CO(CH$_2$)$_3$CH$_3$, double bond O | S |
| 4-Cl | H | CO$_2$Me | SN(CH$_3$)CO(CH$_2$)$_3$CH$_3$, double bond O | S |
| 4-OCF$_2$H | H | CO$_2$Me | SN(CH$_3$)CO(CH$_2$)$_3$CH$_3$, double bond O | S |

TABLE 15-continued

| R₁ | R₂ | B | Y | A |
|---|---|---|---|---|
| 4-OCF₃ | H | CO₂Me | SN(CH₃)$\overset{\overset{O}{\|}}{C}$O(CH₂)₃CH₃ | S |
| 4-F | H | CO₂Me | SN(CH₃)$\overset{\overset{O}{\|}}{C}$O(CH₂)₃CH₃ | S |
| 4-CF₃ | 5-Cl | CO₂Me | SN(CH₃)$\overset{\overset{O}{\|}}{C}$O(CH₂)₃CH₃ | S |
| 4-CF₃ | 4-F | CO₂Me | SN(CH₃)$\overset{\overset{O}{\|}}{C}$O(CH₂)₃CH₃ | S |
| 4-CF₃ | 5-F | CO₂Me | SN(CH₃)$\overset{\overset{O}{\|}}{C}$O(CH₂)₃CH₃ | S |
| 4-CF₃ | 5-Cl | 4-Cl-Phenyl | SN(CH₃)$\overset{\overset{O}{\|}}{C}$O(CH₂)₃CH₃ | S |
| 4-CF₃ | 4-F | 4-Cl-Phenyl | SN(CH₃)$\overset{\overset{O}{\|}}{C}$O(CH₂)₃CH₃ | S |
| 4-CF₃ | 5-F | 4-Cl-Phenyl | SN(CH₃)$\overset{\overset{O}{\|}}{C}$O(CH₂)₃CH₃ | S |
| 4-CF₃ | 5-Cl | CO₂Me | SN(iPr)SO₂CH₃ | S |
| 4-CF₃ | 4-F | CO₂Me | SN(iPr)SO₂CH₃ | S |
| 4-CF₃ | 5-F | CO₂Me | SN(iPr)SO₂CH₃ | S |
| 4-CF₃ | 5-Cl | 4-Cl-Phenyl | SN(iPr)SO₂CH₃ | S |
| 4-CF₃ | 4-F | 4-Cl-Phenyl | SN(iPr)SO₂CH₃ | S |
| 4-CF₃ | 5-F | 4-Cl-Phenyl | SN(iPr)SO₂CH₃ | S |
| 4-CF₃ | H | 4-Cl-Phenyl | SN(iPr)SO₂CH₃ | S |
| 4-Cl | H | CO₂Me | SN(CH₃)$\overset{\overset{O}{\|}}{C}$O(CH₂)₃CH₃ | NCH₃ |
| 4-OCF₂H | H | CO₂Me | SN(CH₃)$\overset{\overset{O}{\|}}{C}$O(CH₂)₃CH₃ | NCH₃ |
| 4-OCF₃ | H | CO₂Me | SN(CH₃)$\overset{\overset{O}{\|}}{C}$O(CH₂)₃CH₃ | NCH₃ |
| 4-F | H | CO₂Me | SN(CH₃)$\overset{\overset{O}{\|}}{C}$O(CH₂)₃CH₃ | NCH₃ |
| 4-CF₃ | 5-Cl | CO₂Me | SN(CH₃)$\overset{\overset{O}{\|}}{C}$O(CH₂)₃CH₃ | NCH₃ |
| 4-CF₃ | 4-F | CO₂Me | SN(CH₃)$\overset{\overset{O}{\|}}{C}$O(CH₂)₃CH₃ | NCH₃ |
| 4-CF₃ | 5-F | CO₂Me | SN(CH₃)$\overset{\overset{O}{\|}}{C}$O(CH₂)₃CH₃ | NCH₃ |
| 4-CF₃ | 5-Cl | 4-Cl—Phenyl | SN(CH₃)$\overset{\overset{O}{\|}}{C}$O(CH₂)₃CH₃ | NCH₃ |
| 4-CF₃ | 4-F | 4-Cl—Phenyl | SN(CH₃)$\overset{\overset{O}{\|}}{C}$O(CH₂)₃CH₃ | NCH₃ |
| 4-CF₃ | 5-F | 4-Cl—Phenyl | SN(CH₃)$\overset{\overset{O}{\|}}{C}$O(CH₂)₃CH₃ | NCH₃ |

TABLE 15-continued

| R₁ | R₂ | B | Y | A |
|---|---|---|---|---|
| 4-CF₃ | H | 4-Cl—Phenyl | $SN(CH_3)\overset{\overset{O}{\|}}{C}O(CH_2)_3CH_3$ | NCH₃ |
| 4-CF₃ | H | CO₂Me | SN(iPr)SO₂CH₃ | NCH₃ |
| 4-Cl | H | CO₂Me | SN(iPr)SO₂CH₃ | NCH₃ |
| 4-OCF₂H | H | CO₂Me | SN(iPr)SO₂CH₃ | NCH₃ |
| 4-OCF₃ | H | CO₂Me | SN(iPr)SO₂CH₃ | NCH₃ |
| 4-F | H | CO₂Me | SN(iPr)SO₂CH₃ | NCH₃ |
| 4-CF₃ | 5-Cl | CO₂Me | SN(iPr)SO₂CH₃ | NCH₃ |
| 4-CF₃ | 4-F | CO₂Me | SN(iPr)SO₂CH₃ | NCH₃ |
| 4-CF₃ | 5-F | CO₂Me | SN(iPr)SO₂CH₃ | NCH₃ |
| 4-CF₃ | 5-Cl | 4-Cl—Phenyl | SN(iPr)SO₂CH₃ | NCH₃ |
| 4-CF₃ | 4-F | 4-Cl—Phenyl | SN(iPr)SO₂CH₃ | NCH₃ |
| 4-CF₃ | 5-F | 4-Cl—Phenyl | SN(iPr)SO₂CH₃ | NCH₃ |
| 4-CF₃ | H | 4-Cl—Phenyl | SN(iPr)SO₂CH₃ | NCH₃ |
| 4-CF₃ | H | CO₂Me | SN(s-Bu)SO₂CH₂CH₂CH₃ | NCH₃ |
| 4-Cl | H | CO₂Me | SN(s-Bu)SO₂CH₂CH₂CH₃ | NCH₃ |
| 4-OCF₂H | H | CO₂Me | SN(s-Bu)SO₂CH₂CH₂CH₃ | NCH₃ |
| 4-OCF₃ | H | CO₂Me | SN(s-Bu)SO₂CH₂CH₂CH₃ | NCH₃ |
| 4-F | H | CO₂Me | SN(s-Bu)SO₂CH₂CH₂CH₃ | NCH₃ |
| 4-CF₃ | 5-Cl | CO₂Me | SN(s-Bu)SO₂CH₂CH₂CH₃ | NCH₃ |
| 4-CF₃ | 4-F | CO₂Me | SN(s-Bu)SO₂CH₂CH₂CH₃ | NCH₃ |
| 4-CF₃ | 5-F | CO₂Me | SN(s-Bu)SO₂CH₂CH₂CH₃ | NCH₃ |
| 4-CF₃ | 5-Cl | 4-Cl—Phenyl | SN(s-Bu)SO₂CH₂CH₂CH₃ | NCH₃ |
| 4-CF₃ | 4-F | 4-Cl—Phenyl | SN(s-Bu)SO₂CH₂CH₂CH₃ | NCH₃ |
| 4-CF₃ | 5-F | 4-Cl—Phenyl | SN(s-Bu)SO₂CH₂CH₂CH₃ | NCH₃ |
| 4-CF₃ | H | 4-Cl—Phenyl | SN(s-Bu)SO₂CH₂CH₂CH₃ | NCH₃ |
| 4-CF₃ | 5-Cl | CO₂Me | Me | S |
| 4-OCF₃ | 5-Cl | CO₂Me | Me | S |
| 4-Br | 5-Cl | CO₂Me | Me | S |
| 4-CF₃ | 5-F | CO₂Me | COCH₃ | S |
| 4-OCF₃ | 5-F | CO₂Me | COCH₃ | S |
| 4-Br | 5-F | CO₂Me | COCH₃ | S |
| 4-CF₃ | 4-Cl | CO₂Me | CO₂CH₃ | S |
| 4-OCF₃ | 5-Cl | CO₂Me | CO₂CH₃ | S |
| 4-Br | 5-Cl | CO₂Me | CO₂CH₃ | S |
| 4-CF₃ | 5-F | CO₂Me | COCF₃ | S |
| 4-OCF₃ | 5-F | CO₂Me | COCF₃ | S |
| 4-Br | 5-F | CO₂Me | COCF₃ | S |
| 4-CF₃ | 4-Cl | 4-Cl—Ph | Me | S |
| 4-OCF₃ | 4-Cl | 4-Cl—Ph | Me | S |
| 4-Br | 4-Cl | 4-Cl—Ph | Me | S |
| 4-CF₃ | 4-Cl | 4-Cl—Ph | COCH₃ | S |
| 4-OCF₃ | 4-Cl | 4-Cl—Ph | COCH₃ | S |
| 4-Br | 4-Cl | 4-Cl—Ph | COCH₃ | S |
| 4-CF₃ | 4-Cl | 4-Cl—Ph | CO₂CH₃ | S |
| 4-OCF₃ | 4-Cl | 4-Cl—Ph | CO₂CH₃ | S |
| 4-Br | 4-Cl | 4-Cl—Ph | CO₂CH₃ | S |
| 4-CF₃ | 4-Cl | 4-Cl—Ph | COCF₃ | S |
| 4-OCF₃ | 4-Cl | 4-Cl—Ph | COCF₃ | S |
| 4-Br | 4-Cl | 4-Cl—Ph | COCF₃ | S |
| 4-CF₃ | 4-Cl | 4-Cl—Ph | CO₂CH₂CH₃ | S |
| 4-OCF₃ | 4-Cl | 4-Cl—Ph | CO₂CH₂CH₃ | S |
| 4-Br | 4-Cl | 4-Cl—Ph | CO₂CH₂CH₃ | S |
| 4-CF₃ | 4-Cl | 4-F—Ph | Me | S |
| 4-OCF₃ | 4-Cl | 4-F—Ph | Me | S |
| 4-Br | 4-Cl | 4-F—Ph | Me | S |
| 4-CF₃ | 4-Cl | 4-F—Ph | COCH₃ | S |
| 4-OCF₃ | 4-Cl | 4-F—Ph | COCH₃ | S |
| 4-Br | 4-Cl | 4-F—Ph | COCH₃ | S |
| 4-CF₃ | 4-Cl | 4-F—Ph | CO₂CH₃ | S |
| 4-OCF₃ | 4-Cl | 4-F—Ph | CO₂CH₃ | S |
| 4-Br | 4-Cl | 4-F—Ph | CO₂CH₃ | S |
| 4-CF₃ | 4-Cl | 4-F—Ph | COCH₂CH₃ | S |
| 4-OCF₃ | 4-Cl | 4-F—Ph | COCH₂CH₃ | S |
| 4-Br | 4-Cl | 4-F—Ph | COCH₂CH₃ | S |
| 4-CF₃ | 5-Cl | CO₂Me | Me | O |
| 4-OCF₃ | 5-Cl | CO₂Me | Me | O |
| 4-Br | 5-Cl | CO₂Me | Me | O |
| 4-CF₃ | 5-F | CO₂Me | COCH₃ | O |
| 4-OCF₃ | 5-F | CO₂Me | COCH₃ | O |
| 4-Br | 5-F | CO₂Me | COCH₃ | O |
| 4-CF₃ | 5-Cl | CO₂Me | CO₂CH₃ | O |
| 4-OCF₃ | 5-Cl | CO₂Me | CO₂CH₃ | O |
| 4-Br | 5-Cl | CO₂Me | CO₂CH₃ | O |
| 4-CF₃ | 5-F | CO₂Me | COCF₃ | O |
| 4-OCF₃ | 5-F | CO₂Me | COCF₃ | O |
| 4-Br | 5-F | CO₂Me | COCF₃ | O |
| 4-CF₃ | 4-Cl | 4-Cl—Ph | Me | O |
| 4-OCF₃ | 4-Cl | 4-Cl—Ph | Me | O |

TABLE 15-continued

| $R_1$ | $R_2$ | B | Y | A |
|---|---|---|---|---|
| 4-Br | 4-Cl | 4-Cl—Ph | Me | O |
| 4-CF$_3$ | 4-Cl | 4-Cl—Ph | COCH$_3$ | O |
| 4-OCF$_3$ | 4-Cl | 4-Cl—Ph | COCH$_3$ | O |
| 4-Br | 4-Cl | 4-Cl—Ph | COCH$_3$ | O |
| 4-CF$_3$ | 4-Cl | 4-Cl—Ph | CO2CH$_3$ | O |
| 4-OCF$_3$ | 4-Cl | 4-Cl—Ph | CO2CH$_3$ | O |
| 4-Br | 4-Cl | 4-Cl—Ph | CO2CH$_3$ | O |
| 4-CF$_3$ | 4-Cl | 4-Cl—Ph | COCF$_3$ | O |
| 4-OCF$_3$ | 4-Cl | 4-Cl—Ph | COCF$_3$ | O |
| 4-Br | 4-Cl | 4-Cl—Ph | COCF$_3$ | O |
| 4-CH$_3$ | 4-Cl | 4-Cl—Ph | CO$_2$CH$_2$CH$_3$ | O |
| 4-OCF$_3$ | 4-Cl | 4-Cl—Ph | CO$_2$CH$_2$CH$_3$ | O |
| 4-Br | 4-Cl | 4-Cl—Ph | CO$_2$CH$_2$CH$_3$ | O |
| 4-CF$_3$ | 4-Cl | 4-F—Ph | Me | O |
| 4-OCF$_3$ | 4-Cl | 4-F—Ph | Me | O |
| 4-Br | 4-Cl | 4-F—Ph | Me | O |
| 4-CF$_3$ | 4-Cl | 4-F—Ph | COCH$_3$ | O |
| 4-OCF$_3$ | 4-Cl | 4-F—Ph | COCH$_3$ | O |
| 4-Br | 4-Cl | 4-F—Ph | COCH$_3$ | O |
| 4-CF$_3$ | 4-Cl | 4-F—Ph | CO$_2$CH$_3$ | O |
| 4-OCF$_3$ | 4-Cl | 4-F—Ph | CO$_2$CH$_3$ | O |
| 4-Br | 4-Cl | 4-F—Ph | CO$_2$CH$_3$ | O |
| 4-CF$_3$ | 4-Cl | 4-F—Ph | COCH$_2$CH$_3$ | O |
| 4-OCF$_3$ | 4-Cl | 4-F—Ph | COCH$_2$CH$_3$ | O |
| 4-Br | 4-Cl | 4-F—Ph | COCH$_2$CH$_3$ | O |

TABLE 16

| $R_1$ | $R_2$ | B | A | $R_a^1$ | $R_a^2$ |
|---|---|---|---|---|---|
| 4-CF$_3$ | 5-Cl | H | CHMe | H | H |
| 4-OCF$_3$ | 5-Cl | H | CHMe | H | H |
| 4-Cl | 5-Cl | H | CHMe | H | H |
| 4-Br | 5-Cl | H | CHMe | H | H |
| 4-OCF$_2$H | 5-Cl | H | CHMe | H | H |
| 4-CF$_3$ | 5-F | H | CHMe | H | H |
| 4-OCF$_3$ | 5-F | H | CHMe | H | H |
| 4-Cl | 5-F | H | CHMe | H | H |
| 4-Br | 5-F | H | CHMe | H | H |
| 4-OCF$_2$H | 5-F | H | CHMe | H | H |
| 4-CF$_3$ | 5-Cl | H | CH(i-Pr) | H | H |
| 4-Cl | 5-Cl | H | CH(i-Pr) | H | H |
| CF$_3$ | 5-Cl | Me | CHMe | H | H |
| OCF$_3$ | 5-Cl | Me | CH(i-Pr) | H | H |
| OCF$_2$H | 5-Cl | Me | C(Me)$_2$ | H | H |
| Cl | 5-Cl | Me | C(Me)$_2$ | H | H |
| CF$_3$ | 5-Cl | CO$_2$Me | C(Me)$_2$ | H | H |
| OCF$_3$ | 5-Cl | CO$_2$Me | C(Me)$_2$ | H | H |
| OCF$_2$H | 5-Cl | CO$_2$Me | CHEt | H | H |
| Cl | 5-Cl | CO$_2$Me | CHEt | H | H |
| CF$_3$ | 5-F | Ph | CHMe | H | H |
| OCF$_3$ | 5-F | Ph | CHMe | H | H |
| OCF$_2$H | 5-F | Ph | CHMe | H | H |
| Cl | 5-F | Ph | CHMe | H | H |
| CF$_3$ | 5-F | CO$_2$Me | CHMe | H | H |
| OCF$_3$ | 5-F | CO$_2$Me | CHMe | H | H |
| CF$_3$ | H | H | CH$_2$ | Me | H |
| OCF$_3$ | H | H | CH$_2$ | Me | H |
| CF$_3$ | H | 4-F—Ph | CH$_2$ | Me | H |
| OCF$_3$ | H | 4-F—Ph | CH$_2$ | Me | H |
| CF$_3$ | 5-Cl | CO$_2$Me | CH$_2$ | Me | H |
| OCF$_3$ | 5-Cl | CO$_2$Me | CH$_2$ | Me | H |
| CF$_3$ | 5-F | CO$_2$Me | CH$_2$ | Me | H |
| OCF$_3$ | 5-F | CO$_2$Me | CH$_2$ | Me | H |
| CF$_3$ | 5-Cl | Me | CH$_2$ | Me | Me |
| OCF$_3$ | 5-Cl | Me | CH$_2$ | Me | Me |
| CF$_3$ | 5-F | Ph | CH$_2$ | Me | Me |
| OCF$_3$ | 5-F | Ph | CH$_2$ | Me | Me |
| CF$_3$ | 5-Cl | CO$_2$Me | CH$_2$ | Me | Me |
| OCF$_3$ | 5-Cl | CO$_2$Me | CH$_2$ | Me | Me |
| CF$_3$ | H | H | O | Me | H |
| OCF$_3$ | H | H | O | Me | H |
| CF$_3$ | H | H | O | Me | Me |
| OCF$_3$ | H | H | O | Me | Me |
| CF$_3$ | 5-Cl | CO$_2$Me | O | Me | H |
| OCF$_3$ | 5-Cl | CO$_2$Me | O | Me | H |
| CF$_3$ | 5-Cl | CO$_2$Me | O | Me | H |
| OCF$_3$ | 5-Cl | CO$_2$Me | O | Me | H |
| CF$_3$ | 5-F | CO$_2$Me | O | Me | H |
| OCF$_3$ | 5-F | CO$_2$Me | O | Me | H |
| CF$_3$ | 5-F | Ph | O | Me | H |
| OCF$_3$ | 5-F | Ph | O | Me | H |
| CF$_3$ | 5-F | Me | O | Me | H |
| OCF$_3$ | 5-F | Me | O | Me | H |
| CF$_3$ | H | H | S | Me | H |
| OCF$_3$ | H | H | S | Me | H |
| CF$_3$ | H | Ph | S | Me | H |
| OCF$_3$ | 5-Cl | Ph | S | Me | H |
| CF$_3$ | 5-Cl | H | S | Me | Me |
| OCF$_3$ | 5-Cl | H | S | Me | Me |
| CF$_3$ | 5-F | Me | S | Me | H |
| OCF$_3$ | 5-F | Me | S | Me | H |
| OCF$_3$ | 5-Cl | H | CH$_2$ | Me | H |
| OCF$_3$ | 5-Cl | H | CH$_2$ | Me | H |
| CF$_3$ | 5-Cl | H | CH$_2$ | Me | Me |
| OCF$_3$ | 5-Cl | H | CH$_2$ | Me | Me |
| CF$_3$ | 5-F | H | CH$_2$ | Me | Me |
| OCF$_3$ | 5-F | H | CH$_2$ | Me | Me |

FORMULATION AND USE

The compounds of this invention will generally be used in formulation with a carrier comprising a liquid or solid diluent or an organic solvent. Useful formulations of the compounds of Formula I can be prepared in conventional ways. They include dusts, granules, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Active | Percent by Weight | |
| --- | --- | --- | --- |
|  | Ingredient | Diluent(s) | Surfactant(s) |
| Wettable Powders | 25-90 | 0-74 | 1-10 |
| Oil Suspensions, Emulsions, Solutions, (including Emulsifiable Concentrates) | 1-50 | 40-95 | 0-35 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Bookds, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

Many of the compounds of the invention are most efficacious when applied in the form of an emulsifiable concentrate mixed with a spray oil or spray oil concentrate. Although any oil can be used as a spray oil, spray oils usually have these characteristics: they are not phytotoxic to the crop sprayed, and they have appropriate viscosity. Petroleum based oils are commonly used for spraying. In some areas, crop oils are preferred such as they following:

| Common Crop Oils Used as Spray Oils | |
| --- | --- |
| Corn Oil | Linseed Oil |
| Cottonseed Oil | Soybean Oil |
| Coconut Oil | Sunflower Oil |
| Rapeseed Oil | Olive Oil |
| Peanut Oil | Palm Oil |
| Safflower Oil | Sesame Oil |
| Mustardseed Oil | Caster Oil |

The following oils also meet the criteria for a spray oil: mineral, fish and cod liver oil.

Spray oil concentrates comprise a spray oil together with one or more additional ingredients such as emulsifiers and wetting agents. A number of useful spray oil and spray oil concentrates can be found in "A Guide to Agricultural Spray Adjuvants Used in the United States" by Thomson, Thomson Publications, California, 1986.

Examples of useful formulations of compounds of the present invention are as follows:

EXAMPLE A

| Emulsifiable Concentrate | |
| --- | --- |
| methyl 7-fluoro-3A,4-dihydro-2-[[[4-(trifluoromethyl)-phenyl]amino]carbonyl]-3H-pyrazolo[5,1-c][1,4]benzoxazine-3a-carboxylate. | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

EXAMPLE B

| Wettable Powder | |
| --- | --- |
| methyl 7-fluoro-3A,4-dihydro-2-[[[4-(trifluoromethyl)-phenyl]amino]carbonyl]-3H-pyrazolo[5,1-c][1,4]benzoxazine-3a-carboxylate. | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

| Dust | |
| --- | --- |
| Wettable powder of Example B | 10% |
| pyrophyllite (powder) | 90% |

The wettable powder and the pyrophyllite diluent are thoroughly blended and then packaged. The product is suitable for use as a dust.

EXAMPLE D

| Granule | |
| --- | --- |
| methyl 7-fluoro-3A,4-dihydro-2-[[[4-(trifluoromethyl)-phenyl]amino]carbonyl]-3H-pyrazolo[5,1-c][1,4]benzoxazine-3a-carboxylate. | 10% |
| matter, 0.71/0.30 mm; U.S.S. No. 25-50 sieves) | 90% |

The active ingredient is dissolved in a volatile solvent such as acetone and sprayed upon dedusted and prewarmed attapulgite granules in a double cone blender. The acetone is then driven off by heating. The granules are then allowed to cool and are packaged.

EXAMPLE E

| Granule | |
|---|---|
| Wettable powder of Example B | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S. Ser. No. 18 to 40 sieves), the granules are removed, dried, and screened. Oversize material is crushed to produce additional material in the desired range. These granules contain 4.5% active ingredient.

EXAMPLE F

| Solution | |
|---|---|
| methyl 7-fluoro-3A,4-dihydro-2-[[[4-(trifluoro-methyl)-phenyl]amino]carbonyl]-3H-pyrazolo[5,1-c][1,4]benzoxazine-3a-carboxylate | 25% |
| N-methyl-pyrrolidone | 75% |

The ingredients are combined and stirred to produce a solution suitable for direct, low volume application.

EXAMPLE G

| Aqueous Suspension | |
|---|---|
| Methyl 7-fluoro-3A,4-dihydro-2-[[[4-(trifluoro-methyl)-phenyl]amino]carbonyl]-3H-pyrazolo[5,1-c][1,4]benzoxazine-3a-carboxylate. | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE H

| Oil Suspension | |
|---|---|
| Methyl 7-fluoro-3A,4-dihydro-2-[[[4-(trifluoro-methyl)-phenyl]amino]carbonyl]-3H-pyrazolo[5,1-c][1,4]benzoxazine-3a-carboxylate. | 35.0% |
| blend of polyalcohol carboxylic esters and oil soluble petroleum sulfonates | 6.0% |
| xylene range solvent | 59.0% |

The ingredients are combined and ground together in a sand mill to produce particles essentially all below 5 microns. The product can be used directly, extended with oils, or emulsified in water.

| Bait Granules | |
|---|---|
| Methyl 7-fluoro-3A,4-dihydro-2-[[[4-(trifluoro-methyl)-phenyl]amino]carbonyl]-3H-pyrazolo[5,1-c][1,4]benzoxazine-3a-carboxylate. | 3.0% |

| -continued | |
|---|---|
| Bait Granules | |
| blend of polyethoxylated nonyl-phenols and sodium dodecyl-benzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compound of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of the present invention can be mixed or formulated are:

INSECTICIDES 3-hydroxy-N-methylcrotonamide(dimethylphosphate)ester (monocrotophos)

methylcarbamic acid, ester with 2,3-dihydro-2,2-dimethyl-7-benzofuranol (carbofuran)

O-[2,4,5-trichloro-α-(chloromethyl)benzyl]phosphoric acid, O',O'-dimethyl ester (tetrachlorvinphos)

2-mercaptosuccinic acid, diethyl ester, S-ester with thionophosphoric acid, dimethyl ester (malathion)

phosphorothioic acid, O,O-dimethyl, O-p-nitrophenyl ester (methyl parathion)

methylcarbamic acid, ester with α-naphthol (carbaryl)

methyl O-methylcarbamoyl)thiolacetohydroxamate (methomyl)

N'-(4-chloro-o-tolyl)-N,N-dimethylformamidine (chlordimeform)

O,O-diethyl-O-(2-isopropyl-4-methyl-6-pyrimidylphosphorothioate (diazinon)

octachlorocamphene (toxaphene)

O-ethyl O-p-nitrophenyl phenylphosphonothioate (EPN)

(S)-α-cyano-m-phenoxybenzyl(1R,3R)-3-(2,2-dibromovinyl)-2,2-dimethylcyclopropanecarboxylate (deltamethrin)

Methyl N',N'-dimethyl-N-[(methylcarbamoyl)oxy]-1-thiooxamimidate (oxamyl)

cyano(3-henoxyphenyl)-methyl-4-chloro-α-(1-methylethyl)benzeneacetate (fenvalerate)

(3-phenoxyphenyl)methyl(±)-cis,trans-3-(2,2-dichloroethenyl)-2,2-dimethylcyclopropanecarboxylate (permethrin)

α-cyano-3-phenoxybenzyl 3-(2,2-dichlorovinyl)-2,2-dimethylcyclopropane carboxylate (cypermethrin)

O-ethyl-S-(p-chlorophenyl)ethylphosphonodithioate (profenofos)

phosphorothiolothionic acid, O-ethyl-O-[4-(methylthio)phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenos, methiadathion, methamidphos, monocrotophos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

FUNGICIDES methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)[]methyl]sily]methyl]-1H-1,2,4-triazole.

NEMATOCIDES

S-methyl 1-(dimethycarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

BACKTERICIDES tribasi copper sulfate
streptomycin sulfate.

ACARICIDES senecionic acid, ester with 2-sec-butyl-4,6-dinitrophenol (binapacryl)
6-methyl-1,3-dithiolol[4,5-c]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxo-thiazolidine-3-carboxamide (hexythiazox)
amitraz
propargite
fenbutatin-oxide
bisclofentezin.

BIOLOGICAL

*Bacillus thuringiensis*
Avermectin B.

UTILITY

The compounds of this invention exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against:

larvae of the order Lepidoptera including fall and beet armyworm and other Spodoptera spp., tobacco budworm, corn earworm and other Heliothis spp., European corn borer, navel orangeworm, stalk/stem borers and other pyralids, cabbage and soybean loopers and other loopers, codling moth, graph berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other Diabrotica spp., Japanese beetle, European chafer and other coleopteran grubs, and wireworms;

adults and larvae of the orders Hemiptera and Hompotera including tarnished plant bug and other plant bugs (*miridae*), aster leafhopper and other leafhoppers (*cicadellidae*), rice planthopper, brown planthopper, and other planthoppers (*fulgoroidea*), psylids, whiteflies (*aleurodidae*), aphids (*aphidae*), scales (*coccidae* and *diaspididae*), lace bugs (*tingidae*), stink bugs (*pentatomidae*), cinch bugs and other seed buts (*lygaeidae*), cicadas (*cicadidae*), spittlebugs (*cerocopids*), squash bugs (*coreidae*), red bugs and cotton stainers (*pyrrhocoridae*);

adults, larvae and eggs of the order acari (mites) including European red mite, two spotted spider mite, rust mites, McDaniel mite, and foliar feed mites;

adults and immatures of the order Orthoptera including grasshoppers;

adults and immatures of the order Diptera including leafminers, midges, fruit flies (*tephritidae*), and soil maggots;

adults and immatures of the order Thysanoptera including onion thrips and other foliar feeding thrips;

insect pests of the order Hymenoptera including carpenter ants, bees, hornets and wasps;

insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Easter subterranean termite and other termites;

insect pests of the order Mallphaga and Anoplura including the head louse, body louse, chicken head louse and other sucking and chewing parasitic lice that attack man and animals;

insect pest of the order Siphonoptera including the cat flea, dog flea and other fleas.

The specific species for which control is exemplified are: fall armyworm, *Spodoptera fruigiperda;* tobacco budworm, *Heliothis virescens;* boll weevil, *Anthonomus grandis;* aster leafhopper, *Macrosteles fascifrons;* sorther corn rootworm, *Diabrotica undecimpunctata.* The pest control protection afforded by these compounds of the present invention is limited, however, to these species.

APPLICATION

Arthropod pests are controlled and protection of agronomic crops, animal and human health is achieved by applying one or more of the Formula I compounds of this invention, in an effective amount, to the locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the solid or animal, to the plant part that is infested or needs to be protected. Alternatively, granular formulations of these compounds can be applied to or incorporated into the soil. Other methods of application can also be employed including direct and residual sprays, aerial, baits, eartags, boluses, foggers, aerosols, and many others.

The compounds of this invention can be applied in their pure state, but most often application will be of a formulation comprising one or more compounds of this invention, with suitable carriers, diluents and surfactants depending on the contemplated end use. A preferred method of application involves spraying a water dispersion of refined oil solution of the compounds. Combinations with spray oils, spray oil concentrations, and synergists such as piperonyl butoxide often enhance the efficacy of the compounds of Formula I.

The rate of application of the Formula I compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of about 0.01 to 2 kg of active ingredient per hectare are sufficient to provide large-scale effective control of pests in agronomic ecosystems under normal circumstances, but as little as 0.001 kg/hectare or as much as 8 kg/hectare may be required. For nonagronomic applications, effective use rates will range from about 0.1 t 5 mg/square foot but as little as 0.01 mg/square foot or as much as 15 mg/square foot may be required.

The following Examples demonstrate the control efficacy of the compounds of Formula I on specific insect pests wherein Compounds 1 through 44 are described in Table 17 and Compounds 45 and 46 in Table 18; and Compound 47 in Table 19.

TABLE 17

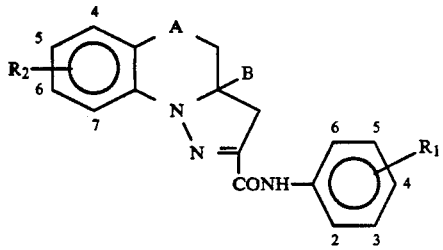

| CMPD | R₁ | R₂ | A | Y | B | m.p. °C. |
|---|---|---|---|---|---|---|
| 1 | 4-CF₃ | H | O | H | H | 157.5-158.5 |
| 2 | 4-Cl | H | O | H | H | 183-185 |
| 3 | 4-Br | H | O | H | H | 200-202 |
| 4 | 4-CF₃ | H | O | H | Ph | 183.5-185 |
| 5 | 4-OCF₂CF₂H | H | O | H | Ph | 190-191 |
| 6 | 4-Cl | H | O | H | Ph | 186-188 |
| 7 | 4-CF₃ | H | O | H | Me | 186-187 |
| 8 | 4-I | H | O | H | Me | 162-163.5 |
| 9 | 4-COMe | H | O | H | Me | 174-177 |
| 10 | 4-OCF₂CF₂H | H | O | H | Me | oil |
| 11 | 4-CF₃ | H | O | H | Ph | 106-116 |
| 12 | 4-OCF₃ | 5-Cl | O | H | Ph | 140-146 |
| 13 | 4-CF₃ | 5-F | O | H | CO₂Me | 177-181.5 |
| 14 | 4-OCF₃ | 5-F | O | H | 4-Cl—Ph | 135-139 |
| 15 | 4-Cl | 5-F | O | H | 4-Cl—Ph | 190-191 |
| 16 | 4-CF₃ | 5-F | O | H | 4-Cl—Ph | 80-84 |
| 17 | 4-CF₃ | 6-Cl | O | H | Ph | 215-215.5 |

TABLE 17-continued

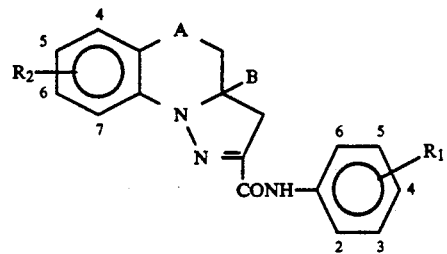

| CMPD | R₁ | R₂ | A | Y | B | m.p. °C. |
|---|---|---|---|---|---|---|
| 18 | 4-Cl | 6-Cl | O | H | Ph | 180-181 |
| 19 | 4-Br | 6-Cl | O | H | Ph | 173-175 |
| 20 | 4-CF₃ | H | SO₂ | H | Me | 265-266 |
| 21 | 4-Cl | H | SO₂ | H | Me | 192-194 |
| 22 | 4-CF₃ | H | S | H | Ph | 238-240 |
| 23 | 4-CF₃ | H | S | H | Me | 188-189 |
| 24 | 4-Cl | H | S | H | Me | 169-170 |
| 25 | 4-Br | H | S | H | Me | 163-165 |
| 26 | 4-CF₃ | 5-Cl | O | H | 4-F—Ph | 178-179 |
| 27 | 4-CF₃ | 5-Cl | O | Me | 4-F—Ph | 155-156 |
| 28 | 4-OCF₃ | 5-Cl | O | H | 4-F—Ph | 110-112 |
| 29 | 4-Br | 5-Cl | O | H | 4-F—Ph | 200-201 |
| 30 | 4-CF₃ | 5-F | O | H | Ph | 176-178 |
| 31 | 4-Br | 5-F | O | H | Ph | 162-163 |
| 32 | 4-Cl | 5-F | O | H | Ph | 192-193 |
| 33 | 4-OCF₃ | 5-F | O | H | Ph | 79-81 |
| 34 | 4-OCF₃ | 5-Cl | O | H | H | 157-158 |
| 35 | 4-CF₃ | 5-F | O | H | Me | 171-172 |
| 36 | 4-Br | 5-F | O | H | Me | 143-145 |
| 37 | 4-OCF₃ | 5-F | O | H | Me | 124-126 |
| 38 | 4-OCF₃ | 5-F | O | H | H | 138-139 |
| 39 | 4-Cl | 5-F | O | H | H | 170-172 |
| 40 | 4-CF₃ | 5-F | O | Me | H | 158-160 |
| 41 | 4-CF₃ | 5-Cl | O | H | H | 171-172 |
| 42 | 4-Br | 5-Cl | O | H | H | 177-179 |
| 43 | 4-CF₃ | 5-F | O | H | H | 171-173 |
| 44 | 4-Br | 5-F | O | H | H | 182-183 |

TABLE 18

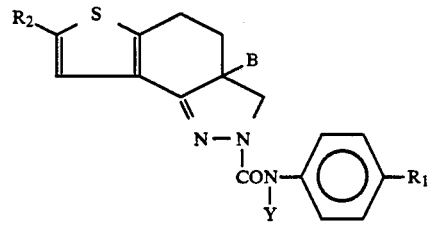

| CMPD | R₁ | R₂ | B | Y | m.p. °C. |
|---|---|---|---|---|---|
| 45 | CF₃ | H | H | H | 219-221 |
| 46 | CF₃ | Br | H | H | 196-198 |

TABLE 19

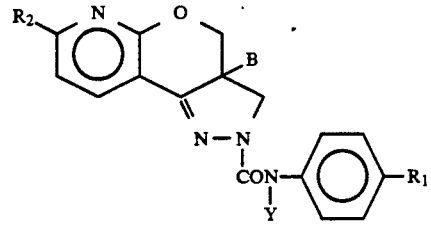

| CMPD | R₁ | R₂ | B | Y | m.p. °C. |
|---|---|---|---|---|---|
| 47 | CF₃ | H | CH₃ | H | 215-217 |

EXAMPLE 6

Fall Armyworm

Test units, each consisting of an 8-ounce plastic cup containing a layer of wheat germ diet, approximately 0.5 cm thick, were prepared. Ten third-instar larvae of fugal armyworm (*Spodoptera frugiperda*) were placed into each cup. Solutions of each of the test compounds (acetone/distilled water 75/25 solvent) were sprayed onto the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. The cups were then covered and held at 27° C. and 50% relative humidity for 72 hours, after which time readings were taken. The results are tabulated below.

| Compound | % Mortality |
| --- | --- |
| 11 | 100 |
| 12 | 100 |
| 13 | 100 |
| 14 | 100 |
| 15 | 100 |
| 16 | 100 |
| 26 | 100 |
| 27 | 100 |
| 28 | 100 |
| 29 | 100 |
| 30 | 100 |
| 31 | 100 |
| 32 | 100 |
| 33 | 100 |

EXAMPLE 7

Tobacco Budworm

The test procedure of Example 6 was repeated for efficacy against third-instar larvae of the tobacco budworm (*Heliothis virescens*) except that mortality was assessed at 48 hours. The results are tabulated below.

| Compound | % Mortality |
| --- | --- |
| 11 | 100 |
| 12 | 100 |
| 13 | 83 |
| 14 | 100 |
| 15 | 100 |
| 16 | 100 |
| 26 | 100 |
| 27 | 100 |
| 28 | 100 |
| 29 | 100 |
| 30 | 100 |
| 31 | 40 |
| 33 | 100 |

EXAMPLE 8

Southern Corn Rootworm

Test units, each consisting of an 8-ounce plastic cup containing 1 sprouted corn seed, were prepared. Sets of three test units were sprayed as described in Example 6 with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tests on Southern rootworm, the following tabulations depicts the activity:

| Compound | % Mortality |
| --- | --- |
| 11 | 100 |
| 12 | 100 |
| 13 | 100 |
| 14 | 100 |
| 15 | 100 |
| 16 | 100 |
| 26 | 100 |
| 27 | 100 |
| 28 | 100 |
| 29 | 100 |
| 30 | 100 |
| 31 | 100 |
| 32 | 100 |
| 33 | 100 |

EXAMPLE 9

Boll Weevil

Five adult boll weevils (*Anthonomus grandis*) were placed into each of a series of 9-ounce cups. The test procedure employed was then otherwise the same as in Example 6. Mortality readings were taken 48 hours after treatment. Of the compounds tested on boll weevil, the following tabulation depicts the activity:

| Compound | % Mortality |
| --- | --- |
| 11 | 100 |
| 12 | 100 |
| 13 | 93 |
| 15 | 100 |
| 16 | 93 |
| 30 | 100 |
| 31 | 100 |
| 32 | 100 |

EXAMPLE 10

Aster Leafhopper

Test units were prepared from a series of 12-ounce cups, each containing oat (*Avena Sativa*) seedlings in a 1-inch layer of sterilized soil. The test units were sprayed as described in Example 6 with indiviudual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested on aster leafhopper, the following tabulation depicts the activity:

| Compound | % Mortality |
| --- | --- |
| 11 | 88 |
| 12 | 86 |
| 13 | 100 |
| 16 | 100 |
| 26 | 87 |
| 27 | 100 |
| 28 | 95 |
| 29 | 88 |
| 30 | 100 |

| Compound | % Mortality |
|---|---|
| 33 | 82 |

What is claimed is:

1. A compound of Formula I

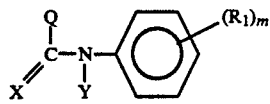      I wherein:

Q is

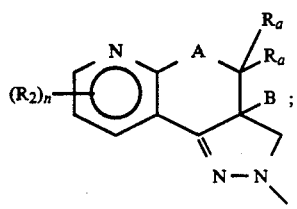  Q-1

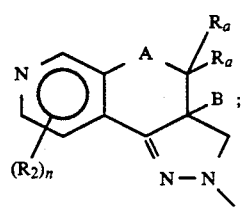  Q-2

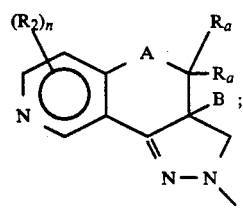  Q-3

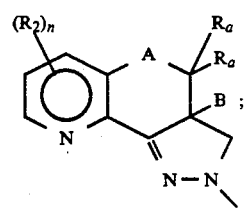  Q-4

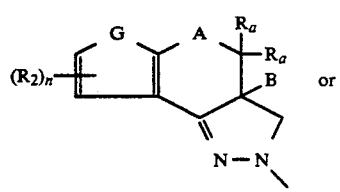  Q-5  or

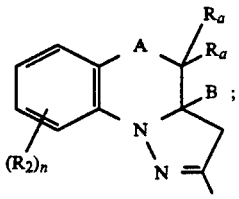  Q-8

G is O or S;

A is a 0, 1 or 2-atom bridge comprising 0 to 2 carbon atoms, 0 to 1 oxygen atoms, 0 to 1 $S(O)_q$ groups or 0 to 1 $NR_6$ groups wherein each carbon atom is optionally substituted with 1 to 2 substituents selected from $R_a$; A being other than $NR^6$ when Q is Q-8;

B is H, $C_1$ to $C_6$ alkyl, $C_3$ to $C_6$ cycloalkyl optionally substituted with 1 to 2 halogens or 1 to 2 $CH_3$, $C_4$ to $C_6$ cycloalkylalkyl, $C_1$ to $C_6$ haloalkyl, $C_2$ to $C_6$ alkenyl, $C_2$ to $C_6$ alkynyl, $C_2$ to $C_6$ alkoxyalkyl, $C_2$ to $C_6$ cyanoalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl, phenyl substituted with $(R_5)p$, benzyl, benzyl substituted with 1 to 3 substituents independently selected from W, or $OR_7$ when Q is $Q_1$ to Q-5;

W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$alkylthio, $C_1$ to $C_2$haloalkylthio, $C_1$ to $C_2$ alkylsulfonyl or $C_1$ to $C_2$ haloalkylsulfonyl;

$R_1$, $R_2$ and $R_5$ are independently selected from $R_3$, halogen, CN, $N_3$, SCN, $NO_2$, $OR_3$, $SR_3$, $SOR_3$, $SO_2R_3$, $OC(O)R_3$, $OSO_2R_3$, $CO_2R_3$, $C(O)R_3$, $C(O)NR_3R_4$, $SO_2NR_3R_4$, $NR_3R_4$, $NR_4C(O)R_3$, $OC(O)NHR_3$, $NR_rC(O)NHR_3$ and $NR_4SO_2R_3$, or when m, n or p is 2, $R_1$, $R_2$ or $R_5$ are $-OCH_2O-$, $-OCH_2CH_2O-$, or $-CH_2Ch_2O-$, each of which are substituted with 1 to 4 halogen atoms or 1 to 2 methyl groups;

$R_3$ is H, $C_1$ to $C_6$ alkyl, $C_1$ to $C_6$ haloalkyl, $C_2$ to $C_6$ alkenyl, $C_2$ to $C_6$ haloalkenyl, $C_2$ to $C_6$ alkynyl, $C_2$ to $C_6$ haloalkynyl, $C_2$ to $C_6$ alkoxyalkyl, $C_2$ to $C_6$ alkylthioalkyl, $C_1$ to $C_6$ nitroalkyl, $C_2$ to $C_6$ cyanoalkyl, $C_3$ to $C_8$ alkoxycarbonylalkyl, $C_3$ to $C_6$ cycloalkyl, $C_3$ to $C_6$ halocycloalkyl, phenyl, benzyl, or phenyl or benzyl substituted with 1 to 3 substituents independently selected from W;

$R_4$ is H, $C_1$ to $C_4$ alkyl or $R_3$ and $R_4$ are taken together as $(CH_2)_4$, $(CH_2)_5$ or $(CH_2CH_2OCH_2CH_2)$;

$R_6$ is H, $C_1$ to $C_4$ alkyl, $C_1$ to $C_4$ haloalkyl, $C_2$ to $C_4$ alkenyl, $C_2$ to $C_4$ haloalkenyl, $C_2$ to $C_4$ alkynyl, phenyl optionally substituted with W, or benzyl optionally substituted with W;

$R_7$ is H, $C_1$ to $C_4$ alkyl, $C_2$ to $C_4$ alkenyl, $C_2$ to $C_4$ alkynyl, $C_2$ to $C_4$ alkylcarbonyl, $C_2$ to $C_4$ alkoxycarbonyl;

$R_a$ is independently selected from H, $C_1$ to $C_6$ alkyl, $C_2$ to $C_4$ alkoxycarbonyl and phenyl optionally substituted with 1 to 3 substituents independently selected from W;

X is O or S;

n is 1 to 2;

m is 1 to 3;

p is 1 to 3;

q is 0 to 2;

Y is H, $C_1$ to $C_6$ alkyl, $C_2$ to $C_6$ alkoxyalkyl, CHO, $C_2$ to $C_6$ alkylcarbonyl, $C_2$ to $C_6$ alkoxycarbonyl, $C_2$ to $C_6$ haloalkylcarbonyl, $C_1$ to $C_6$ alkylthio, $C_1$ to $C_6$ haloalkylthio, phenylthio, phenylthio substituted with 1 to 3 substituents independently selected from W, or S-J;

J is

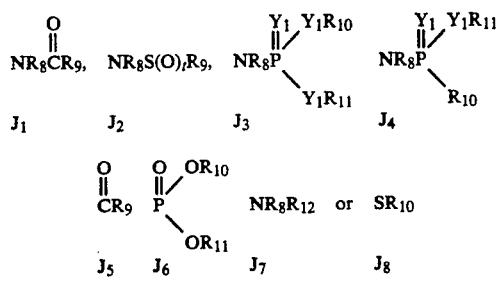

$R_8$ and $R_{12}$ are independently selected from $C_1$ to $C_6$ alkyl, $C_1$ to $C_6$ haloalkyl, $C_3$ to $C_6$ cycloalkyl, $C_4$ to $C_7$ cycloalkylalkyl, phenyl optionally substituted with 1 to 2 substituents independently selected from W, benzyl optionally substituted with 1 to 2 substituents independently selected from W, phenethyl optionally substituted with 1 to 2 substituents independently selected from W, $C_2$ to $C_6$ cyanoalkyl, $C_2$ to $C_6$ alkoxyalkyl, $C_3$ to $C_8$ alkoxycarbonylalkyl and $C_4$ to $C_8$ dialkylaminocarbonylalkyl, or $R_8$ and $R_{12}$ are taken together as $(CH_2)_4$, $(CH_2)_5$ or $(CH_2)_2O(CH_2)_2$;

$R_9$ is F, $C_1$ to $C_{22}$ alkyl, $C_1$ to $C_6$ haloalkyl, $C_1$ to $C_{22}$ alkoxy, $C_2$ to $C_8$ dialkylamino, piperidinyl, pyrollidinyl, morpholino, $C_1$ to $C_4$ haloalkoxy, $C_1$ to $C_4$ alkoxy substituted with cyano, nitro, $C_2$ to $C_4$ alkoxy, $C_4$ to $C_8$ alkoxyalkoxy, $C_1$ to $C_2$ alkylthio, $C_2$ to $C_3$ alkoxycarbonyl, $C_3$ to $C_5$ dialkylaminocarbonyl or phenyl, or $R_9$ is phenyl optionally substituted with 1 to 2 substituents independently selected from W, or phenoxy optionally substituted with 1 to 2 substituents independently selected from W;

$R_{10}$ and $R_{11}$ are independently selected from $C_1$ to $C_4$ alkyl, $C_2$ to $C_4$ haloalkyl and phenyl optionally substituted with 1 to 2 substituents independently selected from W, or $R_{10}$ and $R_{11}$ are taken together as $(CH_2)_2$, $(CH_2)_3$ or $CH_2C(CH_3)_2CH_2$;

t is 0 to 2; and $Y_1$ is O or S.

2. A compound according to claim 1 wherein:

A is $CR_1R_a$, S, O or $NR_6$;

B is H, $C_1$ to $C_6$ alkyl, $C_1$ to $C_6$ haloalkyl, $C_2$ to $C_6$ alkenyl, $C_2$ to $C_6$ alkynyl, $C_2$ to $C_6$ alkoxyalkyl, $C_3$ to $C_8$ alkoxycarbonylalkyl, $CO_2R_3$, $C(O)R_3$, $C(O)NR_3R_4$, $C(S)NR_3R_4$, $C(S)R_3$, $C(S)SR_3$, phenyl or phenyl substituted by $(R_5)p$;

W is Cl, F, Br, CN, $CF_3$, $C_1$ to $C_2$ alkyl, $C_1$ to $C_2$ alkoxy, $OCF_2H$, $OCF_3$ or $NO_2$;

$R_2$ is $R_3$, halogen, CN, SCN, $NO_2$, $OR_3$ or $SR_3$;

$R_3$ is H, $C_1$ to $C_4$ alkyl, $C_1$ to $C_2$ haloalkyl, $C_3$ to $C_4$ alkenyl, $C_3$ to $C_4$ haloalkenyl, propargyl, phenyl, benzyl, or phenyl or benzyl substituted with one of F, Cl, Br, $CF_3$, $OCF_3$, $OCF_2H$ or $NO_2$;

p is 1 or 2;

m is 1 or 2;

X is O;

Y is H, $C_1$ to $C_4$ alkyl, $SCH_3$, $SCCl_3$, $SO_2CH_3$, $SC_6H_5$, 2—$NO_2$—$C_6H_4S$, $C(O)CH_3$, $C(O)CH_2CH_3$, $C(O)CF_3$; $CO_2CH_3$, $CO_2CH_2CH_3$, or S-J;

J is $J_1$, $J_2$, $J_3$, $J_4$ or $J_5$;

$R_8$ and $R_{12}$ are independently selected from $C_1$ to $C_6$ alkyl, $C_1$ to $C_6$ haloalkyl, $C_5$ to $C_6$ cycloalkyl, $C_3$ to $C_8$ alkoxycarbonylalkyl, phenyl, benzyl and phenethyl, each phenyl, benzyl and phenethyl optionally substituted with W, or, $R_8$ and $R_{12}$ are taken together as $(CH_2)_4$, $(CH_2)_5$ or $(CH_2)_2O(CH_2)_2$;

$R_{10}$ and $R_{11}$ are independently selected from $C_1$ to $C_3$ alkyl or phenyl; and t is 2.

3. A compound according to claim 2 wherein:

B is H, $C_1$ to $C_4$ alkyl, $C_3$ to $C_4$ alkoxycarbonylalkyl, $CO_2R_3$, $C(O)R_3$, phenyl or phenyl substituted with $(R_5)p$;

$R_1$ is halogen, CN, SCN, $NO_2$, $OR_3$, $SR_3$, $SO_2R_3$, $CO_2R_3$, $C(O)R_3$ or is $R_3$ with one substituent in the 4-position;

$R_5$ is H, $R_3$, halogen, CN, SCN, $NO_2$, $OR_3$, $SR_3$, $SO_2R_3$, $C(O)R_3$, $OSO_2R_3$, $CO_2R_3$, $C(O)R_3$, $C(O)NR_3R_4$, $SO_2NR_3R_4$ or $NR_3R_4$; or, when m or p is 2;

$R_1$ and $R_5$ are taken together as —$CH_2C(CH_3)_2O$—, $OCH_2CH_2O$—, $OCF_2CF_2O$— or —$CF_2CF_2O$— to form a 5- or 6-membered fused ring;

$R_3$ is $C_1$ to $C_4$ alkyl, $C_1$ to $C_2$ haloalkyl, $C_3$ to $C_4$ alkenyl or propargyl;

$R_4$ is H or $CH_3$;

$R_a$ is H, $CH_3$, $CO_2CH_3$ or $CO_2CH_2CH_3$;

m and p are independently 1 or 2 and one substituent is in the para-position;

Y is H, $CH_3$, $COCH_3$, $CO_2CH_3$ or S-J;

J is $J_1$ or $J_2$;

$R_8$ is $C_1$ to $C_4$ alkyl or phenyl optionally substituted with Cl or $CH_3$;

$R_9$ is $C_1$ to $C_{20}$ alkyl, $C_1$ to $C_{20}$ alkoxy, $C_1$ to $C_6$ haloalkyl, dimethylamino, phenyl optionally substituted with Cl or $CH_3$, or, $R_9$ is $C_1$ to $C_4$ alkoxy substituted with $C_2$ to $C_4$ alkoxy or 1 to 6 halogens; and G is S.

4. A compound according to claim 3 wherein:

$R_1$ is Cl, F, Br, $CF_3$, CN, $OCF_3$, $OCF_2H$, $OCF_2CF_2H$ or $SCF_2H$;

$R_2$ and $R_5$ are independently H, CL, F, Br, CN, $CF_3$, $CH_3$, $OCH(CH_3)_2$, $OCF_2H$, $OCF_3$, $SCH_3$, $SCF_2H$, $NO_2$ or $OCH_2CF_3$;

B is H, $CH_3$, $CH_2CH_3$, $CH(CH_3)_2$, $CO_2CH_3$, $CO_2CH_2CH_3$, phenyl or phenyl substituted with $(R_5)p$; and $R_a$ is H or $CH_3$.

5. A compound according to claim 4 wherein: A is O or $CH_2$.

6. A compound according to claim 5 wherein: Q is Q-1.

7. A compound according to claim 5 wherein: Q is Q-2.

8. A compound according to claim 5 wherein: Q is Q-3.

9. A compound according to claim 5 wherein: Q is Q-4.

10. A compound according to claim 5 wherein: Q is Q-5.

11. A compound according to claim 5 wherein: Q is Q-8.

12. A compound according to claim 6 which is: methyl 3,3a,4,5-tetrahydro-2-[[[4-trifluoromethyl)-phenyl]-amino]carbonyl]-2H-pyrazolo[3,4-f]-quinoline-3a-carboxylate.

13. A compound according to claim 9 which is: methyl 3,3a,4,5-tetrahydro-2-[[[4-trifluoromethyl)-phenyl]-amino]carbonyl]-2H-pyrazolo[4,3-h]-quinoline-3a-carboxylate.

14. A compound according to claim 11 which is: methyl 7-fluoro-3A,4-dihydro-2-[[[4-(trifluoromethyl)-phenyl]amino]carbonyl]-3H-pyrazolo[5,1-c]-[1,4]benzoxazine-3a-carboxylate.

15. A compound according to claim 11 which is: 7-chloro-3A-(4-fluorophenyl)-3A,4-dihydro-N-[4-(trifluoromethyl)phenyl]-3H-pyrazolo[5,1-c][1,4]-benzoxazine-2carboxamide.

16. An arthropodicidal composition comprising an arthropodically effective amount of a compound according to any one of claims 1-10, 11-13, 14, 15 or 18 a carrier therefor.

17. A method for controlling arthropods comprising applying to them or their environment an arthropodically effective amount of a compound according to any one of claims 1-10, 13-15, 17, 18 or 21.

18. A compound according to claim 10 which is: methyl 7-chloro-3,3a,4,5-tetrahydro-N-[[[4-trifluoromethyl)-phenyl]amino]carbonyl]-2H-thieno [2,3-g]-indazole-3a-carboxylate.

* * * * *